US010864164B2

(12) United States Patent
Schwier et al.

(10) Patent No.: US 10,864,164 B2
(45) Date of Patent: Dec. 15, 2020

(54) TAMPER-RESISTANT TABLET PROVIDING IMMEDIATE DRUG RELEASE

(71) Applicant: Grünenthal GmbH, Aachen (DE)

(72) Inventors: Sebastian Schwier, Aachen (DE); Marcel Haupts, Stolberg (DE); Lutz Barnscheid, Mönchengladbach (DE); Jana Pätz, Bonn (DE)

(73) Assignee: Grünenthal GmbH, Aachen (DE)

( * ) Notice: Subject to any disclaimer, the term of this patent is extended or adjusted under 35 U.S.C. 154(b) by 0 days.

(21) Appl. No.: 16/225,418

(22) Filed: Dec. 19, 2018

(65) Prior Publication Data

US 2019/0125680 A1 May 2, 2019

Related U.S. Application Data

(62) Division of application No. 13/559,644, filed on Jul. 27, 2012, now Pat. No. 10,201,502.

(60) Provisional application No. 61/512,943, filed on Jul. 29, 2011.

(30) Foreign Application Priority Data

Jul. 29, 2011 (EP) .................................... 11006254

(51) Int. Cl.
| | |
|---|---|
| *A61K 31/135* | (2006.01) |
| *A61K 31/137* | (2006.01) |
| *A61K 31/138* | (2006.01) |
| *A61K 9/20* | (2006.01) |

(52) U.S. Cl.
CPC .......... *A61K 9/2081* (2013.01); *A61K 31/135* (2013.01); *A61K 31/137* (2013.01); *A61K 31/138* (2013.01)

(58) Field of Classification Search
None
See application file for complete search history.

(56) References Cited

U.S. PATENT DOCUMENTS

| | | |
|---|---|---|
| 2,524,855 A | 10/1950 | Schnider et al. |
| 2,806,033 A | 9/1957 | Lewenstein et al. |
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,658,259 A | 4/1972 | Ledergerber et al. |
| 3,806,603 A | 4/1974 | Gaunt et al. |
| 3,865,108 A | 2/1975 | Hartop |
| 3,966,747 A | 6/1976 | Monkovic et al. |
| 3,980,766 A | 9/1976 | Shaw et al. |
| 3,941,865 A | 12/1976 | Miller et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,711,894 A | 12/1987 | Wenzel et al. |
| 4,713,243 A | 12/1987 | Schiraldi et al. |
| 4,744,976 A | 5/1988 | Snipes et al. |
| 4,764,378 A | 8/1988 | Keitn et al. |

(Continued)

FOREIGN PATENT DOCUMENTS

| | | |
|---|---|---|
| AR | 046994 A1 | 12/2004 |
| AR | 045353 A1 | 10/2005 |

(Continued)

OTHER PUBLICATIONS

Romach et al. "Update on tamper-resistant drug formulations," Drug and Alcohol Dependence, 130 (2013), 13-23.
Claffey et al, "Amphetamine Adducts of Melanin Intermediates Demonstrated by Matrix-Assisted Laser Desorption Ionization Time-of-Flight Mass Spectrometry," Chem. Res. Toxicol. 2001, 14, 1339-1344.
Evans, J.C, et. Al. "Optimal tocopherol concentrations to inhibit soybean oil oxidation," Journal of the American Oil Chemists' Society 79.1 (2002): 47-51.
Quinn, M.E. "Alpha Tocopherol" in Handbook of Pharmaceuical Excipients, Sixth Edition (2009), 31-33.

(Continued)

*Primary Examiner* — David J Blanchard
*Assistant Examiner* — Daniel F. Coughlin
(74) *Attorney, Agent, or Firm* — Norris McLaughlin, P.A

(57) ABSTRACT

The invention relates to a tamper-resistant tablet comprising
(i) a matrix material in an amount of more than one third of the total weight of the tablet; and
(ii) a plurality of coated particulates in an amount of less than two thirds of the total weight of the tablet; wherein said particulates comprise a pharmacologically active compound and a physiologically acceptable polymer, preferably a polyalkylene oxide; and form a discontinuous phase within the matrix material;
which preferably provides under in vitro conditions immediate release of the pharmacologically active compound in accordance with Ph. Eur.;
and method of using said tablet to treat pain and other conditions.

15 Claims, 8 Drawing Sheets

(56) References Cited

U.S. PATENT DOCUMENTS

| | | |
|---|---|---|
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,954,346 A | 9/1990 | Sparta et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinity |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,194 A | 4/1993 | Edgren et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | Mc Ginity et al. |
| 5,229,164 A | 7/1993 | Pins et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Graudums et al. |
| 5,811,126 A | 9/1998 | Krishnamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,914,132 A | 6/1999 | Kelm et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merrill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,228,863 B1 | 5/2001 | Palermo et al. |
| 6,235,825 B1 | 5/2001 | Yoshida et al. |
| 6,238,697 B1 | 6/2001 | Kumar et al. |
| 6,245,357 B1 | 6/2001 | Edgren et al. |
| 6,248,737 B1 | 6/2001 | Buschmann et al. |
| 6,251,430 B1 | 6/2001 | Zhang et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,811 B1 | 11/2001 | Verma et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,384,020 B1 | 5/2002 | Flanner et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,455,052 B1 | 9/2002 | Marcussen et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breitenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,946,146 B2 | 9/2005 | Mulye |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |

(56) References Cited

U.S. PATENT DOCUMENTS

| | | |
|---|---|---|
| 7,842,307 B2 | 11/2010 | Oshlack et al. |
| 7,851,482 B2 | 12/2010 | Dung et al. |
| 7,932,258 B2 | 4/2011 | Petereit et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric et al. |
| 8,101,630 B2 | 1/2012 | Kumar et al. |
| 8,114,383 B2 | 2/2012 | Bartholomaeus et al.. |
| 8,114,384 B2 | 2/2012 | Arkenau et al. |
| 8,114,838 B2 | 2/2012 | Marchionni |
| 8,192,722 B2 | 6/2012 | Arkenau Maric et al. |
| 8,202,542 B1 | 6/2012 | Mehta et al. |
| 8,309,060 B2 | 11/2012 | Bartholomaeus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Marice et al. |
| 8,858,963 B1 | 10/2014 | Devarakonda et al. |
| 8,901,113 B2 | 12/2014 | Leech et al. |
| 9,044,758 B2 | 6/2015 | Niwa et al. |
| 9,192,578 B2 | 11/2015 | McGinity et al. |
| 9,463,165 B2 | 10/2016 | Shimatani et al. |
| 9,629,807 B2 | 4/2017 | Arkenau-Maric et al. |
| 9,675,610 B2 | 6/2017 | Bartholomaeus et al. |
| 9,737,490 B2 | 8/2017 | Barnscheid et al. |
| 9,750,701 B2 | 9/2017 | Jans et al. |
| 9,855,263 B2 | 1/2018 | Wening et al. |
| 9,884,022 B2 | 2/2018 | Deshmukh et al. |
| 9,925,146 B2 | 3/2018 | Barnscheid et al. |
| 10,058,548 B2 | 8/2018 | Arkenau-Maric et al. |
| 10,130,591 B2 | 11/2018 | Bartholomäus et al. |
| 10,154,966 B2 | 12/2018 | Barnscheidt et al. |
| 10,369,109 B2 | 8/2019 | Bartholomaeus et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0187192 A1 | 12/2002 | Joshi et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0059397 A1 | 3/2003 | Hughes |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0077327 A1 | 4/2003 | Durig et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0158265 A1 | 8/2003 | Radhakrishnan et al. |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0224051 A1 | 12/2003 | Fink et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0049079 A1 | 3/2004 | Murray et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara et al. |
| 2004/0213848 A1 | 10/2004 | Li et al. |
| 2004/0253310 A1 | 12/2004 | Fischer et al. |
| 2005/0015730 A1 | 1/2005 | Gunturi et al. |
| 2005/0058706 A1 | 3/2005 | Bartholomaeus et al. |
| 2005/0063214 A1 | 3/2005 | Takashima |
| 2005/0079138 A1 | 4/2005 | Chickering, III et al. |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogmann et al. |
| 2005/0031546 A1 | 12/2005 | Bartholomaeus et al. |
| 2005/0266084 A1 | 12/2005 | Li et al. |
| 2005/0271594 A1 | 12/2005 | Groenewoud |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedmann et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0204575 A1 | 9/2006 | Feng et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0048373 A1 | 3/2007 | Chastain et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |

(56) References Cited

U.S. PATENT DOCUMENTS

| | | |
|---|---|---|
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264326 A1 | 11/2007 | Guimberteau et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0014228 A1 | 1/2008 | Darmuzey et al. |
| 2008/0020032 A1 | 1/2008 | Crowley et al. |
| 2008/0063725 A1 | 3/2008 | Gijimbenittaiietal: |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 3/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyendecker et al. |
| 2008/0152595 A1 | 6/2008 | Emigh et al. |
| 2008/0181932 A1 | 7/2008 | Bortz et al. |
| 2008/0207757 A1 | 8/2008 | Mickle |
| 2008/0220079 A1 | 9/2008 | Chen |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0260836 A1 | 10/2008 | Boyd |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0087486 A1 | 4/2009 | Krumme |
| 2009/0117191 A1 | 5/2009 | Brown Miller et al. |
| 2009/0143478 A1 | 6/2009 | Richardson et al. |
| 2009/0155357 A1 | 6/2009 | Muhuri |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0258066 A1 | 10/2009 | Venkatesh et al. |
| 2009/0317355 A1 | 12/2009 | Roth et al. |
| 2009/0318395 A1 | 12/2009 | Schramm et al. |
| 2010/0015223 A1 | 1/2010 | Cailly-Dufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Andersen et al. |
| 2010/0221322 A1 | 9/2010 | Bartholomaus et al. |
| 2010/0239667 A1 | 9/2010 | Hemmingsen et al. |
| 2010/0249045 A1 | 9/2010 | Babul |
| 2010/0260833 A1 | 10/2010 | Bartholomaus et al. |
| 2010/0260844 A1 | 10/2010 | Scicinski et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2010/0316712 A1 | 12/2010 | Nangia et al. |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0077238 A1 | 3/2011 | Leech et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0135731 A1 | 6/2011 | Kao et al. |
| 2011/0159100 A1 | 6/2011 | Andersen et al. |
| 2011/0187017 A1 | 8/2011 | Haupts |
| 2011/0223244 A1 | 9/2011 | Liversidge et al. |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0277319 A1 | 11/2012 | Steigerwald et al. |
| 2012/0321716 A1 | 12/2012 | Vachon et al. |
| 2013/0017262 A1 | 1/2013 | Mullen et al. |
| 2013/0022654 A1 | 1/2013 | Deshmukh et al. |
| 2013/0028970 A1 | 1/2013 | Schwier et al. |
| 2013/0028972 A1 | 1/2013 | Schwier et al. |
| 2013/0059010 A1 | 3/2013 | Herry et al. |
| 2013/0090349 A1 | 4/2013 | Gei Ler et al. |
| 2013/0129825 A1 | 5/2013 | Billoet |
| 2013/0129826 A1 | 5/2013 | Gei Ler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomaus et al. |
| 2013/0280338 A1 | 10/2013 | Wenig et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0034885 A1 | 2/2014 | Leech |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0271848 A1 | 9/2014 | Guido et al. |
| 2014/0275143 A1 | 9/2014 | Devarakonda et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wenig et al. |
| 2015/0030677 A1 | 1/2015 | Adjei et al. |
| 2015/0313850 A1 | 1/2015 | Krishnamurti et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0190348 A1 | 7/2015 | Haksar et al. |
| 2015/0374630 A1 | 12/2015 | Arkenau Maric et al. |
| 2016/0089439 A1 | 3/2016 | Rajagopalan |
| 2016/0175256 A1 | 6/2016 | Bartholomaeus et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau-Maric et al. |
| 2016/0346274 A1 | 12/2016 | Vaka et al. |
| 2016/0361308 A1 | 12/2016 | Bartholomaeus et al. |
| 2016/0367549 A1 | 12/2016 | Bartholomaeus et al. |

(56) References Cited

U.S. PATENT DOCUMENTS

| | | | |
|---|---|---|---|
| 2017/0027886 A1 | 2/2017 | Bartholomaeus et al. | |
| 2017/0112766 A1 | 4/2017 | Wenig et al. | |

FOREIGN PATENT DOCUMENTS

| | | |
|---|---|---|
| AR | 049562 A1 | 8/2006 |
| AR | 049839 A1 | 9/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| AU | 2009299810 B2 | 4/2010 |
| AU | 2006311116 B2 | 1/2013 |
| BR | PI0413318 A | 10/2006 |
| BR | PI0413361 A | 10/2006 |
| BR | PI0513300 A | 5/2008 |
| BR | PI0606145 A2 | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 2229621 A1 | 3/1998 |
| CA | 2317747 A1 | 7/1999 |
| CA | 2343234 A1 | 3/2000 |
| CA | 2352874 A1 | 6/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 A | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101578096 A | 11/2009 |
| CN | 101652128 A | 2/2010 |
| CN | 102413835 A | 4/2012 |
| CN | 102821757 A | 12/2012 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102004032103 A1 | 1/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP066345 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A2 | 9/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0358105 A1 | 3/1990 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |

(56) References Cited

FOREIGN PATENT DOCUMENTS

| | | |
|---|---|---|
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0761211 A1 | 3/1997 |
| EP | 0780369 A1 | 6/1997 |
| EP | 0785775 A1 | 7/1997 |
| EP | 0809488 A1 | 12/1997 |
| EP | 0820698 A1 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0980894 A1 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 A2 | 10/2002 |
| EP | 1251120 A1 | 10/2002 |
| EP | 1293127 A2 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 B1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1813276 A1 | 8/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 20070272 T3 | 11/2007 |
| JP | S36-022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | H0517566 A | 1/1993 |
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | H10251149 A | 9/1998 |
| JP | 2000513333 A | 10/2000 |
| JP | 2002524150 A | 8/2002 |
| JP | 2002-275175 A | 9/2002 |
| JP | 2003113119 A | 4/2003 |
| JP | 2003125706 A | 5/2003 |
| JP | 2003526598 A | 9/2003 |
| JP | 2004143071 A | 5/2004 |
| JP | 2004530676 A | 10/2004 |
| JP | 2005506965 A | 3/2005 |
| JP | 2005515152 A | 5/2005 |
| JP | 2005534664 A | 11/2005 |
| JP | 2006506374 A | 2/2006 |
| JP | 2007501201 A | 1/2007 |
| JP | 2007501202 A | 1/2007 |
| JP | 20070039041 A | 4/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009524626 A | 7/2009 |
| JP | 2009531453 A | 9/2009 |
| JP | 2009536927 A | 10/2009 |
| JP | 2009537456 A | 10/2009 |
| JP | 2010505949 A | 2/2010 |
| JP | 2010527285 A | 8/2010 |
| JP | 2010534204 A | 11/2010 |
| JP | 2011504455 A | 2/2011 |
| JP | 2011506493 A | 3/2011 |
| JP | 2011510034 A | 3/2011 |
| JP | WO 2011/059074 A1 | 5/2011 |
| JP | 2012515735 A | 7/2012 |
| JP | 2012528845 A | 11/2012 |
| JP | 2012533586 A | 12/2012 |
| JP | 2013523804 A | 6/2013 |
| JP | 2013155124 A | 8/2013 |
| JP | 2013536810 A | 9/2013 |
| JP | 2014505736 A | 3/2014 |
| JP | 2014-524925 A | 9/2014 |
| JP | 2014528437 A | 10/2014 |
| JP | 6085307 B2 | 2/2017 |
| JP | 2013523780 A | 6/2017 |
| KR | 1020060069832 A | 6/2006 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |

(56) References Cited

FOREIGN PATENT DOCUMENTS

| | | |
|---|---|---|
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |
| RU | 2198197 C2 | 2/2003 |
| RU | 2220715 C2 | 1/2004 |
| RU | 2328275 C2 | 5/2004 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 2567723 C2 | 11/2015 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | 1254634 B | 5/2006 |
| WO | WO 1980/000841 A1 | 5/1980 |
| WO | WO 1989/005624 A1 | 6/1989 |
| WO | WO 1990/003776 A1 | 4/1990 |
| WO | WO 1993/006723 A1 | 4/1993 |
| WO | WO 93/10765 A1 | 6/1993 |
| WO | WO 1993/010758 A1 | 6/1993 |
| WO | WO 1993/011749 A1 | 6/1993 |
| WO | WO 1993/023017 A1 | 11/1993 |
| WO | WO 1994/006414 A1 | 3/1994 |
| WO | WO 1994/008567 A1 | 4/1994 |
| WO | WO 1995/017174 A1 | 6/1995 |
| WO | WO 1995/020947 A1 | 8/1995 |
| WO | WO 1995/022319 A1 | 8/1995 |
| WO | WO 1995/030422 A1 | 11/1995 |
| WO | WO 1996/000066 A1 | 1/1996 |
| WO | WO 1996/003979 A1 | 2/1996 |
| WO | WO 1996/014058 A1 | 5/1996 |
| WO | WO 1997/000673 A1 | 1/1997 |
| WO | WO 1997/033566 A2 | 9/1997 |
| WO | WO 1997/049384 A1 | 12/1997 |
| WO | WO 1998/035655 A3 | 2/1998 |
| WO | WO 1998/020073 A2 | 5/1998 |
| WO | WO 1998/028698 A1 | 7/1998 |
| WO | WO 1998/035655 A2 | 8/1998 |
| WO | WO 1998/051758 A1 | 11/1998 |
| WO | WO 1999/012864 A1 | 3/1999 |
| WO | WO 1999/032120 A1 | 7/1999 |
| WO | WO 1999/044591 A1 | 9/1999 |
| WO | WO 1999/045887 A2 | 9/1999 |
| WO | WO 1999/048481 A1 | 9/1999 |
| WO | WO 00/15261 A1 | 3/2000 |
| WO | WO 2000/013647 A1 | 3/2000 |
| WO | WO 2000/033835 A1 | 6/2000 |
| WO | WO 2000/040205 A2 | 7/2000 |
| WO | WO 2001/008661 A2 | 2/2001 |
| WO | WO 2001/012230 A1 | 2/2001 |
| WO | WO 2001/015667 A1 | 3/2001 |
| WO | WO 2001/052651 A2 | 7/2001 |
| WO | WO 2001/058451 A1 | 8/2001 |
| WO | WO 2001/097783 A1 | 12/2001 |
| WO | WO 2002/026061 A1 | 4/2002 |
| WO | WO 2002/026262 A2 | 4/2002 |
| WO | WO 2002/026928 A1 | 4/2002 |
| WO | WO 2002/035991 A2 | 5/2002 |
| WO | WO 2002/071860 A1 | 9/2002 |
| WO | WO 2002/088217 A1 | 11/2002 |
| WO | WO 2002/094254 A2 | 11/2002 |
| WO | WO 2003/006723 A1 | 1/2003 |
| WO | WO 2003/007802 A2 | 1/2003 |
| WO | WO 2003/013433 A2 | 2/2003 |
| WO | WO 2003/013476 A1 | 2/2003 |
| WO | WO 2003/013479 A1 | 2/2003 |
| WO | WO 2003/013538 A1 | 2/2003 |
| WO | WO 2003/015531 A2 | 2/2003 |
| WO | WO 2003/018015 A1 | 3/2003 |
| WO | WO 2003/024426 A1 | 3/2003 |
| WO | WO 2003/024430 A1 | 3/2003 |
| WO | WO 2003/026624 A1 | 4/2003 |
| WO | WO 2003/026743 A2 | 4/2003 |
| WO | WO 2003/028698 A1 | 4/2003 |
| WO | WO 2003/028990 A1 | 4/2003 |
| WO | WO 2003/031546 A1 | 4/2003 |
| WO | WO 2003/035029 A1 | 5/2003 |
| WO | WO 2003/035053 A1 | 5/2003 |
| WO | WO 2003/035054 A1 | 5/2003 |
| WO | WO 2003/035177 A2 | 5/2003 |
| WO | WO 2003/039561 A1 | 5/2003 |
| WO | WO 2003/049689 A2 | 6/2003 |
| WO | WO 2003/053417 A2 | 7/2003 |
| WO | WO 2003/068392 A1 | 8/2003 |
| WO | WO 2003/070191 A1 | 8/2003 |
| WO | WO 2003/092648 A1 | 11/2003 |
| WO | WO 2003/094812 A1 | 11/2003 |
| WO | WO 2003/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037222 A2 | 5/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/043449 A1 | 5/2004 |
| WO | WO 2004/066910 A2 | 8/2004 |
| WO | WO 2004/078212 A2 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/002553 | 1/2005 |
| WO | WO 2005/002553 A2 | 1/2005 |
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/024881 A2 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/093642 A2 | 8/2007 |
| WO | WO 2007/103105 A2 | 9/2007 |
| WO | WO 2007/103286 A2 | 9/2007 |
| WO | WO 2007/112273 A2 | 10/2007 |

(56) References Cited

FOREIGN PATENT DOCUMENTS

| WO | WO 2007/112285 A2 | 10/2007 |
|----|----|----|
| WO | WO 2007/112286 A2 | 10/2007 |
| WO | WO 2007/131357 A1 | 11/2007 |
| WO | WO 2007/138466 A2 | 12/2007 |
| WO | WO 2007/149438 A2 | 12/2007 |
| WO | WO 2008/023261 A1 | 2/2008 |
| WO | WO 2008/033523 A1 | 3/2008 |
| WO | WO 2008/045060 A1 | 4/2008 |
| WO | WO 2008/069941 A2 | 6/2008 |
| WO | WO 2008/086804 A2 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/135680 A1 | 11/2009 |
| WO | WO 2010/022193 A2 | 2/2010 |
| WO | WO 2010/037854 A2 | 4/2010 |
| WO | WO 2010/044842 A1 | 4/2010 |
| WO | WO 2010-0047370 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/124953 A2 | 10/2011 |
| WO | WO 2011/124953 A3 | 10/2011 |
| WO | WO 2011/128630 A2 | 10/2011 |
| WO | WO 2011/141241 A1 | 11/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/085657 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/025449 A1 | 3/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/158810 A1 | 10/2013 |
| WO | WO 2013/167735 A1 | 11/2013 |
| WO | WO 2014/032741 A1 | 3/2014 |
| WO | WO 2014/059512 A1 | 4/2014 |
| WO | WO 2014/140231 A1 | 9/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/023675 A2 | 2/2015 |
| WO | WO 2015/048597 A1 | 4/2015 |
| WO | WO 2015/103379 A1 | 7/2015 |
| WO | WO 2015/120201 A1 | 8/2015 |
| WO | WO 2017/178658 A1 | 10/2017 |

OTHER PUBLICATIONS

Agarwal, G, et al, "Oral Sustained Release Tablets: An Overview with a Special Emphasis on Matrix Tablet," American Journal of Advanced Drug Delivery, 2017.
Brzeclo, W.,et al., "The Advent of a new Pseudoephedrine Product to Combat Methampetamine Abuse," Am J Drug Alcohol Abuse, 2013: 39(5): 284-290.
Extended European Search Report for Application No. EP 17173240. 7, dated Nov. 28, 2017.
Jamini, M., et al, "Sustained Release Matrix Type Drug Delivery System: A Review," Journal of Drug Delivery & Therpeutics; 2012 2(6), 142-148.
Kelly, C. et al, "Methamphetamine Synthesis Inhibition: Dissolving Metal Reductions," Johns Hopkins Univ. Applied Physics Lab., 2015, 1-10.
"Low Substituted Hydroxypropyl Celluslose", Drugs.com, from https://www.drugs,com/inactive/low-susbstitute-hydroxypropyl-cellulose-581.html (2018).
Misal, R, et al., "Matrix Tablet: A Promising Technique for Controlled Drug Delivery," Indo American Journal of Pharmaceutical Research, 2013.
Patrick, K., et al., "Pharmacology of Methylphenidate, Amphetamine Enantiomers and Pemoline in Attention-Deficit Hyperactivity Disorder," Human Psychopharmacology, vol. 12, 527-546 (1997).
Presley, B. et al., "Efficiency of Extraction and Conversion of Pseudoephedrine to Methamphetamine from Tamper-Resistant and Non-Tamper-Resistant Formulations," Journal of Pharmaceutical and Biomedical Analysis , 2018, 16-22.
Qi et al, "An Investigation into the Crystallisation Behavior of an Amorphous Cryomilled Pharmaceutical Material Above and Below the Glass Transition Temperature," Journal of Pharmaceutical Sciences, 2009, 196-208.
Targin(R) Product Monograph. Purdue Pharma. Revised Mar. 1, 2016.
Decision of the United States District Court for the Southern District of New York, in in re *Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in in re *Oxycontin Antitrust Litigation, Purdue Pharma LP* v. *Teva Pharmaceuticals*, Findings of Fact and Conclusions of Law, District Judge Sidney H. Stein, New York, New York, Jan. 14, 2014.
U.S. Court of Appeals, Federal Circuit, *Purdue Pharma L.P.* v. *Epic Pharma, LLC*, 117USPQ2d 1733 (Fed. Cir. 2016).
Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M.et al., "Ethylene Oxide Polymers", in Kirk-Othmer Encyclopedia of Chemical Technology, 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.

(56) References Cited

OTHER PUBLICATIONS

Balogh, E., "Tastes in and Tastes of Paprika," in Taste: Proceedings of the Oxford Symposium on Food and Cookery 28 (Tom Jaine Ed.) 1988, pp. 25-40.
Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the 29$^{th}$ Annual Meeting of the Controlled Release Society, in collaboration with the Korea Society for Biomaterials, Minneapolis, 1$^{st}$ Edition, 2002, 984-985.
Ciccone, P. E., "Attempted Abuse of Concerta," Letters to the Editor, J. Am. Acad. Child Adolesc. Psychiatry, 41:7 (Jul. 2002).
Controvensies in ADHD: A Breakfast Symposium—Concerta.
Crowley, M. et al., Pharmaceutical Applications of Hot-Melt Extrusion: Part I. Drug Dev. & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of the University of Texas at Austin. (May 2003).
Crowley, M., et al., "Evaluation of a Hot Melt Extrusion Technique using a Hydrophilic thermal Polymer and Retardant for the Preparation of Extended Release Chlorpheniramine Maleate Tablets," in American Association of Pharmaceutical Scientists: Indianapolis, IN (2000).
Crowley0000001-Crowley0000127 (2015).
Davies, N. "Sustained Release and Enteric Coated NSAIDs: Are They Really GI Safe?" J. Pharm. & Pharmaceut. Sci., 2(1):5-14, 1999.
Declaration of Dr. James W. McGinty, dated Oct. 28, 2009; online, retrieved from http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D. K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: Polyox(TM) WSR 30" (effective date: Sep. 18, 2001).
Dow, "Polyox Water-Soluble Resins: Degradation of Water-Soluble Resins," Technical Data (Oct. 2002).
Dug Bank "Oxymorphone," 2015; online, available at: www.dmgbank.ca/chugs/db01192 printed Jul. 1, 2015.
*Endo Pharmaceuticals Inc. v. Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.
FDA, "Notice of Determination that OxyContin Drug Products Covered by NDA 20-553 Were Withdrawn From Sale for Reasons or Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/21121lbl.pdf.

Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).
Jaffe, S.L., "Failed Attempts at Intranasal Abuse of Concerta," Letters to the Editor, J. Am. Acad. Child Adolesc. Psychiatry, 41:1 (Jan. 2002).
Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.
Joint Claim Construction and Prehearing Statement, dated Jul. 11, 2014. *Janssen Pharmaceuticals, Inc. and Grünenthal GMBH v. Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH v. Roxane Laboratories, Inc.*, Civil Action No. 2:13-cv-06929 CCC-MF (D.N.J.), and *Janssen Pharmaceuticals, Inc. and Grünenthal GMBH v. Alkem Laboratories Limited*, Civil Action No. 2:13-cv-07803 CCC-MF (D.N.J.).
Kibbe, Coloring Agents, in Handbook of Pharmaceutical Excipients (3d ed. 2000).
Kidokoro, M. et al. ,"Properties of Tablets Containing Granulations of Ibuprofen and Acrylic Copolymers Prepared by Thermal Processes," Pharm Dev. and Tech. , 6:263-275 (2001).
Kinjo, N. et al, "Antiplasticization in the Slightly Plasticized Poly(vinyl chloride)," Polymer Journal 4(2):143-153 (1973).
Larhib, H. et al., "Compressing polyethyelene glycols: the effect of compression pressure and speed," Int '1 J Pharmaceutics (1997) 147: 199-205.
Lieberman, H., et al., Pharmaceutical Dosage Forms: Tablets, vol. 2, Ch. 5: Granulation Technology and Tablet Characterization (1990), Table of contents and 245-348.
Lyons et al., "Twitch Interpolation in the Assessment of the Maximum Force-Generating Capacity of the Jaw-Closing Muscles in Man," Arch. Oral. Biol. 41:12, 1161-1168 (1996).
Makki, A, et. Al., Eds., A Dictionary of American Idioms, 4th Ed. Barron's, New York (2004), 342-343.
Markovitz, H., et al. "Calculations of Entanglement Coupling Spacings in Linear Polymers." Journal of Physical Chemistry, 1962. 66(8): 1567-1568.
McCrum, N., et al., Principles of Polymer Engineering. 2nd ed., New York: Oxford University Press 447(1997), Chapter 7, 296-351.
McGinity, J.W. et al., "Melt-Extruded Controlled-Release Dosage Forms" in Pharmaceutical Extrusion Technology, Ghebre-Sellassie, I. and Martin, C., Eds., Marcel Dekker Inc., New York, 2003, Chapter 10, 183-208.
McQuay, H. et a. "Methods, of Therapeutic Trials," Textbook of Pain 1125-1138 (P.D. Wall & R. Melzack eds., Elsevier 4th ed. 1999), Table of Contents and 1125-1138.
Miura et al., "Comparison of Maximum Bite Force and Dentate Status Between Healthy and Frail Elderly Persons," J. Oral Rehabilitation, vol. 28 (2001), pp. 592-595.
Miyagawa, Y. et al., "Controlled-release of diclofenac sodium from wax matrix granulate," Int '1 J. Pharmaceutics (1996) 138:215-224.
National Drug Intelligence Center Information Bulletin "OxyContin Diversion and Abuse" Jan. 2001.
Payne, H. et al., Denatonium Benzoate as a Bitter Aversive Additive in Ethylene Glycol and Methanol-Based Automotive Products, SAE Technical Paper 930589, Abstract (1993).
Pilpel, N., et al. "The effect of temperature on the tensile strength and disintegration of paracetamol and oxytetracylcine tablets," J Pharm Pharmac., 29:389-392 (1977).
Polyox Water-Soluble Resins NF in Pharmaceutical Applications, Dow Chemical Company, Aug. 2002.
Purdue Pharma LP Material Safety Data Sheet, OxyContin Tablets, 10 mg, 15 mg, 20 mg, 30 mg, 40 mg, 60 mg, Version Sep. 16, 2010; available at www.purduephruma.com/msdss/oxycontin_msds.pdf.

(56) References Cited

OTHER PUBLICATIONS

Rauwendaal, Chris, PhD, Responsive Expert Report of Chris Rauwendaal, Ph.D. Regarding Expert Report of Michael M. Crowley, Ph.D., dated Jul. 17, 2015.
Repka, M. et al. Pharmaceutical Applications of Hot-Melt Extrusion: Part II. Drug Dev. & Indus. Pharmacy (2007) 33:1043-1057.
Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.
Seitz, J.A.; et al., "Evaluation of the Physical Properties of Compressed Tablets 1: Tablet Hardness and Friability," J. of Pharm. Sci. , 54:1353-1357 (1965).
Shah, et al., "Some Effects of Humidity and Heat on the Tableting Properties of Microcrystalline Cellulose Formulations 1 ," J. of Pharm. Sci., 57:181-182 (1967).
Singhal, et al., Handbook of Indices of Food Quality and Authenticity (1997), "Capsicum" p. 398-299.
Smith, K.L. et al. "High Molecular Weight Polymers of Ethylene Oxide—Plastic Properties." Industrial and Engineering Chemistry, 1958. 50(1): 12-16.
Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review.pdf.
Tiwari, D., et al., "Evaluation of polyoxyethylene homopolymers for buccal bioadhesive drug delivery device formulations." AAPS Pharmsci, 1999. 1(3): Article 13.
Wilkins, J.N., "Pharmacotherapy of Schizophrenia Patients with Comorbid Substance Abuse," Schizophrenia Bulletin, 23:215-228 (1997).
World Health Org., Cancer Pain Relief With a Guide to Opioid Availability (2d ed. 1996).
Yin, T.P., et al., "Viscoelastic Properties of Polyethylene Oxide in Rubber-Like State." Journal of Physical Chemistry, 1961. 65(3): 534-538.
Zacny, J. et al. Drug & Alcohol Dependence (2003) 69:215-232.
Zhang, F., "Hot-Melt Extrusion as a Novel Technology to Prepare Sustained-Release Dosage Forms," Dissertation University of Texas at Austin, Dec. 1999.
Evekeo, (Amphetame Sulfate) for treating patients with ADHD website ([online] https://www.evekeo.com.about-evekeo; 2019:5 pages), 2019.
Lurie et al., "Chiral Resolution of Cationic Drugs of Forensic Interest," (Analytical Chemistry 1994; 66(22): 4019-4026.
U.S. Appl. No. 60/287,509, filed Dec. 2, 2002, Joshi et al.
U.S. Appl. No. 60/288,211, filed Sep. 2, 2004, Oshlack et al.
U.S. Appl. No. 60/310,514, filed Apr. 3, 2003, Oshlack et al.
U.S. Appl. No. 60/310,534, filed Apr. 10, 2003, Wright et al.
U.S. Appl. No. 60/376,470, filed Jan. 15, 2004, Ayer et al.
U.S. Appl. No. 60/384,442, filed Dec. 4, 2003, Fink et al.
2.9 Methoden der pharmazeutischen Technologie, European Pharmacopeia, 143-144, 1997. (Full English translation attached).
Albertini, B. "New spray congealing atomizer for the microencapsulation of highly concentrated solid and liquid substances" European Journal of Pharmaceutics and Biopharmaceutics 69 (2008) 348-357.
Alekseeva et al, Chemical-Pharmaceutical Journal, vol. 41, No. 9, 2007, 49-52. (Full translation attached.).
Almeida, A. et al., Ethylene vinyl acetate as matrix for oral sustained release dosage forms produced via hot-melt extrusion, European Journal of Pharmaceutics and Biopharmaceutics 77 (2011) 297-305.
Almeida, A. et al., Sustained release from hot-melt extruded matrices based on ethylene vinyl acetate and polyethylene oxide, European Journal of Pharmaceutics and Biopharmaceutics 82 (2012) 526-533.
Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.

Apicella A.et al., Biomaterials, vol. 14, No. 2, pp. 83-90,1993.
Application of a modelling system in the formulation of extended release hydrophilic matrices, Reprinted from Pharmaceutical Technology Europe, Jul. 2006.
Application of Opadry II, complete film coating system, on metformin HCl extended release matrices containing Polyox water soluble resin, Colorcon Apr. 2009.
Arnold C., "Teen Abuse of Painkiller OxyContin on the Rise," www.npr.org, Dec. 19, 2005.
Augustine, R.L., Catalytic Hydrogenation of a, B-Unsaturated Ketones. III the Effect of Ouantity and Type of Catalysts, J.Org Chem. 28(1), pp. 152-155, Abstract 1963.
Avis, Kenneth, Parenteral Preparations. Chapter 85. pp. 1518-1541in Remington's Pharmaceutical Sciences, 17th Ed, 1985.
Bailey, F.E., et al., "Some properties of poly(ethylene oxide) in aqueous solution," Journal of Applied Polymer Science, vol. 1, Issue No. 1, pp. 56-62, 1959.
Bannwarth, Bernard, "Will Abuse-Deterrent Formulations of Opioid Analgesics be Successful in Achieving Their Purpose?", Drugs, 2012, vol. 72, pp. 1713-1723.
Bauer et al. Lehrbuch der Pharmazeutischen Technologie. Eight Edition 2006. Stuttgart, pp. 343-352.
Bauer et al. Lehrbuch der Pharmazeutischen Technofogie. Sixth Edition 1999. Stuttgart, pp. IX-XV, Table of contents. (Full English translation attached).
Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al.,"The impact of the addition of naloxone on the use and abuse of pentazocine", Public Health Reports, Jul.-Aug. 1987, vol. 102, No. 4, p. 426-429.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology," Food Research International 88 (2016) 191-198.
Bingwen et al, 2008, p. 367. (full translation attached).
Block, Lawrence. Medicated Applications. Chapter 88. In Remington's Pharmaceutical Sciences, 17th Ed, 1985.
Borquist et al., "Simulailon of the release from a multiparticulate system validated by single pellet and dose release experiements," J. Controlled Release, 97: 453-465 (2004).
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Bruce et al, Properties of hot-melt extuded tablet formulations for the colonic delivery of 5-aminosalicylic acid, European Journal of Pharmaceutics and Biopharmaceutics, 59 (2005) 85-97.
Caraballo, Journal of Controlled Release, vol. 69, pp. 345-355, 2000.
Carbopol 71G, retrieved Mar. 10, 2014 from http://www.lubrizol.com/LifeScience/Products/Carbdpol71G-NF.html.
Cawello, "Parameters for Compartment-free Pharmacokinetics—Standardization of Study Design, Data Analysis and Reporting" 1999, pp. XI-XIII (table of contents).
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.
Committee for Proprietary Medicinal Products. Note for Guidance on the Investigation of Bioavailability and Bioequivalence. 2001. pp. 1-18.
Coppens et al., "Hypromellose, Ethylcellulose, and Polyethylene Oxide Use in Hot Melt Extrusion"; Pharmaceutical Technology, 62-70, Jan. 2005.

(56) References Cited

OTHER PUBLICATIONS

Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-melt extrusion," Biomaterials 23, 2002, pp. 4241-4248.
Crowley MM, Drug Dev Ind Pharm, Sep. 2007; 33(9):909-26. (Abstract only).
Cuesov, Drug Production Technology, Khar'kov, 1999, pp. 351-352. (Full translation attached.).
Dabbagh, et al. "Release of Propranolol Hydrochloride from Matrix Tablets Containing Sodium Carboxymethylcellulose and Hydroxypropylmethylcellulose"; 1999; Pharmaceutical Development and Technology, 4(3), 313-324.
Dachille et al., "High-pressure Phase Transformations in Laboratory Mechanical Mixers and Mortars", Nature, vol. 186, Apr. 2, 1960, pp. 34 and 71.
Dachille F. et al., "High-pressure Phase Transformations in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
De Brabander C., et al., "Development and evaluation of sustained release mini-matrices prepared via hot melt extrusion," Journal of Controlled Release 89 (2003), 235-247.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Definition Granule, Merriam-Webster, accessed online Jun. 28, 2018 (2018).
Deighan, C.J. et al., Rhabdomyolysis and acute renal failure resulting from alcohol and drug abuse, Q.J. Med, vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only).
Dierickx et al., "Co-extrusion as manufacturing technique for fixed-dose combination mini-matrices," European Journal of Pharmaceutics and Biopharmaceutics 81 (2012), 683-689.
Disanto, Anthony. Bioavailability and Bioequivalency Testing. Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
Dow Technical Data, Polyox WSR Solid Dosage Formulation via Melt Extrusion, Feb. 2003, pp. 1-3.
Efentakis et al, Effects of Excipients on Swelling and Drug Release from Compressed Matrices, in Drug Development and Industrial Pharmacy 23(1):107-112, Jan. 1997, Abstract.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
Eggleston, "The seat of the emetic action of various drugs," J. Pharmacol. Exp. Ther. 7, 225-253 (1915).
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogeles", European Polymer Journal, vol. 41 pp. 2584-2591, 2005.

Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde. Quality Assurance and Control, Chapter 83. pp. 1487-1491 in Remington's Pharmaceutical Sciences, 17th Ed, 1985.
Eudragit NE40D web page from Evonik website, downloaded Feb. 24, 2015.
Eudragit RS PO web page from Evonik website: downloaded Feb. 24, 2015.
European Pharmacopeia 5.0; Glyceryl behenate monograph; dated Jan. 2005; downloaded Feb. 24, 2015.
European Pharmacopoeia 2.9.40 "Uniformkof Dosage Units", 2006, pp. 3370-3373.
European Pharmacopoeia 3.0, 2.9.8 "Resistance to Crushing of Tablets", 1997, p. 135.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition Council of Europe, Strasbourg, 1997, pp. 127-152.
European Search Report and Opinion Application No. 12002708. 1-1219, dated Sep. 24, 2012.
European Search Report and Opinion Application No. 14176277. 3-1460, dated Dec. 15, 2014.
European Search Report and Opinion, Application No. 11006253. 6-2112, dated Dec. 16, 2011.
European Search Report and Opinion, Application No. 11006253. 4-2112, dated Dec. 16, 2011.
European Search Report and Opinion, Application No. 11008131. 2-1219, dated Feb. 24, 2012.
European Search Report and Opinion, Application No. 11009129. 5-2112, dated Apr. 10, 2012.
European Search Report and Opinion, Application No. 12001296. 8-1219, dated Jun. 26, 2012.
European Search Report and Opinion, Application No. 12001301. 6-1219, dated Jun. 26, 2012.
European Search Report and Opinion, Application No. 12003743. 7-1219, dated Sep. 24, 2012.
European European Search Report and Opinion for EP Application No. 14169801.9-1455, dated Oct. 20, 2014.
European European Search Report and Opinion for EP Application No. 13425151.1-1460, dated Mar. 11, 2014.
European European Search Report and Opinion for EP Application No. 13197503.9-1460, dated Feb. 18, 2014.
European European Search Report and Opinion for EP Application No. 13176309.9-1460, dated Oct. 9, 2013.
European European Search Report and Opinion for EP Application No. 13169658.5, dated Aug. 6, 2013.
European European Search Report and Opinion for EP Application No. 13169659.3, dated Aug. 6, 2013.
Evaluation of Verapamil HCl (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).

(56) References Cited

OTHER PUBLICATIONS

Evonik Rohm GmbH product brochure: Eudragit acrylic polymers for solid oral dosage forms (2009).
Extended European Search Report for Application No. EP 16182124.4-1455, dated Jan. 17, 2017.
Extended European Search Report for Application No. EP 16183922.0-1460, dated Oct. 31, 2016.
Extended European Search Report and Opinion for Application No. EP 15184634.2-1455, dated Mar. 3, 2016.
Extended European Search Report and Opinion for Application No. EP 15165064.5-1455, dated Oct. 16, 2015.
Extended European Search Report and Opinion for Application No. EP 15165065.2-1455, dated Nov. 2, 2015.
Extended European Search Report and Opinion for Application No. EP 15165067.8-1455, dated Nov. 2, 2015.
Extended European Search Report and Opinion for Application No. EP 15165069.4-1455, dated Nov. 2, 2015.
Extended European Search Report and Opinion for Application No. EP 15165070.2-1455, dated Nov. 2, 2015.
Extended European Search Report and Opinion for Application No. EP 15153679.4-1455, dated Jun. 30, 2015.
Fathima, N. et al. "Drug-excipient interaction and its importance in dosage form development," Journal of Applied Pharmaceutical Science 01 (06); 2011, pp. 66-71.
Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing, high loadings of freely soluble drugs," Drug Development and Industrial Pharmacy, 20(8), pp. 1323-1339, 1994.
Follonier, N. et al., "Various ways of modulating the release of dltiazem hydrochloride from hot-melt extruded sustained release pellets prepared using polymeric materials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Furu et al. "use of ADHD drugs in the Nordic countries: a population-based comparison study," Acta Psychiatrica Scandinavia, May 2010.
Giles R. et al. Plastic Packaging Materials. Chapter 81. pp. 1473-1477 in Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.
Handbook of Pharmaceutical Excipients, 1986, American Pharmaceutical Association, Washington, DC and London (Table of Content Only).
Handbuch der Kunststoff-Extrusionstechnik 1, "Grundlagen" in Chapter 1.2 "Klassifizierung von Extrudern", pp. 3-7. 1989. (Full english translation attached).
Hanning C.D. et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release. 2001, vol. 75, pp. 391-400.
Hoepfner et al. Fiedler Encyclopedia of Excipients, Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Houston, T.E., et al., "Bite Force and Bite Pressure: Comparison of Humans and Dogs," http://www.glapbta.com/BFBP.pdf, 2003, pp. 1-7.
Inert gas—Wikipedia, Dec. 2009, pp. 1-3.
Investigation of a Directly Compressible Metformin HCl 500mg Extended Release Formulation Based on Hypromellose, Colorcon Jul. 2009.
James, A. "The legal and clinical implications of crushing tablet medication", Nurse Times 100(50), 28-33, 2004.
Janicki S. et al. "Slow-Release Microballs: Method of Preparation", Acta Pharm. Technol. 33 (3) 154-155, 1987.
Jannetto, P. et al, "Oxycodone: Recognition and Pharmacogenomics," Toxicology News, Mar. 2003, 1-7.
Kalant H. et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).
Kim C.-J. "Drug Release from Compressed Hydrophilic Polyox-WSR Tablets" J Pharm. Sciences 1995, 84(3): pp. 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull. 1992, 40(10), 2800-2804.
King et al. Oral Solid Dosage Forms. Chapter 90. pp. 163-1632 in Remington's Pharmaceutical Sciences, 17th Ed, 1985.
King, R, "Tablets, Capsules, and Pills" Remington's Pharmaceutical Sciences, pp. 1553-1593, Ch. 89, 1980, $16^{th}$ Edition.
King, Remington's Pharmaceutical Sciences 17th ed., Chapter 78, p. 1418-1419 (1985).
Knevel, Adelbert. Separation. Chapter 78. pp. 1432-1442 in Remington's Pharmaceutical Sciences, 17th Ed, 1985.
Kolter, K., "Compression Behaviour of Kollidon SR," APV/ APGI 2002, Florence, Apr. 11, 2002.
Kondrat, T. , "Technology dosage forms" Moscow 1991, p. 96.
Koziolek, M. et al., "Development of a bio-relevant dissolution test device simulating mechanical aspects present in the fed stomach," European Journal of Pharmaceutical Sciences 57 (2014) 250-256.
Lee, Y.-S. et al., Principles of Terahertz Science and Technology (Lecture Notes in Physics), Springer; 1 edition 2008. (Table of Contents Only).
Lenindzer, A., "The molecular basis of the structure and functions of cells" Moscow 1974, p. 68.
Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.

(56) References Cited

OTHER PUBLICATIONS

Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded, 1990. vol. 2 (Cover and Table of Content only).
Lintner, Carl. Stability of Pharmaceutical Products. Chapter 82. pp. 1478-1486 in Remington's Pharmaceutical Sciences, 17th Ed, 1985.
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharmaceuticals and Health Care Products"; Blackie Academic & Professional; First Edition 1996. (Table of contents only).
Longer et al. Sustained-Release Drug Delivery Systems. Chapter 92. pp. 1611-1661 in Remington's Pharmaceutical Sciences, 17th Ed, 1985.
M. Xu et al., "Evaluation of the coat quality of sustained release pellets by individual pellet dissolution methodology," Int. J. Pharm. 478 (2015) 318-327.
Madorsky S.L. "Thermal degradation of Polyethylene Oxide and Polypropylene Oxide", Journal of Polymer Science, pp. 183-194, vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C.. Therapeutic Potential of Capsaicin-like Molecules. Life Sciences, vol. 51, pp. 1777-1781, 1992.
Mank R. et al., "Darstellung wirkstoffhaltiger Extrusionsformlinge auf der Basis von Thermoplasten. Teil 1: Untersuchung zur Wirkstoffliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2: Unersuchungen zur Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
McGary, C.W.. Jr. "Degradation of Poly(ethylene Oxide)", Journal of Polymer Science vol. XLVI,1960, pp. 51-57.
McGinity et al., Hot-Melt Extiusion as a Pharmaceutical Process, American Pharmaceutical Review, vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-963.
Mesiha M.S. et al "A Screening Study of Lubricants in Wet Powder Passes Suitable for extrusio-spheronization", Drug Development and Industrial Pharmacy, 19(8), pp. 943-959, 1993.
Metformin Hydrochloride 1000 mg Extended Release Tablets, Lubrizol Advanced Materials, Inc., Nov. 20, 2009, Previous Edition Dec. 19, 2008.
Metformin Hydrochloride 750 mg Extended Release Tablets, Lubrizol Advanced Materials, Inc., Sep. 2010.
Meyer et al., "Awareness Topic: Mitigating the Risks of Ethanol Induced Dose Dumping from Oral Sustained/Controlled Release Dosage Forms." FDA ACPS Meeting, Oct. 2005, p. 1-4.
Miles, R.E. et al., Terahertz Frequency Detection and Identification of Materials and Objects (NATO Science for Peace and Security Series B: Physics and Biophysics), Springer; 1 edition 2007. (Table of contents).
Miller "To crush or not to crush? What to consider before giving medications to a patent with a tube or who has trouble swallowing", Nursing, pp. 50-52, Feb. 2000.
Mises à jour cumulatives, Vidal, Jan./Oct. 2002 (full translation attached).
Mitchell, "Oral Dosage Forms That Should not be Crushed: 2000 Update" Hospital Pharmacy 35(5), 553-557, 2000.
Monolithic: retrieved from internet: http:/merriam-webster.com/dictionary/monolithic. Retrieved on Sep. 2, 2015.
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
Morissette et al. Advanced Drug Delivery Review 26 (2004), 275-300.
Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations. Chapter 87. pp. 1553-1563; in Remington's Pharmaceutical Sciences, 17th Ed, 1985.
Munjal M. et al., "Polymeric Systems for Amorphous Delta$^\wedge$9 -Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, in Remington's Pharmaceutical Sciences, 17th Ed, 1985.
Nickerson, B., Sample Preparation of Pharmaceutical Dosage Forms, Springer, New York (2011); Chapter 1, pp. 3-48.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.
Oliveira et al., "Production and characterization of laminar coextrudates at room temperature in the absence of solvents," AAPS Annual Meeting and Exposition, Oct. 14-18, 2012, Chicago, USA.
Oxicotin: Balancing Risks and Benefits, United States Senate, Hearing, Feb. 12, 2002.
Oxycodon (Oxygesic): Missbrauch, Abhaengigkeit und toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.
Ozeki T. et al. "Controlled Release From Solid Dispersion Composed of Poly(ethylene oxide)-Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviylpolymer interpolymer complex by varying molecular wight of poly(ethylene oxide)" Journal of Controlled Release 58, pp. 87-95, 1999.
Patel, et. al., "Poloxamers: A pharmaceutical excipient with therapeutic behaviors," PharmTech. vol. 1, No. 2, pp. 299-300 (Apr. 2009).
PCT International Search Report and Written Opinion for PCT Application No. PCT/EP2016/052046 dated Apr. 12, 2016.
PCT International Search Report and Written Opinion for PCT Application No. PCT/EP2017/070396 dated Sep. 8, 2017.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT International Search Report and Written Opinion for PCT Application No. PCT/EP2010/004459 dated Dec. 1, 2010.

(56) References Cited

OTHER PUBLICATIONS

PCT International Search Report and Written Opinion for PCT Application No. PCT/EP2013/053894 dated Mar. 22, 2013.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 22, 2015.
PCT International Search Report and Written Opinion for PCT Application No. PCT/EP2014/064830 dated Aug. 6, 2014.
PCT International Search Report and Written Opinion for PCT Application No. PCT/EP2009/003290 dated Jul. 9, 2009.
PCT International Search Report and Written Opinion for PCT Application No. PCT/EP2013/059728 dated Aug. 6, 2013.
PCT International Search Report and Written Opinion for PCT Application No. PCT/EP2013/057851 dated Jun. 12, 2013.
PCT Second Written Opinion for PCT Application No. PCT/EP2013/057851 dated Apr. 15, 2014.
PCT Second Written Opinion for PCT Application No. PCT/EP2013/053893 dated Feb. 21, 2014.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Sep. 1989, 6(9), S-98.
Pharm. Research, Official Journal of the American Association of Pharmaceutical Scientists, Oct. 1991, 8(10), S-192.
Pharma Tips ([online] retrieved on Mar. 22, 2018 from http://ww.pharmatips.in/Articles/Pharmaceutics/Tablet/Co-Processed-Directly-Compressed-Adjutants.aspx; May 2011: 10 pages).
Phillips, G. Briggs. Sterilization. Chapter 79. pp. 1443-1454, in Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system. Journal of Controlled Release. 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008. (Table of Contents only).
Polyox water soluble resins 2003. http://www.dow.com/webapps/lit/litorder.asp?filepath=polyox/pdfs/noreg/326-00002.pdf.
Polyox water-soluble resins (Dow Mar. 2002); see http://msdssearch.dow.com/PublishedLiteratureDOWCOM/dh_0031/0901b80380031a4a.pdf?filepath=/326-00001.pdf&fromPage=GetDoc).
Polyox Water-Soluble Resins in Pharmaceutical Applications. Dow Chemicals. Published 2004.
Polyox WSR-303, retrieved Mar. 10, 2014 from URL http://www.dow.com/dowwolfffen/industrial_solutions/polymers/polyethylene.
Polyox, Colorcon, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Porter, S. Coating of Pharmaceutical Dosage Forms, Chapter 91. pp. 1633-1643 in Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs as First Priority; New Drug Application Delayed," www.headaches.about.com, Jun. 18, 2002, pp. 1-6.
Quadros, E. et al., "Evaluation of a novel colonic delivery device in vivo," STP Pharma Sci. 5, 77-82 (1995).
Quintavalle et al., "Preparation of sustained release co-extrudates by hot-melt extrusion and mathematical modelling of in vitro/in vivo drug release profiles," European Journal of pharmaceutical Sciences 33 (2008), 282-293.
Radko S.et al., Applied ad Theoretical Electrophoresis 5, pp. 79-88, 1995.
Ravin, L. Preformulation. Chapter 76, pp. 1409-1423, in Remington's Pharmaceutical Sciences, 17th Ed, 1985.
Remington, Chapter 45, pp. 996-1035. (2000) (Full Translation Attached) [76 Examiner rewrote as Rudnic et al, Ramington Farmacia, Medica Panamencana, Cpt. 45, pp. 996-1035 (2003).
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka, "Pharmaceutical applications of hot-melt extrusion," MA, Drug Dev Ind Pharm. Oct. 2007; 33(10):1043, (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippie, E. Powders. Chapter 89, pp. 1585-1602, in Remington's Pharmaceutical Sciences, 17th Ed, 1985.
Ritschel et al. Die Tablette: Handbuch der Entwicklung, Herstellung und Qualitatssicherung. 2nd Edition, 2002, Ch 6, pp. 515-519. (Full English translation attached).
Ritschel et al. Die Tablette: Handbuch der Entwicklung, Herstellung und Qualitatssicherung. 2nd Edition, 2002, Ch 6, pp. 69-82 and 115-136.
Ritschel et al. Die tablette: Handbuch der Entwicklung, Herstellung und Qualitatssicherung. 2nd Edition, 2002, Table of content.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013), pp. 1250-1258.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Saleem et al. "Formulation and Evaluation of Tramadol hydrochloride Rectal Suppositories," Indian J. Pharm Sci. Sep.-Oct. 2008; 70(5), 640-644.
Salomies et al., "Determination of Oxycodone Hydrochloride in Oral Solutions by High-Performance Thin-Layer Chromatography/Densitometry," Journal of AOAC International, 83: 1497-1501 (2004).
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Sax et al., Hawley's Condensed Chemical Dictionary, 11th ed., 1987, p. 1233, definition of "wax".
Scheirs J., et al."Characterizing the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended-Release Nifedipine" the Annals of Pharmacotherapy vol. 37, 1420-1423, Oct. 2003.
Schilling, et al., "Novel application of hot-melt extrusion for the preparation of monolithic matrices containing enteric-coated particles." International Journal of Pharmaceutics 400 (2010) 24-31.

(56) References Cited

OTHER PUBLICATIONS

Schroeder J., et al. Granulierung hydrophober Wirkstoffe im Planetwalzenextruder, Pharm. Ind. 2003, vol. 65, No. 4, 367-372, (Full English translation attached).
Sciarra et al. Aerosols. Chapter 93., pp. 1662-1677, in Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCl From Melt extruded Polyethylene Disks", Pharmaceutical Research, Oct. 1991, vol. 8, No. 10, p. S-192.
Sidhu et al., "Watch for nonpsychotropics causing psychiatric side effects," Current Psychiatry, vol. 7, No. 4, 2008, 61-74.
Siegel, P. Tonicity, Osmoticity, Osmolality, and Osmolarity. Chapter 80. pp. 1454-1472 in Remington's Pharmaceutical Sciences, 17th ed, 1985.
Sigma-Aldrich entry for CAS No. 9010-88-2; www.sigmaaldrich.com/catalog/product/aldrich/182249?lang=en&region=US (downloaded Jun. 2018).
Silver, J. "Painkiller OxyContin" most commonly abused prescription drug on the streets of Western Pennsylvania, Pittsburg Post-Gazette, Apr. 8, 2001.
Spassov et al., Stereochemistry of Diastereomeric 3-Dialkylaminopropanols and O-Derivatives, J.f. prakt. Chemie, 323:5, 793-800 (1981).
Sprockel O.L et al. "Permeability of Cellulose Polymers: Water Vapour Transmission Rates"., J. Pharma. Pharmacol. 42, pp. 152-157, 1990.
Sprockel, et. al, "A melt-extrusion process for manufacturing matrix drug delivery systems," Int. Journal of Pharmaceutics 155 (1997) 191-199.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., Überzogene feste Formen, 1991, 347-68, (English translation attached).
Starch 1500, Partially Pregelatinized Maize Starch, technical data from Colorcon, Feb. 2016, 6 pages.
Strang, Abuse of buprenorphie (Temgesic) by snorting, Letter to the editor, British Med. J., 302: 969 (1991).
Stringer J. L., et al "Diffusion of small molecular weight drugs in radiation-crosslinked poly(ethyleneoxide) hydrogels", Journal of Controlled Release 42, pp. 195-202, 1996.
Sumitomo Seika Chemicals, Co., Ltd, "Certificate of Analysis," Product: Polyethylene Oxide; Grade: PEO-18NF; Feb. 2, 2016.
Sumitomo Seika Chemicals, Co., Ltd, "Certificate of Analysis," Product: Polyethylene Oxide; Grade: PEO-20NF; Feb. 3, 2016.
Sumitomo Seika Chemicals, Co., Ltd, "Certificate of Analysis," Product: Polyethylene Oxide; Grade: PEO-20NF; Jan. 23, 2012.
Sumitomo Seika Chemicals, Co., Ltd, "Certificate of Analysis," Product: Polyethylene Oxide; Grade: PEO-20NF; May 15, 2013.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).
Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opiolds; 7 pages.
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Theeuwes, Felix et al., Osmotic Systems for Colon-Targeted Drug Delivery in Colonic Drug Absorption and Metabolism (Peter R. Bieck ed., 1993).
Third Party Observations filed with EPO for Patent EP658055B1, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr. 3, 1989.
Tikhonov, A. et al, Biopharmacy. The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra-low-dose natrexone" Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86, pp. 1542-1552, in Remington's Pharmaceutical Sciences, 17th Ed, 1985.
Turkington, R., "Amphetamines," in Chemicals used for Illegal Purposes. A Guide for first Responders to Identify Explosives, Recreational Drugs, and Poisons, 2010, p. 247.
US Pharmacopoeia, Chapter 1217, Aug. 12, 2008.
USP Expert Council, US Pharmacopoeia, Chapter 1092, 2007, 1-15.
Varma et al, Factors Affecting Mechanism and Kinetics of Drug Release from Matrix-Based Oral Controlled Drug Delivery Systems, Am. J. Drug Deilv. 2004:2 (1): 43-57.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.

(56) References Cited

OTHER PUBLICATIONS

Vezin, W. et al, "Adjustment of precompression force to reduce mixing-time dependence of tablet tensile strength," J. Pharm. Pharmacol. 1983, 35: 555-558 (Mar. 28 1983).
Vippagunta et al. Crystalline Solids, Advanced Drug Delivery Review 48 (2001), 3-26.
Vynckier et al.,"Hot-melt co-extrusion for the production of fixed-dose combination products with a controlled release ethylcellulose matrix core," International Journal of Pharmaceutics 464 (2014), 65-74.
Wade and Weller, "Handbook of Pharmaceutical Excipients: 2nd Edition", the American Pharmaceutical Association and the Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart-N.Y., 1982, pp. 82-92 (Full English Translation attached).
Wagner, Pharmazeutische Biologie—Drogen und ihre Inhaltsstoffe—Scharfstoffdrogen, 2nd., revised edition, Gustav Fischer Verlag Stuttgart-N.Y., 1982,Table of Content.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", Acta Odontol Scand 53 (1995): 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 164(1): pp. 173-174 (2007).
Weiss, U., "Derivatives of Morphine. I 14-Dihydroxydihydromorphinone," J. Am. Chem, Soc. 77, pp. 5891-5892, Nov. 20, 1955.
West, Anthony R., Solid state chemistry and its applications, Wiley, New York, 1988, pp. 358 and 365.
Wikipedia-Dextromethorphan Aug. 12, 2013 (and attached related English-language entry dated Dec. 11, 2013).
Woodburn, K.R. et al., Vascular complications of injecting drug misuse, Br. J. of Surgery, vol. 83, 1996, pp. 1329-1334.
Wooten, Marvin R. et al., Intracerebral Hemorrhage and Vasculitis Related to Ephedrine Abuse, 13 Annals of Neurology 337 (1983).
Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar- and -pestle grinding on microstructure of sintered alumina gel", Nature 322, pp. 347-349 (Abstract only) (Jul. 24, 1986).
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmSciTech 11(2); 910-916 (available on-line May 22, 2010).
Zhang et al., "Properties of Sustained-Release Tablets Prepared by Hot-Melt Extrusion" Pharmaceutical Development and Technology, 1999, 4(2), 241-250.

Weinhold, et al. "Buprenorphine alone and in combination with naloxone in non-dependent humans." Drug & Alcohol Dependence 30.3 (1992): 263-274.
Thumma et al., "Influence of Plasticizers on the Stability of a Prodrug of D9-Tetrahydrocannabinol Incorporated in poly(Ethyelen Oxide) Matrices", Eur J. Pharm Biopharm. Oct. 2008 (70(2): 605-614.
Martin et al., "Applications of Polyethylene Oxide (Polyox) in Hydrophilic Matrices," in Hydrophilic Matrix Tablets for Oral Controlled Release, Springer, New York, 2014, Chapter 5, pp. 123-141.
Ely et al., "Lithium-Ammonia Reduction of Ephedrine to Methamphetamine: An Unusual Clandestine Synthesis," Technical Note, 1990, 720-723.
Kunalan et al., "Investigation of the Reaction Impurities Associated with Methylamphetamine Synthesized using the Nagai Method," Anal. Chem. 2012, 84, 5744-52.
Jedinger, N., et al., Eur. J. Pharm. Biopharm 87 (2014), 217-226.
Lee et al., "Analysis of the impurities in the metamphetamine synthesized by thee different methods from ephedrine and pseudoephedrine," Forensic Science International 161 (2006), 209-215.
Polyox, 2004, online retrieved on Oct. 15, 2018.
Person et al., Structural Determination of the Principal Byproduct of the Lithium-Ammonia Reduction Method of Methamphetamine Manufacture, J Forensic Sci, Jan. 2005, vol. 50, No. 1, 87-95.
Salouros et al., Isolation and Identification of Three By-Products Found in Methylamphetamine Synthesized by the Emde Route2010, 605-615.
Skinner, Harry F., "Methamphetamine Synthesis via Hydriodic Acid/Red Phosphorus Reduction of Ephedrine," Forensic Science International, 48 (1990), 123-134.
Hedaya, M. et al. "The Need for Tamper-Resistant and Abuse-Deterrent Formulations," J. Pharma Care Health Systems, vol. 1, Issue 1 (2014).
Gaitondf, B. "General Principles of Drug Action", 1967, p. 48.
Vosburg, et al., "A comparison among tapentadol tamper-resistant formulations (TRF) and OxyCotin® (non-TRF) in prescription opioid abusers," 2013; Society for the Study of Addiction; Addiction, vol. 108, pp. 1095-1106.
Lefnaoui et al., Synthesis and evaluation of the structural and physiochemical properties of carboxymethyl pregelatinized starch as a pharmaceutical excipient, Saudi Pharmaceutical Jourani, Feb. 2015:23:698-711 (2015).
Lopez-Solis et al., Effect of disintegrants with different hygroscopicity on dissolution of Norfloxacin/Pharmatose DCL 11 tablets, International Journal of Pharmaceutics 2001:216:127-135 (2001).
Domino E.F. (1991) Nicotine: A Unique Psychoactive Drug. In: Adlkofer F., Thurau K. (eds.) Effects of Nicotine on Biological Systems. APS Advances in Pharmacological Sciences. Birkhaeuser Basel (1991).
BASF the chemical company, Kollicoat IR Technical information, Feb. 2013, p. 1-14 (2013).
Befort et al., "The Conserved Asparatate Residue in the Third Putative Transmember Domain," Molecular Pharmacology 1996: 49:216-223 (1996).
Fitzpatrick, J., "The influence of Superdisintegrants on Immediate Release," by Pharmaceutical Technology Editions [online] retrieved from http://www.pharmatech.com/influence-superdisintegrants-immediate-release; vol. 21, issue 6 (Jun. 1, 2011).
Suzuki, T, "Blood-brain barrier transport of opioid analgesics," Abstract, Yakugaki Zasshi; 131(10):1445-51 (2011).
Kolar et al., "Treatmen of adults with attention-deficit/hyperactivity disorder," Neuropsychiatric Disease and Treatment 2008:4(3):389-403.
Rasmussen, N. "America's First Amphetamine Epidemic 1929-1971," American Journal of Public Health 2008:98(6): 974-985.
Heal et al. "Amphetamine, past and present—a pharmacological and clinical perspective," Journal of Psychology 2013:27(6):479-496 (2013).
Nagar et al., "Orally disintegrating tablets : formulation, preparation techniques and evaluation," Journal of Applied Pharmaceutical Science 2011, 01(04): 35-45 (2011).

(56) References Cited

OTHER PUBLICATIONS

Mastropietro, D. et al. "Current approaches in tamper-resistant and abuse-deterrent formulations." Drug Development and Industrial Pharmacy, vol. 39(5), pp. 611-624 (2013).
Pintauro, Nicholas, D., Food Flavoring Processes, Table of Content. Park Ridge, NJ and London, UK, 1976.
European Pharmacopeia, 7th Ed. 2.2.8 and 2.2.10, 27ff. (2010).

TAMPER-RESISTANT TABLET PROVIDING IMMEDIATE DRUG RELEASE

PRIORITY

This application is a division of U.S. Nonprovisional patent application Ser. No. 13/559,644, filed Jul. 27, 2012, now allowed, which claims priority of U.S. Provisional Patent Application No. 61/512,943 filed on Jul. 29, 2011, and European Patent Application No. 11 006 254.4 filed on Jul. 29, 2011, the contents of both of which patent applications are incorporated herein by reference.

FIELD OF THE INVENTION

The invention relates to tamper-resistant tablets comprising a matrix material and a plurality of coated particulates which comprise a pharmacologically active compound and form a discontinuous phase within the matrix material, preferably providing under in vitro conditions immediate release of the pharmacologically active compound.

BACKGROUND OF THE INVENTION

A large number of pharmacologically active substances have a potential for being abused or misused, i.e. they can be used to produce effects which are not consistent with their intended use. Thus, e.g. opioids which exhibit an excellent efficacy in controlling severe to extremely severe pain, are frequently abused to induce euphoric states similar to being intoxicated. In particular, active substances which have a psychotropic effect are abused accordingly.

To enable abuse, the corresponding dosage forms, such as tablets or capsules are crushed, for example ground by the abuser, the active substance is extracted from the thus obtained powder using a preferably aqueous liquid and after being optionally filtered through cotton wool or cellulose wadding, the resultant solution is administered parenterally, in particular intravenously. This type of dosage results in an even faster diffusion of the active substance compared to the oral abuse, with the result desired by the abuser, namely the kick. This kick or these intoxication-like, euphoric states are also reached if the powdered dosage form is administered nasally, i.e. is sniffed.

Various concepts for the avoidance of drug abuse have been developed.

It has been proposed to incorporate in dosage forms aversive agents and/or antagonists in a manner so that they only produce their aversive and/or antagonizing effects when the dosage forms are tampered with. However, the presence of such aversive agents is principally not desirable and there is a need to provide sufficient tamper-resistance without relying on aversive agents and/or antagonists.

Another concept to prevent abuse relies on the mechanical properties of the pharmaceutical dosage forms, particularly an increased breaking strength (resistance to crushing). The major advantage of such pharmaceutical dosage forms is that comminuting, particularly pulverization, by conventional means, such as grinding in a mortar or fracturing by means of a hammer, is impossible or at least substantially impeded. Thus, the pulverization, necessary for abuse, of the dosage forms by the means usually available to a potential abuser is prevented or at least complicated.

Such pharmaceutical dosage forms are useful for avoiding drug abuse of the pharmacologically active compound contained therein, as they may not be powdered by conventional means and thus, cannot be administered in powdered form, e.g. nasally. The mechanical properties, particularly the high breaking strength of these pharmaceutical dosage forms renders them tamper-resistant. In the context of such tamper-resistant pharmaceutical dosage forms it can be referred to, e.g., WO 2005/016313, WO 2005/016314, WO 2005/063214, WO 2005/102286, WO 2006/002883, WO 2006/002884, WO 2006/002886, WO 2006/082097, WO 2006/082099, and WO2009/092601.

These dosage forms secured against abuse are distinguished by a controlled, preferably retarded release of the active substance which has abuse potential. However, a rapid release of the active substance is necessary for numerous therapeutic applications, for example pain relief using active substances with abuse potential.

WO 2010/140007 discloses dosage forms comprising melt-extruded uncoated particulates comprising a drug, wherein said melt-extruded particulates are present as a discontinuous phase in a matrix. The dosage forms provide prolonged release of the drug.

WO 2008/107149 discloses multiparticulate dosage forms with impeded abuse containing, one or more active substances having abuse potential, at least one synthetic or natural polymer, and at least one disintegrant, with the individual particles of the tablet having a breaking strength of at least 500 N and a release of the active substance of at least 75% after 45 minutes. The exemplified capsules provide rapid release of the pharmacologically active compound.

US 2010/0092553 and US 2007/224129 A1 disclose solid multiparticulate oral pharmaceutical forms whose composition and structure make it possible to avoid misuse. The microparticles have an extremely thick coating layer which assures the modified release of the drug and simultaneously imparts crushing resistance to the coated microparticles so as to avoid misuse.

WO 2008/033523 discloses a pharmaceutical composition that may include a granulate which may at least include one active pharmaceutical ingredient susceptible to abuse. The particle contains both an alcohol soluble and alcohol insoluble and at leasts partially water soluble material. Both materials are granulated in the presence of alcohol and water. The granulate may also include a coating on the granulate exhibiting crush resistance. Material deposition on the granule is performed using an alcohol based solvent.

The properties of capsules, however, are not satisfactory in every respect, e.g. with respect to disintegration time, patient compliance (e.g. swallowability) and ease of manufacture. Further, capsules frequently contain gelatine thus causing the risk of bovine spongiform encephalopathy (BSE, or TSE). As far as tamper-resistant dosage forms are concerned, capsules are disadvantageous as they can typically be opened easily thereby releasing the ingredients in powdery or particulate form without requiring any mechanical impact. If components of different type are contained in a capsule, e.g. drug-containing particles besides drug-free particles, a potential abuser might be able to visually distinguish the intact, undisrupted components of different type (e.g. according to their color, size or other macroscopic properties) allowing for manual separation.

The properties of these tamper-resistant dosage forms, however, are not satisfactory in every respect. There is a need for tamper-resistant dosage forms that possess crush resistance and release the pharmacologically active compound as quick as possible (immediate release), i.e. should show a gradual increase reaching 85% to 100% at about 30 to 45 minutes or earlier. The dosage form should advantageously be of a shape, size and weight that can be taken orally with ease. Of course, the dosage form should also be easy to make in a cost effective manner. When trying to tamper the dosage form in order to prepare a formulation suitable for abuse by intravenous administration, the liquid part of the formulation that can be separated from the remainder by means of a syringe should be as less as possible, e.g. should contain not more than 20 wt.-% of the pharmacologically active compound originally contained in the dosage form.

The manufacturing of functionally coated microparticles or granules, however, is not satisfactory with respect to the excessive manufacturing effort by applying the film-coating in an organic spraying procedure, which needs extensive measure to prevent vapor explosions. From an environmental and toxicological perspective the use of organic solvents is further undesirable. Furthermore, applying a functional film coat in general requires high efforts to assure the integrity of the functional barrier and is therefore a production step generating high manufacturing cost.

It is an object according to the invention to provide tamper-resistant pharmaceutical dosage forms that provide rapid release of the pharmacologically active compound and that have advantages compared to the tamper-resistant pharmaceutical dosage forms of the prior art.

This object has been achieved by the patent claims.

SUMMARY OF THE INVENTION

The invention relates to a tamper-resistant tablet, preferably for oral administration, comprising (i) a matrix material in an amount of more than one third of the total weight of the tablet; and (ii) a plurality of coated particulates in an amount of less than two thirds of the total weight of the tablet; wherein said particulates comprise a pharmacologically active compound and a physiologically acceptable polymer, preferably a polyalkylene oxide; and form a discontinuous phase within the matrix material;

which preferably provides under in vitro conditions immediate release of the pharmacologically active compound in accordance with Ph. Eur.

It has been surprisingly found that the in vitro release profile of tamper-resistant dosage forms can be accelerated by embedding particulates containing the pharmacologically active compound in a matrix material and increasing the relative weight ratio of the matrix material to the coated particulates.

Further, it has been surprisingly found that mixtures of matrix material, optionally in pre-compacted or pre-granulated form, can be mixed with the coated particulates and subsequently be compacted to tablets which in turn exhibit excellent, i.e. accelerated disintegration times and in vitro release characteristics.

Still further, it has been surprisingly found that oral dosage forms can be designed that provide the best compromise between tamper-resistance, disintegration time and drug release, drug load, processability (especially tablettability) and patient compliance.

In particular, it has been surprisingly found that disintegration and drug release can be accelerated when providing the particulates with a coating, preferably with a coating material comprising a water-soluble polymer. It has been unexpectedly found that the dissolution of said coating does not additionally impede disintegration and drug release, respectively, but causes a significant acceleration thereof.

BRIEF DESCRIPTION OF THE DRAWINGS

The invention will now be described in greater detail with reference to the drawings, wherein.

DETAILED DESCRIPTION OF THE INVENTION

Figure 1:
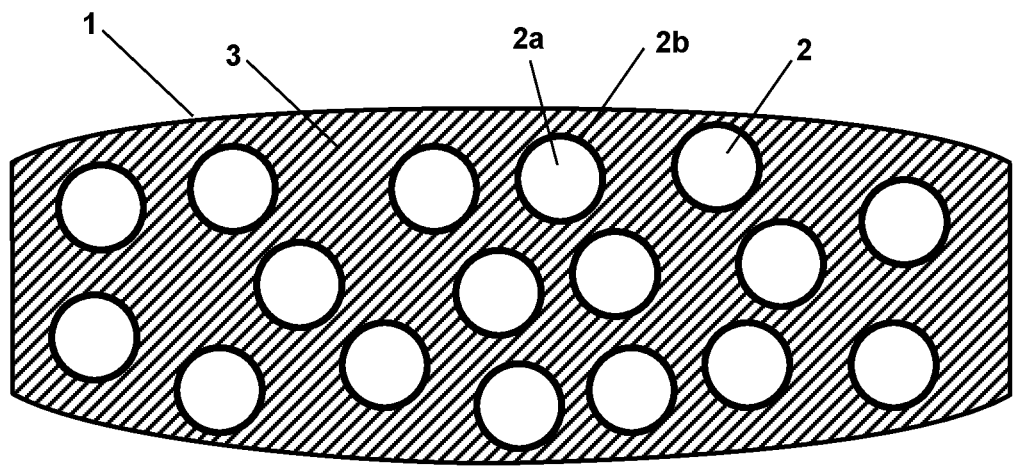
FIG. 1 schematically illustrates a preferred embodiment of the tablets according to the invention.

As used herein, the term "tablet" refers to a pharmaceutical entity that is comprised of a pharmacologically active compound and which is actually administered to, or taken by, a patient. It may be compressed or molded in its manufacture, and it may be of almost any size, shape, weight, and color. Most tablets are intended to be swallowed whole and accordingly, preferred tablets according to the invention are designed for oral administration. However, alternatively tablets may be dissolved in the mouth, chewed, or dissolved in liquid before swallowing, and some may be placed in a body cavity. Thus, the tablet according to the invention may alternatively be adapted for buccal, lingual, rectal or vaginal administration. Implants are also possible.

The tablet according to the invention preferably can be regarded as a MUPS formulation (multiple unit pellet system). In a preferred embodiment, the tablet according to the invention is monolithic. In another preferred embodiment, the tablet according to the invention is not monolithic. In this regard, monolithic preferably means that the tablet is formed or composed of material without joints or seams or consists of or constitutes a single unit.

Preferably, the tablet according to the invention contains all ingredients in a dense compact unit which in comparison to capsules has a comparatively high density.

The tablets according to the invention comprise subunits having different morphology and properties, namely drug-containing particulates and matrix material, wherein the coated particulates form a discontinuous phase within the matrix material. The coated particulates typically have mechanical properties that differ from the mechanical properties of the matrix material. Preferably, the coated particulates have a higher mechanical strength than the matrix material. The coated particulates within the tablets according to the invention can be visualized by conventional means such as solid state nuclear magnetic resonance spectroscopy, raster electron microscopy, terahertz spectroscopy and the like.

An advantage of the tablets according to the invention is that the same particulates may be mixed with matrix material in different amounts to thereby produce tablets of different strengths.

The tablet according to the invention has preferably a total weight in the range of 0.01 to 1.5 g, more preferably in the range of 0.05 to 1.2 g, still more preferably in the range of 0.1 g to 1.0 g, yet more preferably in the range of 0.2 g to 0.9 g, and most preferably in the range of 0.3 g to 0.8 g. In a preferred embodiment, the total tablet weight is within the range of 500±450 mg, more preferably 500±300 mg, still more preferably 500±200 mg, yet more preferably 500±150 mg, most preferably 500±100 mg, and in particular 500±50 mg.

It has been surprisingly found that the total tablet weight, which is a function of the total size of the tablet, can be optimized in order to provide the best compromise between tamper-resistance, disintegration time and drug release, drug load, processability (especially tablettability) and patient compliance.

In a preferred embodiment, the tablet according to the invention is a round tablet. Tablets of this embodiment preferably have a diameter in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

In another preferred embodiment, the tablet according to the invention is an oblong tablet. Tablets of this embodiment preferably have a lengthwise extension (longitudinal extension) of about 1 mm to about 30 mm, in particular in the range of about 2 mm to about 25 mm, more in particular about 5 mm to about 23 mm, even more in particular about 7 mm to about 20 mm; a width in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

The tablets according to the invention can optionally be provided, partially or completely, with a conventional coating. The tablets according to the invention are preferably film coated with conventional film coating compositions. Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), poly(meth)-acrylates, such as aminoalkylmethacrylate copolymers, methacrylic acid methylmethacrylate copolymers, methacrylic acid methylmethacrylate copolymers; vinyl polymers, such as polyvinylpyrrolidone, polyvinyl alcohol, polyvinylacetate; and natural film formers.

In a particularly preferred embodiment, the coating is water-soluble. In a preferred embodiment, the coating is based on polyvinyl alcohol, such as polyvinyl alcohol-part. hydrolyzed, and may additionally contain polyethylene glycol, such as macrogol 3350, and/or pigments. In another preferred embodiment, the coating is based on hydroxypropylmethylcellulose, preferably hypromellose type 2910 having a viscosity of 3 to 15 mPas.

The coating can be resistant to gastric juices and dissolve as a function of the pH value of the release environment. By means of this coating, it is possible to ensure that the tablet according to the invention passes through the stomach undissolved and the active compound is only released in the intestines. The coating which is resistant to gastric juices preferably dissolves at a pH value of between 5 and 7.5.

The coating can also be applied e.g. to improve the aesthetic impression and/or the taste of the tablets and the ease with which they can be swallowed. Coating the tablets according to the invention can also serve other purposes, e.g. improving stability and shelf-life. Suitable coating formulations comprise a film forming polymer such as, for example, polyvinyl alcohol or hydroxypropyl methylcellulose, e.g. hypromellose, a plasticizer such as, for example, a glycol, e.g. propylene glycol or polyethylene glycol, an opacifier, such as, for example, titanium dioxide, and a film smoothener, such as, for example, talc. Suitable coating solvents are water as well as organic solvents. Examples of organic solvents are alcohols, e.g. ethanol or isopropanol, ketones, e.g. acetone, or halogenated hydrocarbons, e.g. methylene chloride. Coated tablets according to the invention are preferably prepared by first making the cores and subsequently coating said cores using conventional techniques, such as coating in a coating pan.

As used herein, the term "tamper-resistant" refers to tablets that are resistant to conversion into a form suitable for misuse or abuse, particular for nasal and/or intravenous administration, by conventional means such as grinding in a mortar or crushing by means of a hammer. In this regard, the tablets as such may be crushable by conventional means. However, the coated particulates contained in the tablets according to the invention exhibit mechanical properties such that they cannot be pulverized by conventional means any further. As the coated particulates are of macroscopic size and contain the pharmacologically active compound, they cannot be administered nasally thereby rendering the tablets tamper-resistant. Preferably, when trying to tamper the dosage form in order to prepare a formulation suitable for abuse by intravenous administration, the liquid part of the formulation that can be separated from the remainder by means of a syringe is as less as possible, preferably it contains not more than 20 wt.-%, more preferably not more than 15 wt.-%, still more preferably not more than 10 wt.-%, and most preferably not more than 5 wt.-% of the originally contained pharmacologically active compound. Preferably, this property is tested by (i) dispensing a tablet that is either intact or has been manually comminuted by means of two spoons in 5 ml of purified water, (ii) heating the liquid up to its boiling point, (iii) boiling the liquid in a covered vessel for 5 min without the addition of further purified water, (iv) drawing up the hot liquid into a syringe (needle 21G equipped with a cigarette filter), (v) determining the amount of the pharmacologically active compound contained in the liquid within the syringe.

Further, when trying to disrupt the tablets by means of a hammer or mortar, the coated particulates may also, depending on the circumstances, tend to adhere to one another thereby forming aggregates and agglomerates, respectively, which are larger in size than the untreated coated particulates.

The subjects to which the tablets according to the invention can be administered are not particularly limited. Preferably, the subjects are animals, more preferably human beings.

In the tablets according to the invention, the coated particulates are incorporated into a matrix material. From a macroscopic perspective, the matrix material preferably forms a continuous phase in which the coated particulates are embedded as discontinuous phase.

Preferably, the matrix material is a homogenous coherent mass, preferably a homogeneous mixture of solid constituents, in which the coated particulates are embedded thereby spatially separating the coated particulates from one another. While it is possible that the surfaces of coated particulates are in contact or at least in very close proximity with one another, the plurality of coated particulates preferably cannot be regarded as a single continuous coherent mass within the tablet.

In other words, the tablet according to the invention comprises the coated particulates as volume element(s) of a first type in which the pharmacologically active compound and the physiologically acceptable polymer, preferably the polyalkylene oxide are contained, preferably homogeneously, and the matrix material as volume element of a second type differing from the material that forms the coated particulates, preferably containing neither pharmacologically active compound nor physiologically acceptable polymer, preferably no polyalkylene oxide, but optionally polyethylene glycol which differs from polyethylene oxide in its molecular weight.

A purpose of the matrix material in the tablet according to the invention is to ensure rapid disintegration and subsequent release of the pharmacologically active compound from the disintegrated tablets, i.e. from the coated particulates. Thus, the matrix material preferably does not contain any excipient that might have a retardant effect on disintegration and drug release, respectively. Thus, the matrix material preferably does not contain any polymer that is typically employed as matrix material in prolonged release formulations.

FIG. 1 schematically illustrates a preferred embodiment of the tablet according to the invention. Tablet (1) contains a plurality of coated particulates (2) having core (2a) and coating (2b) that form a discontinuous phase within matrix material (3) which in turn forms a continuous phase.

The tamper-resistant tablet according to the invention comprises the matrix material in an amount of more than one third of the total weight of the tablet.

It has been surprisingly found that the content of the matrix material in the tablet can be optimized in order to provide the best compromise between tamper-resistance, disintegration time and drug release, drug load, processability (especially tablettability) and patient compliance.

Preferably, the content of the matrix material is at least 35 wt.-%, at least 37.5 wt.-% or at least 40 wt.-%; more preferably at least 42.5 wt.-%, at least 45 wt.-%, at least 47.5 wt.-% or at least 50 wt.-%; still more preferably at least 52.5 wt.-%, at least 55 wt.-%, at least 57.5 wt.-% or at least 60 wt.-%; yet more preferably at least 62.5 wt.-%, at least 65 wt.-%, at least 67.5 wt.-% or at least 60 wt.-%; most preferably at least 72.5 wt.-%, at least 75 wt.-%, at least 77.5 wt.-% or at least 70 wt.-%; and in particular at least 82.5 wt.-%, at least 85 wt.-%, at least 87.5 wt.-% or at least 90 wt.-%; based on the total weight of the tablet.

Preferably, the content of the matrix material is at most 90 wt.-%, at most 87.5 wt.-%, at most 85 wt.-%, or at most 82.5 wt.-%; more preferably at most 80 wt.-%, at most 77.5 wt.-%, at most 75 wt.-% or at most 72.5 wt.-%; still more preferably at most 70 wt.-%, at most 67.5 wt.-%, at most 65 wt.-% or at most 62.5 wt.-%; yet more preferably at most 60 wt.-%, at most 57.5 wt.-%, at most 55 wt.-% or at most 52.5 wt.-%; most preferably at most 50 wt.-%, at most 47.5 wt.-%, at most 45 wt.-% or at most 42.5 wt.-%; and in particular at most 40 wt.-%, at most 37.5 wt.-%, or at most 35 wt.-%; based on the total weight of the tablet.

In a preferred embodiment, the content of the matrix material is within the range of 40±5 wt.-%, more preferably 40±2.5 wt.-%, based on the total weight of the tablet. In another preferred embodiment, the content of the matrix material is within the range of 45±10 wt.-%, more preferably 45±7.5 wt.-%, still more preferably 45±5 wt.-%, and most preferably 45±2.5 wt.-%, based on the total weight of the tablet. In still another preferred embodiment, the content of the matrix material is within the range of 50±10 wt.-%, more preferably 50±7.5 wt.-%, still more preferably 50±5 wt.-%, and most preferably 50±2.5 wt.-%, based on the total weight of the tablet. In yet another preferred embodiment, the content of the matrix material is within the range of 55±10 wt.-%, more preferably 55±7.5 wt.-%, still more preferably 55±5 wt.-%, and most preferably 55±2.5 wt.-%, based on the total weight of the tablet.

Preferably, the matrix material is a mixture, preferably a homogeneous mixture of at least two different constituents, more preferably of at least three different constituents. In a preferred embodiment, all constituents of the matrix material are homogeneously distributed in the continuous phase that is formed by the matrix material.

In a preferred embodiment, the mixture of all constituents of the matrix material is blended and employed as a powder, i.e. in non-pre-compacted form, subsequently mixed with the particulates that contain the pharmacologically active compound and the polyalkylene oxide, and then compressed into tablets. Tablets having acceptance values between about 5 and 6 according to Ph. Eur. 2.9.40 "Uniformity of Dosage Units" (UDU) can be obtained when properly adjusting the tablet press. Vibrations should be avoided to a maximal extent (e.g. by decoupling of hopper and tablet press) and clearance of equipment parts should be as small as possible. For example, on a rotary tablet press IMA S250 plus with 26 stations, the following parameters are suitable: round punches 10 mm diameter, radius of curvature 8 mm without debossing; fill curve 13 mm; tablet weight 500 mg; speed: 13700-13800 tablets per hour; pre compression force 4.7 kN; main compression force 6.7 kN and 8.7 kN; fill depth 14.5 mm and 15 mm; height of tablet bar (pre compression): 3.5 mm; height of tablet bar (main compression): 3.3 mm and 3.1 mm; revolution speed of feeder (Filomat): 40 rmp.

In another preferred embodiment, the matrix material is also provided in particulate form, i.e. in the course of the manufacture of the tablets according to the invention, the constituents of the matrix material are preferably processed into particulates, subsequently mixed with the coated particulates that contain the pharmacologically active compound and the physiologically acceptable polymer, preferably the polyalkylene oxide, and then compressed into the tablets.

Preferably, the average size of the particulates of the matrix material is within the range of ±60%, more preferably ±50%, still more preferably ±40%, yet more preferably ±30%, most preferably ±20%, and in particular ±10% of the average size of the coated particulates that contain the pharmacologically active compound and the physiologically acceptable polymer, preferably the polyalkylene oxide.

It has been surprisingly found that when proceeding this way, segregation phenomena upon blending the coated particulates with the matrix material in particulate form can be reduced or even completely suppressed, thereby substantially improving the content uniformity of the tablets according to the invention.

This is particularly surprising, as the larger the particulates are which are to be mixed and compressed to tablets, the more difficult it typically is to satisfy content uniformity requirements. Compared to conventional tablets, the tablets according to the invention are manufactured from comparatively large coated particulates and optionally, also from comparatively large pre-compacted particulates of matrix material. Preferably, the AV (acceptance value) concerning the content uniformity of the tablets according to the invention is at most 15, more preferably at most 14, still more preferably at most 13, yet more preferably at most 12, even more preferably at most 11, most preferably at most 10 and in particular at most 9. Methods to determine the AV are known to the skilled artisan. Preferably, the AV is determined in accordance with Eur. Ph.

Figure 2:
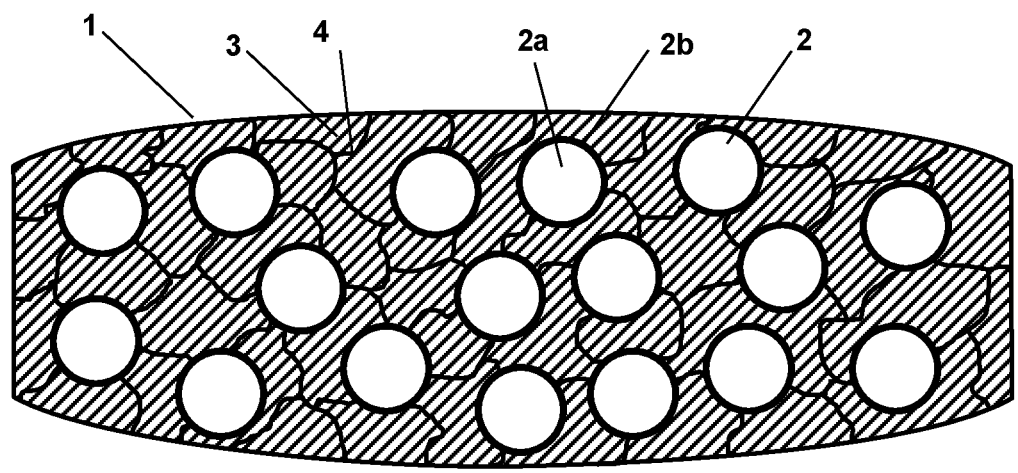
FIG. 2 schematically illustrates another preferred embodiment of the tablets according to the invention.

This preferred embodiment of the tablets according to the invention is schematically illustrated in FIG. 2. Tablet (1) contains a plurality of coated particulates (2) having core (2a) and coating (2b) that form a discontinuous phase within matrix material (3) which in turn forms a continuous phase and is also provided in particulate form, the individual particulates being in intimate contact with one another at boundaries (4). As the particulates of the matrix material typically have a mechanical strength lower than that of the coated particulates (2), the particulates of the matrix material are deformed in the course of the manufacture of the tablets by compression.

The particulates of the matrix material can principally also be coated, optionally with the same coating material of the coated particulates according to the invention or with another coating material. Preferably, however, the particulates of the matrix material are uncoated.

The particulates of the matrix material can be manufactured by conventional methods for the preparation of aggregates and agglomerates from powder mixtures such as granulating and compacting.

In a preferred embodiment, the mixture of all constituents of the matrix material is blended and pre-compacted thereby yielding a pre-compacted matrix material.

Suitable methods for the manufacture of such a pre-compacted matrix material are known to the skilled person. Preferably, pre-compaction proceeds by dry granulation, preferably slugging or roller compaction. When proceeding this way, the process parameters are typically to be adjusted in order to achieve the desired properties (see below). Typical process parameters are compaction force (preferably adjusted within the range of 2 to 12 kN), roller displacement (preferably adjusted within the range of 2 to 5 mm) and granule sieve (preferably adjusted within the range of 1.0 to 2.0 mm). The desired properties of the pre-compacted material include primarily the particle size and the content of fine particles. The density may also play a role. The particle size is preferably within the range for the size of the particulates (preferably at least 60%>700 µm for particulates having dimensions of 0.8×0.8 mm). The content of fine particles (i.e. particles having a size of less than 600 µm) is preferably at most 40%, more preferably at most 30%, most preferably at most 20%. The effect of said process parameters on said desired properties can be easily determined by a skilled person by routine experimentation.

In another preferred embodiment, the mixture of all constituents of the matrix material is dry granulated thereby yielding a granulated matrix material. In still another preferred embodiment, the mixture of all constituents of the matrix material is wet granulated by means of a non-aqueous solvent e.g. ethanol thereby yielding another granulated matrix material. Aqueous granulation, however, is preferably avoided, as this typically has a detrimental influence on disintegration of the tablet. In yet another preferred embodiment, the mixture of all constituents of the matrix material is melt granulated, e.g. by means of an extruder, a heatable high-shear mixer or a granulator.

As already mentioned above, the matrix material in the tablet according to the invention should ensure rapid disintegration and subsequent release of the pharmacologically active compound from the disintegrated tablets, i.e. from the coated particulates. Thus, the matrix material preferably does not contain any excipient that might have a retardant effect on disintegration and drug release, respectively. Further, the matrix material preferably does not contain any pharmacologically active compound.

Preferably, the matrix material comprises a disintegrant. Suitable disintegrants are known to the skilled person and are preferably selected from the group consisting of cross-linked sodium carboxymethylcellulose (Na-CMC) (e.g. Crosscarmellose, Ac-Di-Sol®); crosslinked casein (e.g. Esma-Spreng®); polysaccharide mixtures obtained from soybeans (e.g. Emcosoy®); pretreated maize starch (e.g. Amijel®); sodium alginate; polyvinylpyrrolidone (PVP) (e.g. Kollidone®, Polyplasdone®, Polydone®); crosslinked polyvinylpyrrolidone (PVP CI) (e.g. Polyplasdone® XL); starch and pretreated starch such as sodium carboxymethyl starch (e.g. Explotab®, Prejel®, Primotab® ET, Starch® 1500, Ulmatryl®). Crosslinked polymers are particularly preferred disintegrants, especially crosslinked sodium carboxymethylcellulose (Na-CMC) or crosslinked polyvinylpyrrolidone (PVP CI).

Preferably, the disintegrant is contained in the matrix material but not in the coated particulates of the tablet according to the invention.

In a preferred embodiment, the content of the disintegrant in the matrix material is within the range of 5±4 wt.-%, more preferably 5±3 wt.-%, still more preferably 5±2.5 wt.-%, yet more preferably 5±2 wt.-%, most preferably 5±1.5 wt.-%, and in particular 5±1 wt.-%, based on the total weight of matrix material. In another preferred embodiment, the content of the disintegrant in the matrix material is within the range of 7.5±4 wt.-%, more preferably 7.5±3 wt.-%, still more preferably 7.5±2.5 wt.-%, yet more preferably 7.5±2 wt.-%, most preferably 7.5±1.5 wt.-%, and in particular 7.5±1 wt.-%, based on the total weight of matrix material. In still another preferred embodiment, the content of the disintegrant in the matrix material is within the range of 10±4 wt.-%, more preferably 10±3 wt.-%, still more preferably 10±2.5 wt.-%, yet more preferably 10±2 wt.-%, most preferably 10±1.5 wt.-%, and in particular 10±1 wt.-%, based on the total weight of matrix material. In another preferred embodiment, the content of the disintegrant in the matrix material is within the range of 12.5±4 wt.-%, more preferably 12.5±3 wt.-%, still more preferably 12.5±2.5 wt.-%, yet more preferably 12.5±2 wt.-%, most preferably 12.5±1.5 wt.-%, and in particular 12.5±1 wt.-%, based on the total weight of matrix material.

In a preferred embodiment, the content of the disintegrant in the tablet is within the range of 2±1.8 wt.-%, more preferably 2±1.5 wt.-%, still more preferably 2±1.3 wt.-%, yet more preferably 2±1.0 wt.-%, most preferably 2±0.8 wt.-%, and in particular 2±0.5 wt.-%, based on the total weight of tablet. In another preferred embodiment, the content of the disintegrant in the tablet is within the range of 4±1.8 wt.-%, more preferably 4±1.5 wt.-%, still more preferably 4±1.3 wt.-%, yet more preferably 4±1.0 wt.-%, most preferably 4±0.8 wt.-%, and in particular 4±0.5 wt.-%, based on the total weight of tablet. In still another preferred embodiment, the content of the disintegrant in the tablet is within the range of 6±1.8 wt.-%, more preferably 6±1.5 wt.-%, still more preferably 6±1.3 wt.-%, yet more preferably 6±1.0 wt.-%, most preferably 6±0.8 wt.-%, and in particular 6±0.5 wt.-%, based on the total weight of tablet. In another preferred embodiment, the content of the disintegrant in the tablet is within the range of 8±1.8 wt.-%, more preferably 8±1.5 wt.-%, still more preferably 8±1.3 wt.-%, yet more preferably 8±1.0 wt.-%, most preferably 8±0.8 wt.-%, and in particular 8±0.5 wt.-%, based on the total weight of tablet.

Preferably, the matrix material comprises a disintegrant in combination with one or more water insoluble pharmaceutical excipients, preferably fillers/binders and/or lubricants.

Preferably, the matrix material comprises a filler or a binder. As many fillers can be regarded as binders and vice versa, for the purpose of specification "filler/binder" refers to any excipient that is suitable as filler, binder or both. Thus, the matrix material preferably comprises a filler/binder.

Preferred fillers (=filler/binders) are selected from the group consisting of silicium dioxide (e.g. Aerosil®), microcrystalline cellulose (e.g. Avicel®, Elcema®, Emocel®, ExCel®, Vitacell®); cellulose ether (e.g. Natrosol®, Klucel®, Methocel®, Blanose®, Pharmacoat®, Viscontran®); mannitol; dextrines; dextrose; calciumhydrogen phosphate (e.g. Emcompress®); maltodextrine (e.g. Emdex®); lactose (e.g. Fast-Flow Lactose®; Ludipress®, Tablettose®, Zeparox®); polyvinylpyrrolidone (PVP) (e.g. Kollidone®, Polyplasdone®, Polydone®); saccharose (e.g. Nu-Tab®, Sugar Tab®); magnesium salts (e.g. $MgCO_3$, $MgO$, $MgSiO_3$); starches and pretreated starches (e.g. Prejel®, Primotab® ET, Starch® 1500). Preferred binders are selected from the group consisting of alginates; chitosanes; and any of the fillers mentioned above (=fillers/binders).

Some fillers/binders may also serve other purposes. It is known, for example, that silicium dioxide exhibits excellent function as a glidant. Thus, preferably, the matrix material comprises a glidant such as silicium dioxide.

In a preferred embodiment, the content of the filler/binder or mixture of fillers/binders in the matrix material is within the range of 50±25 wt.-%, more preferably 50±20 wt.-%, still more preferably 50±15 wt.-%, yet more preferably 50±10 wt.-%, most preferably 50±7.5 wt.-%, and in particular 50±5 wt.-%, based on the total weight of matrix material. In another preferred embodiment, the content of the filler/binder or mixture of fillers/binders in the matrix material is within the range of 65±25 wt.-%, more preferably 65±20 wt.-%, still more preferably 65±15 wt.-%, yet more preferably 65±10 wt.-%, most preferably 65±7.5 wt.-%, and in particular 65±5 wt.-%, based on the total weight of matrix material. In still another preferred embodiment, the content of the filler/binder or mixture of fillers/binders in the matrix material is within the range of 80±19 wt.-%, more preferably 80±17.5 wt.-%, still more preferably 80±15 wt.-%, yet more preferably 80±10 wt.-%, most preferably 80±7.5 wt.-%, and in particular 80±5 wt.-%, based on the total weight of matrix material. In another preferred embodiment, the content of the filler/binder or mixture of fillers/binders in the matrix material is within the range of 90±9 wt.-%, more preferably 90±8 wt.-%, still more preferably 90±7 wt.-%, yet more preferably 90±6 wt.-%, most preferably 90±5 wt.-%, and in particular 90±4 wt.-%, based on the total weight of matrix material.

In a preferred embodiment, the content of the filler/binder or mixture of fillers/binders in the tablet is within the range of 25±24 wt.-%, more preferably 25±20 wt.-%, still more preferably 25±16 wt.-%, yet more preferably 25±12 wt.-%, most preferably 25±8 wt.-%, and in particular 25±4 wt.-%, based on the total weight of tablet. In another preferred embodiment, the content of the filler/binder or mixture of fillers/binders in the tablet is within the range of 30±29 wt.-%, more preferably 30±25 wt.-%, still more preferably 30±20 wt.-%, yet more preferably 30±15 wt.-%, most preferably 30±10 wt.-%, and in particular 30±5 wt.-%, based on the total weight of tablet. In still another preferred embodiment, the content of the filler/binder or mixture of fillers/binders in the tablet is within the range of 35±34 wt.-%, more preferably 35±28 wt.-%, still more preferably 35±22 wt.-%, yet more preferably 35±16 wt.-%, most preferably 35±10 wt.-%, and in particular 35±4 wt.-%, based on the total weight of tablet. In another preferred embodiment, the content of the filler/binder or mixture of fillers/binders in the tablet is within the range of 40±39 wt.-%, more preferably 40±32 wt.-%, still more preferably 40±25 wt.-%, yet more preferably 40±18 wt.-%, most preferably 40±11 wt.-%, and in particular 40±4 wt.-%, based on the total weight of tablet.

Preferably, the filler/binder is contained in the matrix material but not in the coated particulates of the tablet according to the invention.

In a preferred embodiment, a portion (e.g. 10% of the total tablet mass) of the matrix is granulated on the coated particulates (preferably by non-aqueous wet granulation, e.g. with isopropylic alcohol) and the remaining matrix material is added to the thus granulated coated particulates and blended prior to compression/processing to tablets. Thus, according to this embodiment, the particulates are coated by a coating that in turn is overcoated a portion of the matrix material, whereas the remainder of the matrix material is preferably employed in non-granulated form.

Preferably, the matrix material comprises a diluent or lubricant, preferably selected from the group consisting of calcium stearate; magnesium stearate; glycerol monobehenate (e.g. Compritol®); Myvatex®; Precirol®; Precirol® Ato5; sodium stearylfumarate (e.g. Pruv®); and talcum. Magnesium stearate is particularly preferred. Preferably, the content of the lubricant in the matrix material is at most 10.0 wt.-%, more preferably at most 7.5 wt.-%, still more preferably at most 5.0 wt.-%, yet more preferably at most 2.0 wt.-%, even more preferably at most 1.0 wt.-%, and most preferably at most 0.5 wt.-%, based on the total weight of the matrix material and based on the total weight of tablet.

In particularly preferred embodiment, the matrix material comprises a combination of disintegrant, filler/binder and lubricant.

Particularly preferred contents of disintegrant, filler/binder and lubricant of the matrix material, relative to the total weight of the matrix material, are summarized as embodiments $A^1$ to $A^6$ in the table here below:

| wt.-% | A¹ | A² | A³ | A⁴ | A⁵ | A⁶ |
|---|---|---|---|---|---|---|
| disintegrant | 11 ± 10 | 11 ± 7.5 | 11 ± 5.0 | 11 ± 3.5 | 11 ± 2.5 | 11 ± 1.5 |
| filler/binder | 88 ± 12 | 88 ± 10 | 88 ± 8 | 88 ± 6 | 88 ± 4 | 88 ± 2.5 |
| lubricant | 0.30 ± 0.28 | 0.30 ± 0.26 | 0.30 ± 0.24 | 0.30 ± 0.22 | 0.30 ± 0.20 | 0.30 ± 0.15 | wherein the disintegrant is preferably crosslinked sodium carboxymethyl cellulose (Na-CMC) or crosslinked polyvinylpyrrolidone (PVP CI); the filler binder is preferably microcrystalline cellulose or a combination of microcrystalline cellulose with colloidal silicon dioxide; and the lubricant is preferably magnesium stearate.

The matrix material of the tablets according to the invention may additionally contain other excipients that are conventional in the art, e.g. diluents, binders, granulating aids, colourants, flavourants, pore formers, surfactants, glidants, wet-regulating agents and disintegrants. The skilled person will readily be able to determine appropriate quantities of each of these excipients.

Preferred pore formers include, but are not limited to glucose, fructose, mannitol, mannose, galactose, sorbitol, pullulan, dextran, water-soluble hydrophilic polymers, hydroxyalkylcelluloses, carboxyalkylcelluloses, hydroxypropylmethylcellulose, cellulose ethers, acrylic resins, polyvinylpyrrolidone, cross-linked polyvinylpyrrolidone, polyethylene oxide, carbowaxes, carbopol, diols, polyols, polyhydric alcohols, polyalkylene glycols, polyethylene glycols, polypropylene glycols or block polymers thereof, polyglycols, poly(α-ω)alkylenediols; inorganic compounds; alkali metal salts; alkaline earth metal salts, or combinations thereof.

Preferred surfactants are nonionic, anionic, cationic or amphoteric surfactants.

In a preferred embodiment, the matrix material contains an ionic surfactant, in particular an anionic surfactant.

Suitable anionic surfactants include but are not limited to sulfuric acid esters such as sodium lauryl sulfate (sodium dodecyl sulfate, e.g. Texapon® K12), sodium cetyl sulfate (e.g. Lanette E®), sodium cetylstearyl sulfate, sodium stearyl sulfate, sodium dioctylsulfosuccinate (docusate sodium); and the corresponding potassium or calcium salts thereof.

Preferably, the anionic surfactant has the general formula (II-a)

$$C_nH_{2n+1}O\text{—}SO_3^-M^+ \quad \text{(II-a)},$$

wherein n is an integer of from 8 to 30, preferably 10 to 24, more preferably 12 to 18; and M is selected from Li⁺, Na⁺, K⁺, NH₄⁺½ Mg²⁺ and ½ Ca²⁺.

Further suitable anionic surfactants include salts of cholic acid including sodium glycocholate (e.g. Konakion® MM, Cernevit®), sodium taurocholate and the corresponding potassium or ammonium salts.

In another preferred embodiment, the matrix material contains a non-ionic surfactant. Suitable non-ionic surfactants include but are not limited to
- fatty alcohols that may be linear or branched, such as cetylalcohol, stearylalcohol, cetylstearyl alcohol, 2-octyldodecane-1-ol and 2-hexyldecane-1-ol;
- sterols, such as cholesterole;
- partial fatty acid esters of sorbitan such as sorbitanmonolaurate, sorbitanmonopalmitate, sorbitanmonostearate, sorbitantristearate, sorbitanmonooleate, sorbitansesquioleate and sorbitantrioleate;
- partial fatty acid esters of polyoxyethylene sorbitan (polyoxyethylene-sorbitan-fatty acid esters), preferably a fatty acid monoester of polyoxyethylene sorbitan, a fatty acid diester of polyoxyethylene sorbitan, or a fatty acid triester of polyoxyethylene sorbitan; e.g. mono- and tri-lauryl, palmityl, stearyl and oleyl esters, such as the type known under the name "polysorbat" and commercially available under the trade name "Tween" including Tween® 20 [polyoxyethylene(20)sorbitan monolaurate], Tween® 21 [polyoxyethylene(4)sorbitan monolaurate], Tween® 40 [polyoxyethylene(20)sorbitan monopalmitate], Tween® 60 [polyoxyethylene(20) sorbitan monostearate], Tween® 65 [polyoxyethylene(20)sorbitan tristearate], Tween® 80 [polyoxyethylene(20)sorbitan monooleate], Tween 81 [polyoxyethylene(5)sorbitan monooleate], and Tween® 85 [polyoxyethylene(20)sorbitan trioleate]; preferably a fatty acid monoester of polyoxyethylenesorbitan according to general formula (II-b)

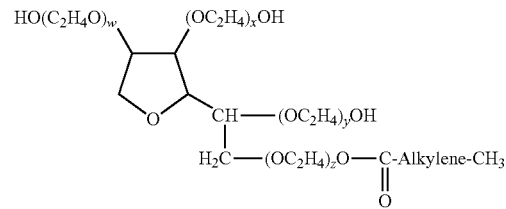

(II-b)

wherein (w+x+y+z) is within the range of from 15 to 100, preferably 16 to 80, more preferably 17 to 60, still more preferably 18 to 40 and most preferably 19 to 21; and alkylene is an optionally unsaturated alkylene group comprising 6 to 30 carbon atoms, more preferably 8 to 24 carbon atoms and most preferably 10 to 16 carbon atoms;
- polyoxyethyleneglycerole fatty acid esters such as mixtures of mono-, di- and triesters of glycerol and di- and monoesters of macrogols having molecular weights within the range of from 200 to 4000 g/mol, e.g., macrogolglycerolcaprylocaprate, macrogolglycerollaurate, macrogolglycerolococoate, macrogolglycerollinoleate, macrogol-20-glycerolmonostearate, macrogol-6-glycerolcaprylocaprate, macrogolglycerololeate; macrogolglycerolstearate, macrogolglycerolhydroxystearate (e.g. Cremophor® RH 40), and macrogolglycerolrizinoleate (e.g. Cremophor® EL);
- polyoxyethylene fatty acid esters, the fatty acid preferably having from about 8 to about 18 carbon atoms, e.g. macrogololeate, macrogolstearate, macrogol-15-hydroxystearate, polyoxyethylene esters of 12-hydroxystearic acid, such as the type known and commercially available under the trade name "Solutol HS 15"; preferably according to general formula (II-c)

$$CH_3CH_2\text{—}(OCH_2CH_3)_n\text{—}O\text{—}CO\text{—}(CH_2)_mCH_3 \quad \text{(II-c)}$$

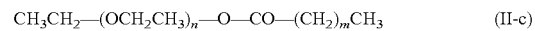

wherein n is an integer of from 6 to 500, preferably 7 to 250, more preferably 8 to 100, still more preferably 9 to 75, yet more preferably 10 to 50, even more preferably 11 to 30, most preferably 12 to 25, and in particular 13 to 20; and wherein m is an integer of from 6 to 28; more preferably 6 to 26, still more preferably 8 to 24, yet more preferably 10 to 22, even more preferably 12 to 20, most preferably 14 to 18 and in particular 16;

polyoxyethylene fatty alcohol ethers, e.g. macrogolcetylstearylether, macrogollarylether, macrogololeylether, macrogolstearylether;

polyoxypropylene-polyoxyethylene block copolymers (poloxamers);

fatty acid esters of saccharose; e.g. saccharose distearate, saccharose dioleate, saccharose dipalmitate, saccharose monostearate, saccharose monooleate, saccharose monopalmitate, saccharose monomyristate and saccharose monolaurate;

fatty acid esters of polyglycerol, e.g. polyglycerololeate;

polyoxyethylene esters of alpha-tocopheryl succinate, e.g. D-alpha-tocopheryl-PEG-1000-succinate (TPGS);

polyglycolyzed glycerides, such as the types known and commercially available under the trade names "Gelucire 44/14", "Gelucire 50/13 and "Labrasol";

reaction products of a natural or hydrogenated castor oil and ethylene oxide such as the various liquid surfactants known and commercially available under the trade name "Cremophor"; and partial fatty acid esters of multifunctional alcohols, such as glycerol fatty acid esters, e.g. mono- and tri-lauryl, palmityl, stearyl and oleyl esters, for example glycerol monostearate, glycerol monooleate, e.g. glyceryl monooleate 40, known and commercially available under the trade name "Peceol"; glycerole dibehenate, glycerole distearate, glycerole monolinoleate; ethyleneglycol monostearate, ethyleneglycol monopalmitostearate, pentaerythritol monostearate.

In a preferred embodiment, the matrix material according to the invention comprises a surfactant or mixture of different surfactants obtainable by (i) esterifying saturated or unsaturated $C_{12}$-$C_{18}$-fatty acids, optionally bearing a hydroxyl group, with a polyethylene glycol and optionally, glycerol; wherein the polyethylene glycol preferably comprises 10 to 40 ethylene oxide units (—$CH_2CH_2O$—); and/or (ii) etherifying triglycerides of saturated or unsaturated $C_{12}$-$C_{18}$-fatty acids bearing a hydroxyl group with ethylene oxide so that a polyethylene glycol moiety is linked to the hydroxyl group of the $C_{12}$-$C_{18}$-fatty acids via an ether bond; wherein the polyethylene glycol moiety preferably comprises 30 to 50 ethylene oxide units (—$CH_2CH_2O$—).

In a preferred embodiment, the content of the surfactant is at least 0.001 wt.-% or at least 0.005 wt.-%, more preferably at least 0.01 wt.-% or at least 0.05 wt.-%, still more preferably at least 0.1 wt.-%, at least 0.2 wt.-%, or at least 0.3 wt.-%, yet more preferably at least 0.4 wt.-%, at least 0.5 wt.-%, or at least 0.6 wt.-%, and in particular at least 0.7 wt.-%, at least 0.8 wt.-%, at least 0.9 wt.-%, or at least 1.0 wt.-%, based on the total weight of the tablet.

In a preferred embodiment, however, the matrix material of the tablet according to the invention consists of one or more disintegrants, one or more filler/binder's and one or more lubricants, but does not contain any other constituents.

In a particularly preferred embodiment, the matrix material of the tablet according to the invention does not contain one or more gel-forming agents and/or a silicone.

As used herein the term "gel-forming agent" is used to refer to a compound that, upon contact with a solvent (e.g. water), absorbs the solvent and swells, thereby forming a viscous or semi-viscous substance. Preferred gel-forming agents are not cross-linked. This substance may moderate pharmacologically active compound release from the embedded particulates in both aqueous and aqueous alcoholic media. Upon full hydration, a thick viscous solution or dispersion is typically produced that significantly reduces and/or minimizes the amount of free solvent which can contain an amount of solubilized pharmacologically active compound, and which can be drawn into a syringe. The gel that is formed may also reduce the overall amount of pharmacologically active compound extractable with the solvent by entrapping the pharmacologically active compound within a gel structure. Thus the gel-forming agent may play an important role in conferring tamper-resistance to the tablets according to the invention.

Gel-forming agents that preferably are not contained in the matrix material include pharmaceutically acceptable polymers, typically hydrophilic polymers, such as hydrogels. Representative examples of gel-forming agent include polyethylene oxide, polyvinyl alcohol, hydroxypropylmethyl cellulose, carbomers, poly(uronic) acids and mixtures thereof.

Thus, the physiologically acceptable polymer, preferably the polyalkylene oxide that is contained in the coated particulates of the tablets according to the invention is preferably not also contained in the matrix material.

Preferably, the pharmacologically active compound which is contained in the coated particulates of the tablet according to the invention is preferably not also contained in the matrix material.

Thus, in a preferred embodiment, the total amount of pharmacologically active compound contained in the tablet according to the invention is present in the coated particulates which form a discontinuous phase within the matrix material; and the matrix material forming a continuous phase does not contain any pharmacologically active compound.

The tablet according to the invention contains a plurality of coated particulates. The coated particulates comprise a pharmacologically active compound and a physiologically acceptable polymer, preferably a polyalkylene oxide. Preferably, the pharmacologically active compound is dispersed in the physiologically acceptable polymer, preferably the polyalkylene oxide.

For the purpose of specification, the term "particulate" refers to a discrete mass of material that is solid, e.g. at 20° C. or at room temperature or ambient temperature. Preferably a particulate is solid at 20° C. Preferably, the coated particulates are monoliths. Preferably, the pharmacologically active compound and the physiologically acceptable polymer, preferably the polyalkylene oxide are intimately homogeneously distributed in the coated particulates so that the coated particulates do not contain any segments where either pharmacologically active compound is present in the absence of physiologically acceptable polymer, preferably polyalkylene oxide or where physiologically acceptable polymer, preferably polyalkylene oxide is present in the absence of pharmacologically active compound.

The particulates are film coated and the physiologically acceptable polymer, preferably the polyalkylene oxide is preferably homogeneously distributed in the core of the pharmaceutical dosage form (tablet), i.e. the film coating preferably does not contain physiologically acceptable polymer, preferably polyalkylene oxide, but optionally polyalkylene glycol that differs from polyalkylene oxide in its lower molecular weight. Nonetheless, the film coating as such may of course contain one or more polymers, which however, preferably differ from the polyalkylene oxide contained in the core.

The coated particulates are of macroscopic size, typically the average diameter is within the range of from 100 µm to 1500 µm, preferably 200 µm to 1500 µm, more preferably 300 µm to 1500 µm, still more preferably 400 µm to 1500 µm, most preferably 500 µm to 1500 µm, and in particular 600 µm to 1500 µm. The tablets according to the invention comprise particulates as a discontinuous phase, i.e. the coated particulates form a discontinuous phase in the matrix material which in turn preferably forms a continuous phase. In this regard, discontinuous means that not each and every particulate is in intimate contact with another particulate but that the coated particulates are at least partially separated from one another by the matrix material in which the coated particulates are embedded. In other words, the coated particulates preferably do not form a single coherent mass within the tablets according to the invention.

The tablet according to the invention comprises particulates in an amount of less than two thirds of the total weight of the tablet.

It has been surprisingly found that the content of particulates in the tablet can be optimized in order to provide the best compromise between tamper-resistance, disintegration time and drug release, drug load, processability (especially tablettability) and patient compliance.

Preferably, the content of the coated particulates in the tablets according to the invention is at most 65 wt.-%, more preferably at most 62.5 wt.-%, still more preferably at most 60 wt.-%, yet more preferably at most 57.5 wt.-%, most preferably at most 55 wt.-% and in particular at most 52.5 wt.-%, based on the total weight of the tablets.

Preferably, the content of the coated particulates in the tablets according to the invention is at least 10 wt.-%, at least 12.5 wt.-%, at least 15 wt.-% or at least 17.5 wt.-%; more preferably at least 20 wt.-%, at least 22.5 wt.-%, at least 25 wt.-% or at least 27.5 wt.-%; most preferably at least 30 wt.-%, at least 32.5 wt.-%, at least 35 wt.-% or at least 37.5 wt.-%; and in particular at least 40 wt.-%, at least 42.5 wt.-%, at least 45 wt.-% or at least 47.5 wt.-%; based on the total weight of the tablet.

In a preferred embodiment, the content of the coated particulates in the tablets according to the invention is within the range of 35±30 wt.-%, more preferably 35±25 wt.-%, still more preferably 35±20 wt.-%, yet more preferably 35±15 wt.-%, most preferably 35±10 wt.-%, and in particular 35±5 wt.-%, based on the total weight of the tablet. In another preferred embodiment, the content of the coated particulates in the tablets according to the invention is within the range of 40±30 wt.-%, more preferably 40±25 wt.-%, still more preferably 40±20 wt.-%, yet more preferably 40±15 wt.-%, most preferably 40±10 wt.-%, and in particular 40±5 wt.-%, based on the total weight of the tablet. In still another preferred embodiment, the content of the coated particulates in the tablets according to the invention is within the range of 45±30 wt.-%, more preferably 45±25 wt.-%, still more preferably 45±20 wt.-%, yet more preferably 45±15 wt.-%, most preferably 45±10 wt.-%, and in particular 45±5 wt.-%, based on the total weight of the tablet. In yet another preferred embodiment, the content of the coated particulates in the tablets according to the invention is within the range of 50±30 wt.-%, more preferably 50±25 wt.-%, still more preferably 50±20 wt.-%, yet more preferably 50±15 wt.-%, most preferably 50±10 wt.-%, and in particular 50±5 wt.-%, based on the total weight of the tablet. In another preferred embodiment, the content of the coated particulates in the tablets according to the invention is within the range of 55±30 wt.-%, more preferably 55±25 wt.-%, still more preferably 55±20 wt.-%, yet more preferably 55±15 wt.-%, most preferably 55±10 wt.-%, and in particular 55±5 wt.-%, based on the total weight of the tablet. In still another preferred embodiment, the content of the coated particulates in the tablets according to the invention is within the range of 60±30 wt.-%, more preferably 60±25 wt.-%, still more preferably 60±20 wt.-%, yet more preferably 60±15 wt.-%, most preferably 60±10 wt.-%, and in particular 60±5 wt.-%, based on the total weight of the tablet.

The shape of the coated particulates is not particularly limited. As the coated particulates are preferably manufactured by hot-melt extrusion, preferred coated particulates present in the tablets according to the invention are generally cylindrical in shape. The diameter of such coated particulates is therefore the diameter of their circular cross section. The cylindrical shape is caused by the extrusion process according to which the diameter of the circular cross section is a function of the extrusion die and the length of the cylinders is a function of the cutting length according to which the extruded strand of material is cut into pieces of preferably more or less predetermined length.

The suitability of cylindrical, i.e. a spherical particulates for the manufacture of the tablets according to the invention is unexpected. Typically, the aspect ratio is regarded as an important measure of the spherical shape. The aspect ratio is defined as the ratio of the maximal diameter ($d_{max}$) and its orthogonal Feret-diameter. For aspherical particulates, the aspect ratio has values above 1. The smaller the value the more spherical is the particulate. Aspect ratios below 1.1 are typically considered satisfactory, aspect ratios above 1.2, however, are typically considered not suitable for the manufacture of conventional tablets. The inventors have surprisingly found that when manufacturing the tablets according to the invention, even particulates having aspect ratios above 1.2 can be processed without difficulties and that it is not necessary to provide spherical particulates. In a preferred embodiment, the aspect ratio of the coated particulates is at most 1.40, more preferably at most 1.35, still more preferably at most 1.30, yet more preferably at most 1.25, even more preferably at most 1.20, most preferably at most 1.15 and in particular at most 1.10. In another preferred embodiment, the aspect ratio of the coated particulates is at least 1.10, more preferably at least 1.15, still more preferably at least 1.20, yet more preferably at least 1.25, even more preferably at least 1.30, most preferably at least 1.35 and in particular at least 1.40.

The coated particulates in the tablets according to the invention are of macroscopic size, i.e. typically have an average particle size of at least 50 µm, more preferably at least 100 µm, still more preferably at least 150 µm or at least 200 µm, yet more preferably at least 250 µm or at least 300 µm, most preferably at least 400 µm or at least 500 µm, and in particular at least 550 µm or at least 600 µm.

Preferred coated particulates have an average length and average diameter of about 1000 µm or less. When the coated particulates are manufactured by extrusion technology, the "length" of coated particulates is the dimension of the coated particulates that is parallel to the direction of extrusion. The "diameter" of coated particulates is the largest dimension that is perpendicular to the direction of extrusion.

Particularly preferred coated particulates have an average diameter of less than about 1000 µm, more preferably less than about 800 µm, still more preferably of less than about 650 μm. Especially preferred coated particulates have an average diameter of less than 700 μm, particularly less than 600 μm, still more particularly less than 500 μm, e.g. less than 400 μm. Particularly preferred particulates have an average diameter in the range 200-1000 μm, more preferably 400-800 μm, still more preferably 450-700 μm, yet more preferably 500-650 μm, e.g. about 500-600 μm. Further preferred particulates have an average diameter of between about 300 μm and about 400 μm, of between about 400 μm and 500 μm, or of between about 500 μm and 600 μm, or of between 600 μm and 700 μm or of between 700 μm and 800 μm.

Preferred particulates that are present in the tablets according to the invention have an average length of less than about 1000 μm, preferably an average length of less than about 800 μm, still more preferably an average length of less than about 650 μm, e.g. a length of about 800 μm, about 700 μm about 600 μm, about 500 μm, about 400 μm or about 300 μm. Especially preferred particulates have an average length of less than 700 μm, particularly less than 650 μm, still more particularly less than 550 μm, e.g. less than 450 μm. Particularly preferred particulates therefore have an average length in the range 200-1000 μm, more preferably 400-800 μm, still more preferably 450-700 μm, yet more preferably 500-650 μm, e.g. about 500-600 μm. The minimum average length of the microparticulates is determined by the cutting step and may be, e.g. 500 μm, 400 μm, 300 μm or 200 μm.

In a preferred embodiment, the coated particulates have (i) an average diameter of about 1000±300 μm, more preferably 1000±250 μm, still more preferably 1000±200 μm, yet more preferably 100±150 μm, most preferably 1000±100 μm, and in particular 1000±50 μm; and/or (ii) an average length of about 750±300 μm, more preferably 750±250 μm, still more preferably 750±200 μm, yet more preferably 750±150 μm, most preferably 750±100 μm, and in particular 750±50 μm.

In another preferred embodiment, the coated particulates have (i) an average diameter of about 750±300 μm, more preferably 750±250 μm, still more preferably 750±200 μm, yet more preferably 750±150 μm, most preferably 750±100 μm, and in particular 750±50 μm; and/or (ii) an average length of about 750±300 μm, more preferably 750±250 μm, still more preferably 750±200 μm, yet more preferably 750±150 μm, most preferably 750±100 μm, and in particular 750±50 μm.

It has been surprisingly found that the size of the coated particulates in the tablet can be optimized in order to provide the best compromise between tamper-resistance, disintegration time and drug release, drug load, processability (especially tablettability) and patient compliance.

The size of particulates may be determined by any conventional procedure known in the art, e.g. laser light scattering, sieve analysis, light microscopy or image analysis.

Preferably, the plurality of coated particulates that is contained in the tablet according to the invention has an arithmetic average weight, in the following referred to as "aaw", wherein at least 70%, more preferably at least 75%, still more preferably at least 80%, yet more preferably at least 85%, most preferably at least 90% and in particular at least 95% of the individual particles contained in said plurality of coated particulates has an individual weight within the range of aaw±30%, more preferably aaw±25%, still more preferably aaw±20%, yet more preferably aaw±15%, most preferably aaw±10%, and in particular aaw±5%. For example, if the tablet according to the invention contains a plurality of 100 particulates and aaw of said plurality of coated particulates is 1.00 mg, at least 75 individual particles (i.e. 75%) have an individual weight within the range of from 0.70 to 1.30 mg (1.00 mg±30%).

The particulates are coated, preferably film coated. It has been surprisingly found that when the particulates are film coated, the disintegration time and/or the drug release from the tablets can be further accelerated, which is particularly significant for tablets with immediate drug release.

Preferably, the plurality of coated particulates contained in the dosage form according to the invention encompasses the total quantity of particulates which contain the pharmacologically active compound, i.e. preferably all active compound containing particulates are coated.

Preferably, the coating material does not contain a disintegrant.

The particulates according to the invention are provided, partially or preferably completely, with a coating. The particulates according to the invention are preferably film coated with film coating compositions. Suitable coating materials are commercially available, e.g. under the trademarks Opadry® and Eudragit®.

Preferably, the coating material comprises a water-soluble polymer. For the purpose of specification, a water-soluble polymer is preferably a non-enteric polymer that rapidly dissolves when being exposed to an acidic medium such as gastric juice. Preferably, the water-solubility of the polymer in 100 g artificial gastric juice (HCl aq.) at pH 1.2 and 21° C. is at least 1.0 g, more preferably at least 2.0 g, still more preferably at least 3.0 g, yet more preferably at least 4.0 g, most preferably at least 5.0 g, and in particular at least 6.0 g.

Examples of suitable coating materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), ethylcellulose (EC), cellulose acetate phthalate (CAP), hydroxypropylmethylcellulose phthalate (HPMCP); poly(meth)acrylates, such as aminoalkylmethacrylate copolymers, ethylacrylate methylmethacrylate copolymers, methacrylic acid methylmethacrylate copolymers, methacrylic acid methylmethacrylate copolymers; vinyl polymers, such as polyvinylpyrrolidone, polyvinylacetatephthalate, polyvinyl alcohol, polyvinyl alcohol-polyethylene glycol graft copolymers, polyvinylacetate; and natural film formers.

The coating material may contain excipients such as stabilizers (e.g. surfactants such as macrogol cetostearylether, sodium dodecylsulfate, and the like). Suitable excipients of film coating materials are known to the skilled person.

In a particularly preferred embodiment, the coating is water-soluble. In a preferred embodiment, the coating is based on polyvinyl alcohol, such as polyvinyl alcohol-part. hydrolyzed, and may additionally contain polyethylene glycol, such as macrogol 3350, and/or pigments. In another preferred embodiment, the coating is based on hydroxypropylmethylcellulose, preferably hypromellose type 2910 having a viscosity of 3 to 15 mPas.

A particularly preferred coating contains polyvinyl alcohol and optionally, further excipients such as xanthan gum and/or talcum.

The particulates are film coated and the content of the dried film coating is preferably at most 5 wt.-%, more preferably at most 4 wt.-%, still more preferably at most 3.5 wt.-%, yet more preferably at most 3 wt.-%, most preferably at most 2.5 wt.-%, and in particular at most 2 wt.-%, based on the total weight of the coated particulates. In a particularly preferred embodiment, the weight increase relative to the total weight of the particulates (uncoated starting material) is within the range of from 3.0 to 4.7 wt.-%, more preferably 3.1 to 4.6 wt.-%, still more preferably 3.2 to 4.5 wt.-%, yet more preferably 3.3 to 4.4 wt.-%, most preferably 3.4 to 4.3 wt.-%, and in particular 3.5 to 4.2 wt.-%.

It has been surprisingly found that the relative weight ratio of matrix material:particulates in the tablet can be optimized in order to provide the best compromise between tamper-resistance, disintegration time and drug release, drug load, processability (especially tablettability) and patient compliance.

Preferably, said relative weight ratio is within the range of 1:1.00±0.75, more preferably 1:1.00±0.50, still more preferably 1:1.00±0.40, yet more preferably 1:1.00±0.30, most preferably 1:1.00±0.20, and in particular 1:1.00±0.10.

The coated particulates contain at least a pharmacologically active compound and a physiologically acceptable polymer, preferably a polyalkylene oxide. Preferably, however, the coated particulates contain additional pharmaceutical excipients such as antioxidants and plasticizers.

The pharmacologically active compound is not particularly limited. Preferably, the pharmacologically active compound is an opioid.

In a preferred embodiment, the coated particulates and the tablet, respectively, contain only a single pharmacologically active compound. In another preferred embodiment, the coated particulates and the tablet, respectively, contain a combination of two or more pharmacologically active compounds.

Preferably, pharmacologically active compound is an active ingredient with potential for being abused. Active ingredients with potential for being abused are known to the person skilled in the art and comprise e.g. tranquillizers, stimulants, barbiturates, narcotics, opioids or opioid derivatives.

Preferably, the pharmacologically active compound exhibits psychotropic action.

Preferably, the pharmacologically active compound is selected from the group consisting of opiates, opioids, stimulants, tranquilizers, and other narcotics.

Particularly preferably, the pharmacologically active compound is an opioid. According to the ATC index, opioids are divided into natural opium alkaloids, phenylpiperidine derivatives, diphenylpropylamine derivatives, benzomorphan derivatives, oripavine derivatives, morphinan derivatives and others.

The following opiates, opioids, tranquillizers or other narcotics are substances with a psychotropic action, i.e. have a potential of abuse, and hence are preferably contained in the tablet and the coated particulates, respectively: alfentanil, allobarbital, allylprodine, alphaprodine, alprazolam, amfepramone, amphetamine, amphetaminil, amobarbital, anileridine, apocodeine, axomadol, barbital, bemidone, benzylmorphine, bezitramide, bromazepam, brotizolam, buprenorphine, butobarbital, butorphanol, camazepam, carfentanil, cathine/D-norpseudoephedrine, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dextromoramide, dextropropoxyphene, dezocine, diampromide, diamorphone, diazepam, dihydrocodeine, dihydromorphine, dihydromorphone, dimenoxadol, dimephetamol, dimethylthiambutene, dioxaphetylbutyrate, dipipanone, dronabinol, eptazocine, estazolam, ethoheptazine, ethylmethylthiambutene, ethyl loflazepate, ethylmorphine, etonitazene, etorphine, faxeladol, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethylmorphinan, ketazolam, ketobemidone, levacetylmethadol (LAAM), levomethadone, levorphanol, levophenacylmorphane, levoxemacin, lisdexamfetamine dimesylate, lofentanil, loprazolam, lorazepam, lormetazepam, mazindol, medazepam, mefenorex, meperidine, meprobamate, metapon, meptazinol, metazocine, methylmorphine, metamphetamine, methadone, methaqualone, 3-methylfentanyl, 4-methylfentanyl, methylphenidate, methylphenobarbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxycodone, oxymorphone, *Papaver somniferum*, papaveretum, pernoline, pentazocine, pentobarbital, pethidine, phenadoxone, phenomorphane, phenazocine, phenoperidine, piminodine, pholcodeine, phenmetrazine, phenobarbital, phentermine, pinazepam, pipradrol, piritramide, prazepam, profadol, proheptazine, promedol, properidine, propoxyphene, remifentanil, secbutabarbital, secobarbital, sufentanil, tapentadol, temazepam, tetrazepam, tilidine (cis and trans), tramadol, triazolam, vinylbital, N-(1-methyl-2-piperidinoethyl)-N-(2-pyridyl)propionamide, (1R,2R)-3-(3-dimethylamino-1-ethyl-2-methyl-propyl)phenol, (1R,2R,4S)-2-(dimethylamino)-methyl-4-(p-fluorobenzyloxy)-1-(m-methoxyphenyl)cyclohexanol, (1R,2R)-3-(2-dimethylaminomethyl-cyclohexyl)phenol, (1 S,2S)-3-(3-dimethylamino-1-ethyl-2-methyl-propyl)phenol, (2R,3R)-1-dimethylamino-3-(3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclohexyl)phenyl 2-(6-methoxy-naphthalen-2-yl)propionate, 3-(2-dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl)propionate, (RR—SS)-2-acetoxy-4-trifluoromethyl-benzoic acid 3-(2-dimethylaminomethyl-1-hydroxycyclohexyl)-phenyl ester, (RR—SS)-2-hydroxy-4-trifluoromethyl-benzoic acid 3-(2-dimethylaminomethyl-1-hydroxy-cyclohexyl)-phenyl ester, (RR—SS)-4-chloro-2-hydroxybenzoic acid 3-(2-dimethylaminomethyl-1-hydroxy-cyclohexyl)-phenyl ester, (RR—SS)-2-hydroxy-4-methyl-benzoic acid 3-(2-dimethylaminomethyl-1-hydroxy-cyclohexyl)-phenyl ester, (RR—SS)-2-hydroxy-4-methoxy-benzoic acid 3-(2-dimethylaminomethyl-1-hydroxycyclohexyl)-phenyl ester, (RR—SS)-2-hydroxy-5-nitro-benzoic acid 3-(2-dimethylaminomethyl-1-hydroxy-cyclohexyl)-phenyl ester, (RR—SS)-2',4'-difluoro-3-hydroxy-biphenyl-4-carboxylic acid 3-(2-dimethylaminomethyl-1-hydroxy-cyclohexyl)-phenyl ester, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the acid or base addition salts thereof and solvates, e.g. hydrochlorides.

In a preferred embodiment, the pharmacologically active compound is selected from the group consisting of DPI-125, M6G (CE-04-410), ADL-5859, CR-665, NRP290 and sebacoyl dinalbuphine ester.

In a preferred embodiment, the pharmacologically active compound is selected from the group consisting of oxymorphone, hydromorphone and morphine.

In another preferred embodiment, the pharmacologically active compound is selected from the group consisting of tapentadol, faxeladol and axomadol.

In still another preferred embodiment, the pharmacologically active compound is selected from the group consisting of 1,1-(3-dimethylamino-3-phenylpentamethylene)-6-fluoro-1,3,4,9-tetrahydropyrano[3,4-b]indole, particularly its hemicitrate; 1,1-[3-dimethylamino-3-(2-thienyl)-pentamethylene]-1,3,4,9-tetrahydropyrano[3,4-b]indole, particularly its citrate; and 1,1-[3-dimethylamino-3-(2-thienyl)pentamethylene]-1,3,4,9-tetrahydropyrano[3,4-b]-6-fluoroindole, particularly its hemicitrate. These compounds are known from, e.g., WO 2004/043967, WO 2005/066183.

The pharmacologically active compound may be present in form of a physiologically acceptable salt, e.g. physiologically acceptable acid addition salt.

Physiologically acceptable acid addition salts comprise the acid addition salt forms which can conveniently be obtained by treating the base form of the active ingredient with appropriate organic and inorganic acids. Active ingredients containing an acidic proton may be converted into their non-toxic metal or amine addition salt forms by treatment with appropriate organic and inorganic bases. The term addition salt also comprises the hydrates and solvent addition forms which the active ingredients are able to form. Examples of such forms are e.g. hydrates, alcoholates and the like.

It has been surprisingly found that the content of the pharmacologically active compound in the tablet and in the coated particulates, respectively, can be optimized in order to provide the best compromise between tamper-resistance, disintegration time and drug release, drug load, processability (especially tablettability) and patient compliance.

The pharmacologically active compound is present in the tablet in a therapeutically effective amount. The amount that constitutes a therapeutically effective amount varies according to the active ingredients being used, the condition being treated, the severity of said condition, the patient being treated, and the frequency of administration.

The content of the pharmacologically active compound in the tablet is not limited. The dose of the pharmacologically active compound which is adapted for administration preferably is in the range of 0.1 mg to 500 mg, more preferably in the range of 1.0 mg to 400 mg, even more preferably in the range of 5.0 mg to 300 mg, and most preferably in the range of 10 mg to 250 mg. In a preferred embodiment, the total amount of the pharmacologically active compound that is contained in the tablet is within the range of from 0.01 to 200 mg, more preferably 0.1 to 190 mg, still more preferably 1.0 to 180 mg, yet more preferably 1.5 to 160 mg, most preferably 2.0 to 100 mg and in particular 2.5 to 80 mg.

Preferably, the content of the pharmacologically active compound is within the range of from 0.01 to 80 wt.-%, more preferably 0.1 to 50 wt.-%, still more preferably 1 to 25 wt.-%, based on the total weight of the tablet.

In a preferred embodiment, the content of pharmacologically active compound is within the range of from 5.0±4.5 wt.-%, or 7.5±7.0 wt.-%, or 10±9.0 wt.-%, or 12.5±12.0 wt.-%, or 15±14 wt.-%, or 17.5±17.0 wt.-%, or 20±19 wt.-%, or 22.5±22.0 wt.-%, or 25±24 wt.-%; more preferably 5.0±4.0 wt.-%, or 7.5±6.0 wt.-%, or 10±8.0 wt.-%, or 12.5±12.0 wt.-%, or 15±12 wt.-%, or 17.5±15.0 wt.-%, or 20±19 wt.-%, or 22.5±22.0 wt.-%, or 25±24 wt.-%; still more preferably 5.0±3.5 wt.-%, or 7.5±5.0 wt.-%, or 10±7.0 wt.-%, or 12.5±10.0 wt.-%, or 15±10 wt.-%, or 17.5±13.0 wt.-%, or 20±17 wt.-%, or 22.5±19.0 wt.-%, or 25±21 wt.-%; yet more preferably 5.0±3.0 wt.-%, or 7.5±4.0 wt.-%, or 10±6.0 wt.-%, or 12.5±8.0 wt.-%, or 15±8.0 wt.-%, or 17.5±11.0 wt.-%, or 20±15 wt.-%, or 22.5±16.0 wt.-%, or 25±18 wt.-%; even more preferably 5.0±2.5 wt.-%, or 7.5±3.0 wt.-%, or 10±5.0 wt.-%, or 12.5±6.0 wt.-%, or 15±6.0 wt.-%, or 17.5±9.0 wt.-%, or 20±13 wt.-%, or 22.5±13.0 wt.-%, or 25±15 wt.-%; most preferably 5.0±2.0 wt.-%, or 7.5±2.0 wt.-%, or 10±4.0 wt.-%, or 12.5±4.0 wt.-%, or 15±4.0 wt.-%, or 17.5±7.0 wt.-%, or 20±11 wt.-%, or 22.5±10.0 wt.-%, or 25±12 wt.-%; and in particular 5.0±1.5 wt.-%, or 7.5±1.0 wt.-%, or 10±3.0 wt.-%, or 12.5±2.0 wt.-%, or 15±2.0 wt.-%, or 17.5±5.0 wt.-%, or 20±9 wt.-%, or 22.5±7.0 wt.-%, or 25±9 wt.-%; in each case based on the total weight of the tablet.

In a further preferred embodiment, the content of pharmacologically active compound is within the range of from 20±6 wt.-%, more preferably 20±5 wt.-%, still more preferably 20±4 wt.-%, most preferably 20±3 wt.-%, and in particular 20±2 wt.-%, based on the total weight of the tablet. In another preferred embodiment, the content of pharmacologically active compound is within the range of from 25±6 wt.-%, more preferably 25±5 wt.-%, still more preferably 25±4 wt.-%, most preferably 25±3 wt.-%, and in particular 25±2 wt.-%, based on the total weight of the tablet.

The skilled person may readily determine an appropriate amount of pharmacologically active compound to include in a tablet. For instance, in the case of analgesics, the total amount of pharmacologically active compound present in the tablet is that sufficient to provide analgesia. The total amount of pharmacologically active compound administered to a patient in a dose will vary depending on numerous factors including the nature of the pharmacologically active compound, the weight of the patient, the severity of the pain, the nature of other therapeutic agents being administered etc.

In a preferred embodiment, the pharmacologically active compound is contained in the tablet in an amount of 7.5±5 mg, 10±5 mg, 20±5 mg, 30±5 mg, 40±5 mg, 50±5 mg, 60±5 mg, 70±5 mg, 80±5 mg, 90±5 mg, 100±5 mg, 110±5 mg, 120±5 mg, 130±5, 140±5 mg, 150±5 mg, 160±5 mg, 170±5 mg, 180±5 mg, 190±5 mg, 200±5 mg, 210±5 mg, 220±5 mg, 230±5 mg, 240±5 mg, 250±5 mg, 260±5 mg, 270±5 mg, 280±5 mg, 290±5 mg, or 300±5 mg. In another preferred embodiment, the pharmacologically active compound is contained in the tablet in an amount of 5±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, 160±2.5 mg, 165±2.5 mg, 170±2.5 mg, 175±2.5 mg, 180±2.5 mg, 185±2.5 mg, 190±2.5 mg, 195±2.5 mg, 200±2.5 mg, 205±2.5 mg, 210±2.5 mg, 215±2.5 mg, 220±2.5 mg, 225±2.5 mg, 230±2.5 mg, 235±2.5 mg, 240±2.5 mg, 245±2.5 mg, 250±2.5 mg, 255±2.5 mg, 260±2.5 mg, or 265±2.5 mg.

In a particularly preferred embodiment, the pharmacologically active compound is tapentadol, preferably its HCl salt, and the tablet is adapted for administration once daily, twice daily, thrice daily or more frequently. In this embodiment, pharmacologically active compound is preferably contained in the tablet in an amount of from 25 to 100 mg.

In a particularly preferred embodiment, the pharmacologically active compound is oxymorphone, preferably its HCl salt, and the tablet is adapted for administration once daily, twice daily, thrice daily or more frequently. In this embodiment, the pharmacologically active compound is preferably contained in the tablet in an amount of from 5 to 40 mg. In another particularly preferred embodiment, the pharmacologically active compound is oxymorphone, preferably its HCl salt, and the tablet is adapted for administration once daily. In this embodiment, the pharmacologically active compound is preferably contained in the tablet in an amount of from 10 to 80 mg.

In another particularly preferred embodiment, the pharmacologically active compound is oxycodone, preferably its HCl salt, and the tablet is adapted for administration once daily, twice daily, thrice daily or more frequently. In this embodiment, the pharmacologically active compound is preferably contained in the tablet in an amount of from 5 to 80 mg.

In still another particularly preferred embodiment, the pharmacologically active compound is hydromorphone, preferably its HCl, and the tablet is adapted for administration once daily, twice daily, thrice daily or more frequently. In this embodiment, the pharmacologically active compound is preferably contained in the tablet in an amount of from 2 to 52 mg. In another particularly preferred embodiment, the pharmacologically active compound is hydromorphone, preferably its HCl, and the tablet is adapted for administration once daily, twice daily, thrice daily or more frequently. In this embodiment, the pharmacologically active compound is preferably contained in the tablet in an amount of from 4 to 104 mg.

The coated particulates present in the tablets according to the invention preferably comprise 3 to 75 wt.-% of pharmacologically active compound, more preferably 5 to 70 wt.-% of pharmacologically active compound, still more preferably 7.5 to 65 wt.-% of pharmacologically active compound, based on the total weight of a particulate.

Preferably, the content of the pharmacologically active compound is at least 25 wt.-%, more preferably at least 30 wt.-%, still more preferably at least 35 wt.-%, yet more preferably at least 40 wt.-%, most preferably at least 45 wt.-%, based on the total weight of a particulate.

Preferably, the content of the pharmacologically active compound is at most 70 wt.-%, more preferably at most 65 wt.-%, still more preferably at most 60 wt.-%, yet more preferably at most 55 wt.-%, most preferably at most 50 wt.-%, based on the total weight of a particulate.

In a preferred embodiment, the content of the pharmacologically active compound is within the range of 35±30 wt.-%, more preferably 35±25 wt.-%, still more preferably 35±20 wt.-%, yet more preferably 35±15 wt.-%, most preferably 35±10 wt.-%, and in particular 35±5 wt.-%, based on the total weight of a particulate. In another preferred embodiment, the content of the pharmacologically active compound is within the range of 45±30 wt.-%, more preferably 45±25 wt.-%, still more preferably 45±20 wt.-%, yet more preferably 45±15 wt.-%, most preferably 45±10 wt.-%, and in particular 45±5 wt.-%, based on the total weight of a particulate. In still another preferred embodiment, the content of the pharmacologically active compound is within the range of 55±30 wt.-%, more preferably 55±25 wt.-%, still more preferably 55±20 wt.-%, yet more preferably 55±15 wt.-%, most preferably 55±10 wt.-%, and in particular 55±5 wt.-%, based on the total weight of a particulate.

The pharmacologically active compound that is included in the preparation of the tablets according to the invention preferably has an average particle size of less than 500 microns, still more preferably less than 300 microns, yet more preferably less than 200 or 100 microns. There is no lower limit on the average particle size and it may be, for example, 50 microns. The particle size of pharmacologically active compounds may be determined by any technique conventional in the art, e.g. laser light scattering, sieve analysis, light microscopy or image analysis. Generally speaking it is preferable that the largest dimension of the pharmacologically active compound particle be less than the size of the coated particulates (e.g. less than the smallest dimension of the coated particulates).

A skilled person knows how to determine pharmacokinetic parameters such as $t_{1/2}$, $T_{max}$, $C_{max}$, AUC and bioavailability. For the purposes of the description, the pharmacokinetic parameters, which may be determined from the blood plasma concentrations of 3-(2-dimethylaminomethyl-cyclohexyl)phenol, are defined as follows:

| | |
|---|---|
| $C_{max}$ | maximum measured plasma concentration of the active ingredient after single administration (=average peak plasma level) |
| $t_{max}$ | interval of time from administration of the active ingredient until $C_{max}$ is reached |
| AUC | total area of the plasma concentration/time curve including the subarea from the final measured value extrapolated to infinity |
| $t_{1/2}$ | half-life |

The above parameters are in each case stated as mean values of the individual values for all investigated patients/test subjects.

A person skilled in the art knows how the pharmacokinetic parameters of the active ingredient may be calculated from the measured concentrations of the active ingredient in the blood plasma. In this connection, reference may be made, for example, to Willi Cawello (ed.) *Parameters for Compartment-free Pharmacokinetics*, Shaker Verlag Aachen (1999).

In a preferred embodiment, the pharmacologically active compound is tapentadol or a physiologically acceptable salt thereof, e.g. the hydrochloride. Preferably, the tablet according to the invention provides a mean absolute bioavailability of of tapentadol at least 22%, more preferably at least 24%, still more preferably at least 26%, yet more preferably at least 28%, most preferably at least 30%, and in particular at least 32%. $T_{max}$ of tapentadol is preferably within the range of 1.25±1.20 h, more preferably 1.25±1.00 h, still more preferably 1.25±0.80 h, yet more preferably 1.25±0.60 h, most preferably 1.25±0.40 h, and in particular 1.25±0.20 h. $t_{1/2}$ of tapentadol is preferably within the range of 4.0±2.8 h, more preferably 4.0±2.4 h, still more preferably 4.0±2.0 h, yet more preferably 4.0±1.6 h, most preferably 4.0±1.2 h, and in particular 4.0±0.8 h. Preferably, when normalized to a dose of 100 mg tapentadol, $C_{max}$ of tapentadol is preferably within the range of 90±85 ng/mL, more preferably 90±75 ng/mL, still more preferably 90±65 ng/mL, yet more preferably 90±55 ng/mL, most preferably 90±45 ng/mL, and in particular 90±35 ng/mL; and/or AUC of tapentadol is preferably within the range of 420±400 ng/mL·h, more preferably 420±350 ng/mL·h, still more preferably 420±300 ng/mL·h, yet more preferably 420±250 ng/mL·h, most preferably 420±200 ng/mL·h, and in particular 420±150 ng/mL·h.

In another preferred embodiment, the pharmacologically active compound is oxymorphone or a physiologically acceptable salt thereof, e.g. the hydrochloride. Preferably, the tablet according to the invention provides a mean absolute bioavailability of oxymorphone of at least 1%, more preferably at least 2%, still more preferably at least 4%, yet more preferably at least 6%, most preferably at least 8%, and in particular at least 10%. $T_{max}$ of oxymorphone is preferably within the range of 0.5±0.45 h, more preferably 0.5±0.40 h, still more preferably 0.5±0.35 h, yet more preferably 0.5±0.30 h, most preferably 0.5±0.25 h, and in particular 0.5±0.20 h. $t_{1/2}$ of oxymorphone is preferably within the range of 9.5±8.0 h, more preferably 9.5±7.0 h, still more preferably 9.5±6.0 h, yet more preferably 9.5±5.0 h, most preferably 9.5±4.0 h, and in particular 9.5±3.0 h. Preferably, when normalized to a dose of 20 mg oxymorphone, $C_{max}$ of oxymorphone is preferably within the range of 4.4±3.5 ng/mL, more preferably 4.4±3.0 ng/mL, still more preferably 4.4±2.5 ng/mL, yet more preferably 4.4±2.0 ng/mL, most preferably 4.4±1.5 ng/mL, and in particular 4.4±1.0 ng/mL; and/or AUC of oxymorphone is preferably within the range of 20.0±15.0 ng/mL·h, more preferably 20.0±12.5 ng/mL·h, still more preferably 20.0±10.0 ng/mL·h, yet more preferably 20.0±7.5 ng/mL·h, most preferably 20.0±6.0 ng/mL·h, and in particular 20.0±5.0 ng/mL·h.

In another preferred embodiment, the pharmacologically active compound is oxycodone or a physiologically acceptable salt thereof, e.g. the hydrochloride. Preferably, the tablet according to the invention provides a mean absolute bioavailability of oxycodone of at least 40%, more preferably at least 45%, still more preferably at least 50%, yet more preferably at least 55%, most preferably at least 60%, and in particular at least 70%. $T_{max}$ of oxycodone is preferably within the range of 2.6±2.5 h, more preferably 2.6±2.0 h, still more preferably 2.6±1.8 h, yet more preferably 2.6±0.1.6 h, most preferably 2.6±1.4 h, and in particular 2.6±1.20 h. $t_{1/2}$ of oxycodone is preferably within the range of 3.8±3.5 h, more preferably 3.8±3.0 h, still more preferably 3.8±2.5 h, yet more preferably 3.8±2.0 h, most preferably 3.8±1.5 h, and in particular 3.8±1.0 h. Preferably, when normalized to a dose of 30 mg oxycodone, $C_{max}$ of oxycodone is preferably within the range of 40±35 ng/mL, more preferably 40±30 ng/mL, still more preferably 40±25 ng/mL, yet more preferably 40±20 ng/mL, most preferably 40±15 ng/mL, and in particular 40±10 ng/mL; and/or AUC of oxycodone is preferably within the range of 270±250 ng/mL·h, more preferably 270±200 ng/mL·h, still more preferably 270±150 ng/mL·h, yet more preferably 270±100 ng/mL·h, most preferably 270±75 ng/mL·h, and in particular 270±50 ng/mL·h.

In still another preferred embodiment, the pharmacologically active compound is morphine or a physiologically acceptable salt thereof, e.g. the sulfate. Preferably, the tablet according to the invention provides a mean absolute bioavailability of morphine of at least 15%, more preferably at least 20%, still more preferably at least 25%, yet more preferably at least 30%, most preferably at least 35%, and in particular at least 40%. $T_{max}$ of morphine is preferably within the range of 0.625±0.60 h, more preferably 0.625±0.50 h, still more preferably 0.625±0.40 h, yet more preferably 0.625±0.30 h, most preferably 0.625±0.20 h, and in particular 0.625±0.15 h. Preferably, when normalized to a dose of 30 mg morphine sulfate, $C_{max}$ of morphine is preferably within the range of 25±20 ng/mL, more preferably 25±15 ng/mL, still more preferably 25±10 ng/mL, yet more preferably 25±5 ng/mL; and/or AUC of morphine is preferably within the range of 50±45 ng/mL·h, more preferably 50±40 ng/mL·h, still more preferably 50±35 ng/mL·h, yet more preferably 50±30 ng/mL·h, most preferably 50±25 ng/mL·h, and in particular 50±20 ng/mL·h.

The tablets according to the invention may also comprise one or more additional pharmacologically active compounds. The additional pharmacologically active compound may be susceptible to abuse or another pharmaceutical. Additional pharmacologically active compounds may be present within the coated particulates ("intragranular") or within the matrix (e.g. "extragranular", or when the matrix material is also provided in form of particulates, also "intragranular"). Where an additional pharmacologically active compound is present intragranularly, it may be present either in combination with one or more pharmacologically active compounds within the same particulates or in a discrete population of particulates alone and separate from any other pharmacologically active compounds present in the tablet.

In a preferred embodiment, the tablet according to the invention, preferably the coated particulates comprise an opioid (agonist) as well as an opioid antagonist.

Any conventional opioid antagonist may be present, e.g. naltrexone or naloxone or their pharmaceutically acceptable salts. Naloxone, including its salts, is particularly preferred. The opioid antagonist may be present within the coated particulates or within the matrix. Alternatively, opioid antagonist may be provided in separate particulates to the pharmacologically active compounds. The preferred composition of such particulates is the same as that described for pharmacologically active compound-containing particulates.

The ratio of opioid agonist to opioid antagonist in the tablets according to the invention is preferably 1:1 to 3:1 by weight, for example, about 2:1 by weight.

In another preferred embodiment, neither the coated particulates nor the tablet comprise any opioid antagonist.

The coated particulates according to the invention contain a physiologically acceptable polymer, preferably a polyalkylene oxide.

Preferably, the physiologically acceptable polymer is selected from the group consisting of polyalkylene oxide, preferably polymethylene oxide, polyethylene oxide, polypropylene oxide; polyethylene, polypropylene, polyvinyl chloride, polycarbonate, polystyrene, polyvinylpyrrolidone, poly(alk)acrylate, poly(hydroxy fatty acids), such as for example poly(3-hydroxybutyrate-co-3-hydroxyvalerate) (Biopol®), poly(hydroxyvaleric acid); polycaprolactone, polyvinyl alcohol, polyesteramide, polyethylene succinate, polylactone, polyglycolide, polyurethane, polyamide, polylactide, polyacetal (for example polysaccharides optionally with modified side chains), polylactide/glycolide, polylactone, polyglycolide, polyorthoester, polyanhydride, block polymers of polyethylene glycol and polybutylene terephthalate (Polyactive®), polyanhydride (Polifeprosan), copolymers thereof, block-copolymers thereof (e.g., Poloxamer®), and mixtures of at least two of the stated polymers, or other polymers with the above characteristics. Polyalkylene oxide is particularly preferred.

Preferably, the physiologically acceptable polymer is a polyalkylene oxide, more preferably selected from polymethylene oxide, polyethylene oxide and polypropylene oxide, or copolymers thereof. Polyethylene oxide is preferred.

In a preferred embodiment, the physiologically acceptable polymer, preferably the polyalkylene oxide has a weight average molecular weight ($M_W$) or viscosity average molecular weight ($M_\eta$) of at least 200,000 or at least 500,000 g/mol, preferably at least 1,000,000 g/mol or at least 2,500,000 g/mol, more preferably in the range of about 1,000,000 g/mol to about 15,000,000 g/mol, and most preferably in the range of about 5,000,000 g/mol to about 10,000,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

The physiologically acceptable polymer, preferably the polyalkylene oxide may comprise a single polymer having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

For the purpose of specification, a polyalkylene glycol has a molecular weight of up to 20,000 g/mol whereas a polyalkylene oxide has a molecular weight of more than 20,000 g/mol. In a preferred embodiment, the weight average over all molecular weights of all polyalkylene oxides that are contained in the tablet is at least 200,000 g/mol. Thus, polyalkylene glycols, if any, are preferably not taken into consideration when determining the weight average molecular weight of polyalkylene oxide.

In a preferred embodiment, the physiologically acceptable polymer, preferably the polyalkylene oxide is homogeneously distributed in the coated particulates according to the invention. Preferably, the pharmacologically active compound and the physiologically acceptable polymer, preferably the polyalkylene oxide are intimately homogeneously distributed in the coated particulates so that the coated particulates do not contain any segments where either pharmacologically active compound is present in the absence of physiologically acceptable polymer, preferably polyalkylene oxide or where physiologically acceptable polymer, preferably polyalkylene oxide is present in the absence of pharmacologically active compound.

The particulates are film coated and the physiologically acceptable polymer, preferably the polyalkylene oxide is preferably homogeneously distributed in the core of the coated particulates, i.e. the film coating preferably does not contain physiologically acceptable polymer, preferably polyalkylene oxide. Nonetheless, the film coating as such may of course contain one or more polymers, which however, preferably differ from the physiologically acceptable polymer, preferably the polyalkylene oxide contained in the core.

The physiologically acceptable polymer, preferably the polyalkylene oxide may be combined with one or more different polymers selected from the group consisting of polyalkylene oxide, preferably polymethylene oxide, polyethylene oxide, polypropylene oxide; polyethylene, polypropylene, polyvinyl chloride, polycarbonate, polystyrene, polyvinylpyrrolidone, poly(alk)acrylate, poly(hydroxy fatty acids), such as for example poly(3-hydroxybutyrate-co-3-hydroxyvalerate) (Biopol®), poly(hydroxyvaleric acid); polycaprolactone, polyvinyl alcohol, polyesteramide, polyethylene succinate, polylactone, polyglycolide, polyurethane, polyamide, polylactide, polyacetal (for example polysaccharides optionally with modified side chains), polylactide/glycolide, polylactone, polyglycolide, polyorthoester, polyanhydride, block polymers of polyethylene glycol and polybutylene terephthalate (Polyactive®), polyanhydride (Polifeprosan), copolymers thereof, block-copolymers thereof (e.g., Poloxamer®), and mixtures of at least two of the stated polymers, or other polymers with the above characteristics.

Preferably, the molecular weight dispersity $M_w/M_\eta$ of the physiologically acceptable polymer, preferably the polyalkylene oxide is within the range of 2.5±2.0, more preferably 2.5±1.5, still more preferably 2.5±1.0, yet more preferably 2.5±0.8, most preferably 2.5±0.6, and in particular 2.5±0.4.

The physiologically acceptable polymer, preferably the polyalkylene oxide preferably has a viscosity at 25° C. of 30 to 17,600 cP, more preferably 55 to 17,600 cP, still more preferably 600 to 17,600 cP and most preferably 4,500 to 17,600 cP, measured in a 5 wt.-% aqueous solution using a model RVF Brookfield viscosimeter (spindle no. 2/rotational speed 2 rpm); of 400 to 4,000 cP, more preferably 400 to 800 cP or 2,000 to 4,000 cP, measured on a 2 wt.-% aqueous solution using the stated viscosimeter (spindle no. 1 or 3/rotational speed 10 rpm); or of 1,650 to 10,000 cP, more preferably 1,650 to 5,500 cP, 5,500 to 7,500 cP or 7,500 to 10,000 cP, measured on a 1 wt.-% aqueous solution using the stated viscosimeter (spindle no. 2/rotational speed 2 rpm).

Polyethylene oxide that is suitable for use in the tablets according to the invention is commercially available from Dow. For example, Polyox WSR N-12K, Polyox N-60K, Polyox WSR 301 NF or Polyox WSR 303NF may be used in the tablets according to the invention. For details concerning the properties of these products, it can be referred to e.g. the product specification.

Preferably, the content of the physiologically acceptable polymer, preferably the polyalkylene oxide is within the range of from 1 to 60 wt.-%, more preferably 3 to 55 wt.-%, still more preferably 5 to 50 wt.-%, yet more preferably 7 to 45 wt.-%, most preferably 10 to 40 wt.-% and in particular 15 to 35 wt.-%, based on the total weight of the tablet. In a preferred embodiment, the content of the physiologically acceptable polymer, preferably the polyalkylene oxide is at least 2 wt.-%, more preferably at least 5 wt.-%, still more preferably at least 10 wt.-%, yet more preferably at least 15 wt.-% and in particular at least 20 wt.-%, based on the total weight of the tablet.

In a preferred embodiment, the overall content of physiologically acceptable polymer, preferably polyalkylene oxide is within the range of 10±8 wt.-%, more preferably 10±6 wt.-%, most preferably 10±4 wt.-%, and in particular 10±2 wt.-%, based on the total weight of the tablet. In another preferred embodiment, the overall content of physiologically acceptable polymer, preferably polyalkylene oxide is within the range of 15±12 wt.-%, more preferably 15±10 wt.-%, most preferably 15±7 wt.-%, and in particular 15±3 wt.-%, based on the total weight of the tablet. In still another preferred embodiment, the overall content of physiologically acceptable polymer, preferably polyalkylene oxide is within the range of 20±16 wt.-%, more preferably 20±12 wt.-%, most preferably 20±8 wt.-%, and in particular 20±4 wt.-%, based on the total weight of the tablet. In yet another preferred embodiment, the overall content of physiologically acceptable polymer, preferably polyalkylene oxide is within the range of 25±20 wt.-%, more preferably 25±15 wt.-%, most preferably 25±10 wt.-%, and in particular 25±5 wt.-%, based on the total weight of the tablet. In a further preferred embodiment, the overall content of physiologically acceptable polymer, preferably polyalkylene oxide is within the range of 30±20 wt.-%, more preferably 30±15 wt.-%, most preferably 30±10 wt.-%, and in particular 30±5 wt.-%, based on the total weight of the tablet. In still a further a preferred embodiment, the overall content of physiologically acceptable polymer, preferably polyalkylene oxide is within the range of 35±20 wt.-%, more preferably 35±15 wt.-%, most preferably 35±10 wt.-%, and in particular 35±5 wt.-%. In a still further a preferred embodiment, the overall content of physiologically acceptable polymer, preferably polyalkylene oxide is within the range of 40±20 wt.-%, more preferably 40±15 wt.-%, and most preferably 40±10 wt.-%, and in particular 40±5 wt.-%, based on the total weight of the tablet.

Preferably, the content of the physiologically acceptable polymer, preferably the polyalkylene oxide is within the range of from 1 to 99 wt.-%, more preferably 5 to 95 wt.-%, still more preferably 10 to 90 wt.-%, yet more preferably 15 to 85 wt.-%, most preferably 20 to 80 wt.-% and in particular 25 to 75 wt.-%, based on the total weight of the coated particulates. In a preferred embodiment, the content of the physiologically acceptable polymer, preferably the polyalkylene oxide is at least 10 wt.-%, more preferably at least 15 wt.-%, still more preferably at least 20 wt.-%, yet more preferably at least 25 wt.-% and in particular at least 30 wt.-%, based on the total weight of the coated particulates.

In a preferred embodiment, the overall content of physiologically acceptable polymer, preferably polyalkylene oxide is within the range of 30±20 wt.-%, more preferably 30±15 wt.-%, most preferably 30±10 wt.-%, and in particular 30±5 wt.-%, based on the total weight of the coated particulates. In another preferred embodiment, the overall content of physiologically acceptable polymer, preferably polyalkylene oxide is within the range of 35±20 wt.-%, more preferably 35±15 wt.-%, most preferably 35±10 wt.-%, and in particular 35±5 wt.-%, based on the total weight of the coated particulates. In still another preferred embodiment, the overall content of physiologically acceptable polymer, preferably polyalkylene oxide is within the range of 40±20 wt.-%, more preferably 40±15 wt.-%, most preferably 40±10 wt.-%, and in particular 40±5 wt.-%, based on the total weight of the coated particulates. In yet another preferred embodiment, the overall content of physiologically acceptable polymer, preferably polyalkylene oxide is within the range of 45±20 wt.-%, more preferably 45±15 wt.-%, most preferably 45±10 wt.-%, and in particular 45±5 wt.-%, based on the total weight of the coated particulates. In a further preferred embodiment, the overall content of physiologically acceptable polymer, preferably polyalkylene oxide is within the range of 50±20 wt.-%, more preferably 50±15 wt.-%, most preferably 50±10 wt.-%, and in particular 50±5 wt.-%, based on the total weight of the coated particulates. In still a further a preferred embodiment, the overall content of physiologically acceptable polymer, preferably polyalkylene oxide is within the range of 55±20 wt.-%, more preferably 55±15 wt.-%, most preferably 55±10 wt.-%, and in particular 55±5 wt.-%. In a still further a preferred embodiment, the overall content of physiologically acceptable polymer, preferably polyalkylene oxide is within the range of 60±15 wt.-%, more preferably 60±10 wt.-%, most preferably 60±5 wt.-%, and in particular 60±5 wt.-%, based on the total weight of the coated particulates.

Preferably, the relative weight ratio of the physiologically acceptable polymer, preferably the polyalkylene oxide to the pharmacologically active compound is within the range of 1:1.00±0.75, more preferably 1:1.00±0.50, still more preferably 1:1.00±0.40, yet more preferably 1:1.00±0.30, most preferably 1:1.00±0.20, and in particular 1:1.00±0.10.

The coated particulates according to the invention may contain additional pharmaceutical excipients conventionally contained in tablets in conventional amounts, such as antioxidants, preservatives, lubricants, plasticizer, fillers, binders, and the like.

The skilled person will readily be able to determine appropriate further excipients as well as the quantities of each of these excipients. Specific examples of pharmaceutically acceptable carriers and excipients that may be used to formulate the tablets according to the invention are described in the Handbook of Pharmaceutical Excipients, American Pharmaceutical Association (1986).

In a preferred embodiment, the coated particulates do not contain a disintegrant.

Preferably, the coated particulates further comprise an antioxidant. Suitable antioxidants include ascorbic acid, butylated hydroxyanisole (BHA), butylated hydroxytoluene (BHT), salts of ascorbic acid, monothioglycerol, phosphorous acid, vitamin C, vitamin E and the derivatives thereof, coniferyl benzoate, nordihydroguajaretic acid, gallus acid esters, sodium bisulfite, particularly preferably butylhydroxytoluene or butylhydroxyanisole and α-tocopherol. The antioxidant is preferably present in quantities of 0.01 wt.-% to 10 wt.-%, more preferably of 0.03 wt.-% to 5 wt.-%, most preferably of 0.05 wt.-% to 2.5 wt.-%, based on the total weight of the coated particulates.

In a preferred embodiment, the coated particulates further comprise an acid, preferably citric acid. The amount of acid is preferably in the range of 0.01 wt.-% to about 20 wt.-%, more preferably in the range of 0.02 wt.-% to about 10 wt.-%, and still more preferably in the range of 0.05 wt.-% to about 5 wt.-%, and most preferably in the range of 0.1 wt.-% to about 1.0 wt.-%, based on the total weight of the coated particulates.

In a preferred embodiment, the coated particulates further comprise another polymer which is preferably selected from cellulose esters and cellulose ethers, in particular hydroxypropyl methylcellulose (HPMC).

Other preferred polymers are polyvinyl caprolactam-polyvinyl acetate-polyethylene glycol graft co-polymers, such as the one commercially available under the trade name Soluplus®.

The amount of the further polymer, preferably hydroxypropyl methylcellulose, preferably ranges from 0.1 wt.-% to about 30 wt.-%, more preferably in the range of 1.0 wt.-% to about 20 wt.-%, most preferably in the range of 2.0 wt.-% to about 15 wt.-%, and in particular in the range of 3.5 wt.-% to about 10.5 wt.-%, based on the total weight of the coated particulates.

In a preferred embodiment, the relative weight ratio of the physiologically acceptable polymer, preferably the polyalkylene oxide to the further polymer is within the range of 4.5±2:1, more preferably 4.5±1.5:1, still more preferably 4.5±1:1, yet more preferably 4.5±0.5:1, most preferably 4.5±0.2:1, and in particular 4.5±0.1:1. In another preferred embodiment, the relative weight ratio of the physiologically acceptable polymer, preferably the polyalkylene oxide to the further polymer is within the range of 8±7:1, more preferably 8±6:1, still more preferably 8±5:1, yet more preferably 8±4:1, most preferably 8±3:1, and in particular 8±2:1. In still another preferred embodiment, the relative weight ratio of the physiologically acceptable polymer, preferably the polyalkylene oxide to the further polymer is within the range of 11±8:1, more preferably 11±7:1, still more preferably 11±6:1, yet more preferably 11±5:1, most preferably 11±4:1, and in particular 11±3:1.

In another preferred embodiment, the coated particulates according to the invention do not contain any further polymer besides the physiologically acceptable polymer, preferably the polyalkylene oxide and optionally, polyethylene glycol.

In a preferred embodiment, the coated particulates contain at least one lubricant. In another preferred embodiment, the coated particulates contain no lubricant. Especially preferred lubricants are selected from magnesium stearate and stearic acid;

glycerides of fatty acids, including monoglycerides, diglycerides, triglycerides, and mixtures thereof; preferably of $C_6$ to $C_{22}$ fatty acids; especially preferred are partial glycerides of the $C_{16}$ to $C_{22}$ fatty acids such as glycerol behenat, glycerol palmitostearate and glycerol monostearate;

polyoxyethylene glycerol fatty acid esters, such as mixtures of mono-, di- and triesters of glycerol and di- and monoesters of macrogols having molecular weights within the range of from 200 to 4000 g/mol, e.g., macrogolglycerolcaprylocaprate, macrogolglycerollaurate, macrogolglycerolococoate, macrogolglycerollinoleate, macrogol-20-glycerolmonostearate, macrogol-6-glycerolcaprylocaprate, macrogolglycerololeate; macrogolglycerolstearate, macrogolglycerolhydroxystearate, and macrogolglycerolrizinoleate;

polyglycolyzed glycerides, such as the one known and commercially available under the trade name "Labrasol";

fatty alcohols that may be linear or branched, such as cetylalcohol, stearylalcohol, cetylstearyl alcohol, 2-octyldodecane-1-ol and 2-hexyldecane-1-ol;

polyethylene glycols having a molecular weight between 10.000 and 60.000 g/mol; and natural semi-synthetic or synthetic waxes, preferably waxes with a softening point of at least 50° C., more preferably 60° C., and in particular carnauba wax and bees wax.

Preferably, the amount of the lubricant ranges from 0.01 wt.-% to about 10 wt.-%, more preferably in the range of 0.05 wt.-% to about 7.5 wt.-%, most preferably in the range of 0.1 wt.-% to about 5 wt.-%, and in particular in the range of 0.1 wt.-% to about 1 wt.-%, based on the total weight of the coated particulates.

Preferably, the coated particulates further comprise a plasticizer. The plasticizer improves the processability of the physiologically acceptable polymer, preferably the polyalkylene oxide. A preferred plasticizer is polyalkylene glycol, like polyethylene glycol, triacetin, fatty acids, fatty acid esters, waxes and/or microcrystalline waxes. Particularly preferred plasticizers are polyethylene glycols, such as PEG 6000.

Preferably, the content of the plasticizer is within the range of from 0.5 to 30 wt.-%, more preferably 1.0 to 25 wt.-%, still more preferably 2.5 wt.-% to 22.5 wt.-%, yet more preferably 5.0 wt.-% to 20 wt.-%, most preferably 6 to 20 wt.-% and in particular 7 wt.-% to 17.5 wt.-%, based on the total weight of the coated particulates.

In a preferred embodiment, the plasticizer is a polyalkylene glycol having a content within the range of 7±6 wt.-%, more preferably 7±5 wt.-%, still more preferably 7±4 wt.-%, yet more preferably 7±3 wt.-%, most preferably 7±2 wt.-%, and in particular 7±1 wt.-%, based on the total weight of the coated particulates.

In another preferred embodiment, the plasticizer is a polyalkylene glycol having a content within the range of 10±8 wt.-%, more preferably 10±6 wt.-%, still more preferably 10±5 wt.-%, yet more preferably 10±4 wt.-%, most preferably 10±3 wt.-%, and in particular 10±2 wt.-%, based on the total weight of the coated particulates.

In a preferred embodiment, the relative weight ratio of the physiologically acceptable polymer, preferably the polyalkylene oxide to the polyalkylene glycol is within the range of 5.4±2:1, more preferably 5.4±1.5:1, still more preferably 5.4±1:1, yet more preferably 5.4±0.5:1, most preferably 5.4±0.2:1, and in particular 5.4±0.1:1. This ratio satisfies the requirements of relative high polymer content and good extrudability.

Plasticizers can sometimes act as a lubricant, and lubricants can sometimes act as a plasticizer.

The coated particulates and the matrix material of the tablets according to the invention preferably do not contain any polymers selected from the group consisting of acrylates (such as acrylic and methacrylic polymers including acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers; e.g., Eudragit® NE, NM, RS or RL).

alkylcelluloses and hydroxy alkyl celluloses (such as methylcellulose, ethylcellulose, hydroxy propyl cellulose and hydroxylpropyl methylcellulose); and gelling agents which hydrate to form gels to control the movement of water, such as high molecular weight grade (high viscosity) hydroxypropylmethyl cellulose (HPMC), pectin, locust bean gum and xanthan gum.

In a preferred embodiment, the tablet according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding active compound, for example due to increased nasal secretion or sneezing. Further examples of substances which irritate the nasal passages and/or pharynx are those which cause burning, itching, urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance drug. Corresponding hot substance drugs are known per se to the person skilled in the art and are described, for example, in "Pharmazeutische Biologie—Drogen und ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure.

The tablet according to the invention furthermore preferably contains no antagonists for the pharmacologically active compound, preferably no antagonists against psychotropic substances, in particular no antagonists against opioids. Antagonists suitable for a given pharmacologically active compound are known to the person skilled in the art and may be present as such or in the form of corresponding derivatives, in particular esters or ethers, or in each case in the form of corresponding physiologically acceptable compounds, in particular in the form of the salts or solvates thereof. The tablet according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

The tablet according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The tablet according to the invention preferably contains no emetic based on one or more constituents of ipecacuanha (ipecac) root, for example based on the constituent emetine, as are, for example, described in "Pharmazeutische Biologie—Drogen und ihre Inhaltsstoffe" by Prof. Dr. Hildebert Wagner, 2nd, revised edition, Gustav Fischer Verlag, Stuttgart, N.Y., 1982. The corresponding literature description is hereby introduced as a reference and is deemed to be part of the disclosure. The tablet according to the invention preferably also contains no apomorphine as an emetic.

Finally, the tablet according to the invention preferably also contains no bitter substance. Bitter substances and the quantities effective for use may be found in US-2003/0064099 A1, the corresponding disclosure of which should be deemed to be the disclosure of the present application and is hereby introduced as a reference. Examples of bitter substances are aromatic oils, such as peppermint oil, eucalyptus oil, bitter almond oil, menthol, fruit aroma substances, aroma substances from lemons, oranges, limes, grapefruit or mixtures thereof, and/or denatonium benzoate.

The tablet according to the invention accordingly preferably contains neither substances which irritate the nasal passages and/or pharynx, nor antagonists for the pharmacologically active compound, nor emetics, nor bitter substances.

Particularly preferred contents of pharmacologically active compound, physiologically acceptable polymer, preferably polyalkylene oxide, plasticizer and antioxidant of the coated particulates, relative to the total weight of the coated particulates, are summarized as embodiments $B^1$ to $B^6$ in the table here below:

| wt.-% | $B^1$ | $B^2$ | $B^3$ | $B^4$ | $B^5$ | $B^6$ |
|---|---|---|---|---|---|---|
| active compound | 45 ± 30 | 45 ± 25 | 45 ± 20 | 45 ± 15 | 45 ± 10 | 45 ± 5 |
| polymer | 45 ± 30 | 45 ± 25 | 45 ± 20 | 45 ± 15 | 45 ± 10 | 45 ± 5 |
| plasticizer | 8 ± 6 | 8 ± 5 | 8 ± 4 | 8 ± 3 | 8 ± 2 | 8 ± 1 |
| antioxidant | 0.10 ± 0.08 | 0.10 ± 0.06 | 0.10 ± 0.04 | 0.10 ± 0.03 | 0.10 ± 0.02 | 0.10 ± 0.01 |
| coating | 4.5 ± 3.7 | 4.5 ± 3.5 | 4.5 ± 3.0 | 4.5 ± 2.5 | 4.5 ± 2.0 | 4.5 ± 1.5 | wherein the pharmacologically active compound is preferably an opioid, particularly preferably tapentadol or a physiologically acceptable salt thereof; the polymer is preferably a polyalkylene oxide, more preferably a polyethylene oxide having a weight average molecular weight of at least 500,000 g/mol; the plasticizer preferably is a poylethylene glycol; and the antioxidant preferably is α-tocopherol.

Besides the coated particulates and the preferably pre-compacted or granulated matrix material, the tablet according to the invention may comprise one or more pharmaceutical excipients such as binders, fillers, lubricants and the like.

In a preferred embodiment, the table additionally comprises a lubricant. Magnesium stearate is preferred. Further preferred lubricants are described above and therefore are not repeated hereinafter.

If the tablet contains an additional lubricant outside the preferably pre-compacted or pre-granulated matrix material, its content is preferably not more than 1 wt.-%, more preferably not more than 0.5 wt.-%, based on the total weight of the tablet.

While the coated particulates that are contained in the tablet according to the invention preferably exhibit increased mechanical strength, the tablet as such preferably has conventional mechanical properties. Typically, the tablet according to the invention can be crushed e.g. by means of a hammer thereby yielding a fractured composition containing the matrix material, the coated particulates and any other ingredients contained in the tablet. However, the coated particulates thereby obtained in more or less isolated form preferably cannot be further crushed and fractured by means of a hammer.

Preferably, the coated particulates are hot melt-extruded and/or have a breaking strength of at least 300 N.

The tablet according to the invention is tamper-resistant. Preferably, tamper-resistance is achieved based on the mechanical properties of the coated particulates so that comminution is avoided or at least substantially impeded. According to the invention, the term comminution means the pulverization of the coated particulates using conventional means usually available to an abuser, for example a pestle and mortar, a hammer, a mallet or other conventional means for pulverizing under the action of force. Thus, tamper-resistance preferably means that pulverization of the coated particulates using conventional means is avoided or at least substantially impeded.

Preferably, the mechanical properties of the coated particulates according to the invention, particularly their breaking strength and deformability, substantially rely on the presence and spatial distribution of physiologically acceptable polymer, preferably polyalkylene oxide, although their mere presence does typically not suffice in order to achieve said properties. The advantageous mechanical properties of the coated particulates according to the invention may not automatically be achieved by simply processing pharmacologically active compound, physiologically acceptable polymer, preferably polyalkylene oxide, and optionally further excipients by means of conventional methods for the preparation of tablets. In fact, usually suitable apparatuses must be selected for the preparation and critical processing parameters must be adjusted, particularly pressure/force, temperature and time. Thus, even if conventional apparatuses are used, the process protocols usually must be adapted in order to meet the required criteria.

In general, the coated particulates exhibiting the desired properties may be obtained only if, during preparation of the particulates,
  suitable components
  in suitable amounts are exposed to a sufficient pressure at a sufficient temperature for a sufficient period of time.

Thus, regardless of the apparatus used, the process protocols must be adapted in order to meet the required criteria. Therefore, the breaking strength and deformability of the particulates is separable from the composition.

The coated particulates contained in the tablet according to the invention preferably have a breaking strength of at least 300 N, at least 400 N, or at least 500 N, preferably at least 600 N, more preferably at least 700 N, still more preferably at least 800 N, yet more preferably at least 1000 N, most preferably at least 1250 N and in particular at least 1500 N.

In order to verify whether a particulate exhibits a particular breaking strength of e.g. 300 N or 500 N it is typically not necessary to subject said particulate to forces much higher than 300 N and 500 N, respectively. Thus, the breaking strength test can usually be terminated once the force corresponding to the desired breaking strength has been slightly exceeded, e.g. at forces of e.g. 330 N and 550 N, respectively.

The "breaking strength" (resistance to crushing) of a tablet and of a particulate is known to the skilled person. In this regard it can be referred to, e.g., W. A. Ritschel, Die Tablette, 2. Auflage, Editio Cantor Verlag Aulendorf, 2002; H Liebermann et al., Tablets: Tablets, Vol. 2, Informa Healthcare; 2 edition, 1990; and Encyclopedia of Pharmaceutical Technology, Informa Healthcare; 1 edition.

For the purpose of specification, the breaking strength is preferably defined as the amount of force that is necessary in order to fracture the particulate (=breaking force). Therefore, for the purpose of specification a particulate does preferably not exhibit the desired breaking strength when it breaks, i.e., is fractured into at least two independent parts that are separated from one another. In another preferred embodiment, however, the particulate is regarded as being broken if the force decreases by 50% (threshold value) of the highest force measured during the measurement (see below).

For the purpose of specification, the mechanical properties of the coated particulates according to the invention essentially refer to the mechanical properties of the core of said coated particulates, but not to its coating. Thus, if the coated particulates according to the invention are exerted to an external force causing the coating material to separate partially of fully from the core, which in turn, however, is not disrupted, the coated particulates still exhibit the desired properties.

The coated particulates according to the invention are distinguished from conventional particulates that can be contained in tablets in that, due to their breaking strength, they cannot be pulverized by the application of force with conventional means, such as for example a pestle and mortar, a hammer, a mallet or other usual means for pulverization, in particular devices developed for this purpose (tablet crushers). In this regard "pulverization" means crumbling into small particles. Avoidance of pulverization virtually rules out oral or parenteral, in particular intravenous or nasal abuse.

Conventional particulates typically have a breaking strength well below 200 N.

The breaking strength of conventional round tablets/particulates may be estimated according to the following empirical formula: Breaking Strength [in N]=10×Diameter Of The Tablet/Particulate [in mm]. Thus, according to said empirical formula, a round tablet/particulate having a breaking strength of at least 300 N would require a diameter of at least 30 mm). Such a particulate, however, could not be swallowed, let alone a tablet containing a plurality of such particulates. The above empirical formula preferably does not apply to the coated particulates according to the invention, which are not conventional but rather special.

Further, the actual mean chewing force is about 220 N (cf., e.g., P. A. Proeschel et al., J Dent Res, 2002, 81(7), 464-468). This means that conventional particulates having a breaking strength well below 200 N may be crushed upon spontaneous chewing, whereas the coated particulates according to the invention may preferably not.

Still further, when applying a gravitational acceleration of about 9.81 m/s$^2$, 300 N correspond to a gravitational force of more than 30 kg, i.e. the coated particulates according to the invention can preferably withstand a weight of more than 30 kg without being pulverized.

Methods for measuring the breaking strength of a tablet are known to the skilled artisan. Suitable devices are commercially available.

For example, the breaking strength (resistance to crushing) can be measured in accordance with the Eur. Ph. 5.0, 2.9.8 or 6.0, 2.09.08 "Resistance to Crushing of Tablets". The test is intended to determine, under defined conditions, the resistance to crushing of tablets and particulates, respectively, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the tablet and particulate, respectively. The apparatus is calibrated using a system with a precision of 1 Newton. The tablet and particulate, respectively, is placed between the jaws, taking into account, where applicable, the shape, the break-mark and the inscription; for each measurement the tablet and particulate, respectively, is oriented in the same way with respect to the direction of application of the force (and the direction of extension in which the breaking strength is to be measured). The measurement is carried out on 10 tablets and particulates, respectively, taking care that all fragments have been removed before each determination. The result is expressed as the mean, minimum and maximum values of the forces measured, all expressed in Newton.

A similar description of the breaking strength (breaking force) can be found in the USP. The breaking strength can alternatively be measured in accordance with the method described therein where it is stated that the breaking strength is the force required to cause a tablet and particulate, respectively, to fail (i.e., break) in a specific plane. The tablets and particulates, respectively, are generally placed between two platens, one of which moves to apply sufficient force to the tablet and particulate, respectively, to cause fracture. For conventional, round (circular cross-section) tablets and particulates, respectively, loading occurs across their diameter (sometimes referred to as diametral loading), and fracture occurs in the plane. The breaking force of tablets and particulates, respectively, is commonly called hardness in the pharmaceutical literature; however, the use of this term is misleading. In material science, the term hardness refers to the resistance of a surface to penetration or indentation by a small probe. The term crushing strength is also frequently used to describe the resistance of tablets and particulate, respectively, to the application of a compressive load. Although this term describes the true nature of the test more accurately than does hardness, it implies that tablets and particulate, respectively, are actually crushed during the test, which is often not the case.

Alternatively, the breaking strength (resistance to crushing) can be measured in accordance with WO 2008/107149, which can be regarded as a modification of the method described in the Eur. Ph. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. A skilled person knows how to properly adjust the test speed, e.g. to 10 mm/min, 20 mm/min, or 40 mm/min, for example. Measurement is performed using a pressure piston with screw-in inserts and a cylinder (diameter 10 mm), a force transducer, $F_{max}$. 1 kN, diameter=8 mm, class 0.5 from 10 N, class 1 from 2 N to ISO 7500-1, with manufacturers test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centring device.

When using the testControl software (testXpert V10.11), the following exemplified settings and parameters have revealed to be useful: LE-position: clamping length 150 mm. LE-speed: 500 mm/min, clamping length after pre-travel: 195 mm, pre-travel speed: 500 mm/min, no pre-force control—pre-force: pre-force 1N, pre-force speed 10 mm/min—sample data: no sample form, measuring length traverse distance 10 mm, no input required prior to testing—testing/end of test; test speed: position-controlled 10 mm/min, delay speed shift: 1, force shut down threshold 50% $F_{max}$, no force threshold for break-tests, no max length variation, upper force limit: 600N—expansion compensation: no correction of measuring length—actions after testing: LE to be set after test, no unload of sample—TRS: data memory: TRS distance interval until break 1 μm, TRS time interval 0.1 s, TRS force interval 1N—machine; traverse distance controller: upper soft end 358 mm, lower soft end 192 mm—lower test space. Parallel arrangement of the upper plate and the ambos should be ensured—these parts must not touch during or after testing. After testing, a small gap (e.g. 0.1 or 0.2 mm) should still be present between the two brackets in intimated contact with the tested particulate, representing the remaining thickness of the deformed particulate.

In a preferred embodiment, the particulate is regarded as being broken if it is fractured into at least two separate pieces of comparable morphology. Separated matter having a morphology different from that of the deformed particulate, e.g. dust, is not considered as pieces qualifying for the definition of breaking.

The coated particulates according to the invention preferably exhibit mechanical strength over a wide temperature range, in addition to the breaking strength (resistance to crushing) optionally also sufficient hardness, yield strength, fatigue strength, impact resistance, impact elasticity, tensile strength, compressive strength and/or modulus of elasticity, optionally also at low temperatures (e.g. below −24° C., below −40° C. or possibly even in liquid nitrogen), for it to be virtually impossible to pulverize by spontaneous chewing, grinding in a mortar, pounding, etc. Thus, preferably, the comparatively high breaking strength of the particulate according to the invention is maintained even at low or very low temperatures, e.g., when the tablet is initially chilled to increase its brittleness, for example to temperatures below −25° C., below −40° C. or even in liquid nitrogen.

The particulate according to the invention is characterized by a certain degree of breaking strength. This does not mean that the particulate must also exhibit a certain degree of hardness. Hardness and breaking strength are different physical properties. Therefore, the tamper-resistance of the tablet does not necessarily depend on the hardness of the coated particulates. For instance, due to its breaking strength, impact strength, elasticity modulus and tensile strength, respectively, the coated particulates can preferably be deformed, e.g. plastically, when exerting an external force, for example using a hammer, but cannot be pulverized, i.e., crumbled into a high number of fragments. In other words, the coated particulates according to the invention are characterized by a certain degree of breaking strength, but not necessarily also by a certain degree of form stability.

Therefore, in the meaning of the specification, a particulate that is deformed when being exposed to a force in a particular direction of extension but that does not break (plastic deformation or plastic flow) is preferably to be regarded as having the desired breaking strength in said direction of extension.

Preferred particulates present in the tablets according to the invention are those having a suitable tensile strength as determined by a test method currently accepted in the art. Further preferred particulates are those having a Youngs Modulus as determined by a test method of the art. Still further preferred particulates are those having an acceptable elongation at break.

Irrespective of whether the particulates according to the invention have an increased breaking strength or nor, the particulates according to the invention preferably exhibit a certain degree of deformability. The particulates contained in the tablet according to the invention preferably have a deformability such that they show an increase, preferably a steady increase of the force at a corresponding decrease of the displacement in the force-displacement-diagram when being subjected to a breaking strength test as described above. This mechanical property, i.e. the deformability of the individual particulates, is illustrated in FIGS. 5 and 6.

Figure 5:
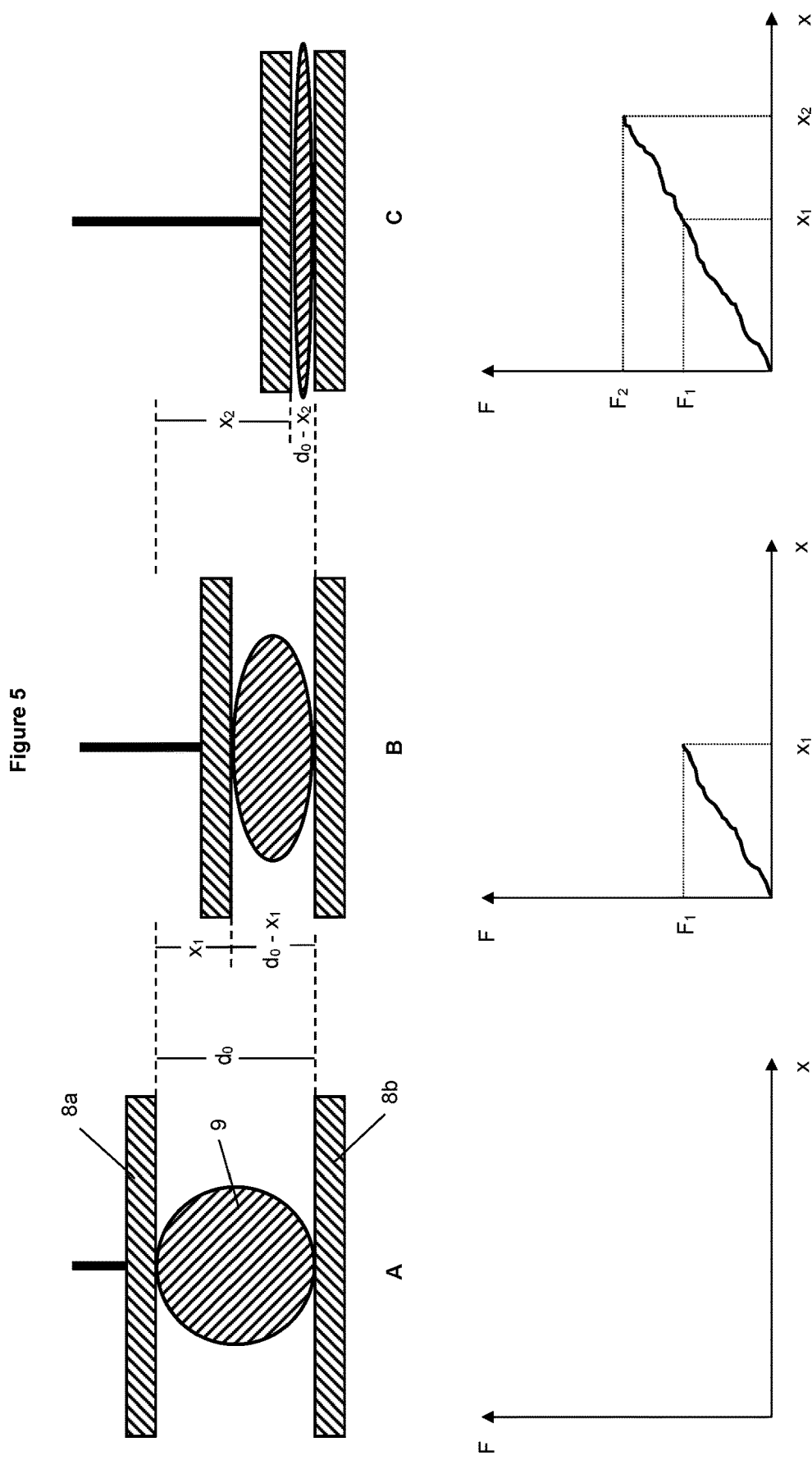
FIG. 5 illustrates the behavior of the particulates contained in the tablets according to the invention when being subjected to a breaking strength test, in particular their deformability.

FIG. 5 schematically illustrates the measurement and the corresponding force-displacement-diagram. In particular, FIG. 5A shows the initial situation at the beginning of the measurement. The sample particulate (9) is placed between upper jaw (8a) and lower jaw (8b) which each are in intimate contact with the surface of the particulate (9). The initial displacement $d_0$ between upper jaw (8a) and lower jaw (8b) corresponds to the extension of the particulate orthogonal to the surfaces of upper jaw (8a) and lower jaw (8b). At this time, no force is exerted at all and thus, no graph is displayed in the force-displacement-diagram below. When the measurement is commenced, the upper jaw is moved in direction of lower jaw (8b), preferably at a constant speed. FIG. 5B shows a situation where due to the movement of upper jaw (8a) towards lower jaw (8b) a force is exerted on particulate (9). Because of its deformability, the particulate (9) is flattened without being fractured. The force-displacement-diagram indicates that after a reduction of the displacement $d_0$ of upper jaw (8a) and lower jaw (8b) by distance $x_1$, i.e. at a displacement of $d_1=d_0-x_1$, a force $F_1$ is measured. FIG. 5C shows a situation where due to the continuous movement of upper jaw (8a) towards lower jaw (8b), the force that is exerted on particulate (9) causes further deformation, although the particulate (9) does not fracture. The force-displacement-diagram indicates that after a reduction of the displacement $d_0$ of upper jaw (8a) and lower jaw (8b) by distance $x_2$, i.e. at a displacement of $d_2=d_0-x_2$, a force $F_2$ is measured. Under these circumstances, the particulate (9) has not been broken (fractured) and a substantially steady increase of the force in the force-displacement-diagram is measured.

Figure 6:
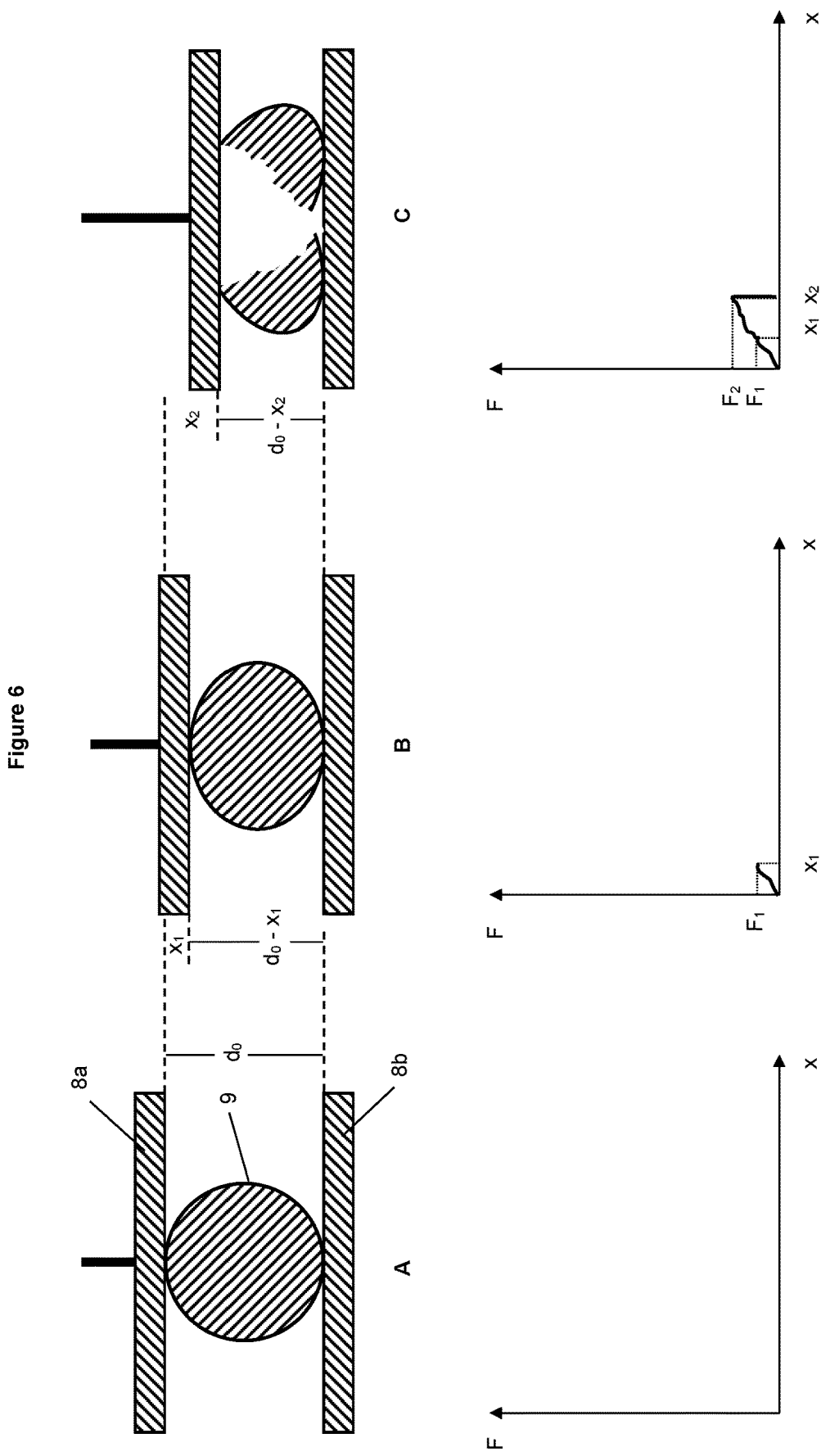
FIG. 6 illustrates the behavior of conventional particulates when being subjected to a breaking strength test.

In contrast, FIG. 6 schematically illustrates the measurement and the corresponding force-displacement-diagram of a conventional comparative particulate not having the degree of deformability as the particulates according to the invention. FIG. 6A shows the initial situation at the beginning of the measurement. The comparative sample particulate (9) is placed between upper jaw (8a) and lower jaw (8b) which each are in intimate contact with the surface of the comparative particulate (9). The initial displacement $d_0$ between upper jaw (8a) and lower jaw (8b) corresponds to the extension of the comparative particulate orthogonal to the surfaces of upper jaw (8a) and lower jaw (8b). At this time, no force is exerted at all and thus, no graph is displayed in the force-displacement-diagram below. When the measurement is commenced, the upper jaw is moved in direction of lower jaw (8b), preferably at a constant speed. FIG. 6B shows a situation where due to the movement of upper jaw (8a) towards lower jaw (8b) a force is exerted on comparative particulate (9). Because of some deformability, the comparative particulate (9) is slightly flattened without being fractured. The force-displacement-diagram indicates that after a reduction of the displacement $d_0$ of upper jaw (8a) and lower jaw (8b) by distance $x_1$, i.e. at a displacement of $d_1=d_0-x_1$, a force $F_1$ is measured. FIG. 6C shows a situation where due to the continuous movement of upper jaw (8a) towards lower jaw (8b), the force that is exerted on particulate (9) causes sudden fracture of the comparative particulate (9). The force-displacement-diagram indicates that after a reduction of the displacement $d_0$ of upper jaw (8a) and lower jaw (8b) by distance $x_2$, i.e. at a displacement of $d_2=d_0-x_2$, a force $F_2$ is measured that suddenly drops when the particulate fractures. Under these circumstances, the particulate (9) has been broken (fractured) and no steady increase of the force in the force-displacement-diagram is measured. The sudden drop (decrease) of the force can easily be recognized and does not need to be quantified for the measurement. The steady increase in the force-displacement-diagram ends at displacement $d_2=d_0-x_2$ when the particulate breaks.

In a preferred embodiment, the particulates contained in the tablet according to the invention have a deformability such that they show an increase, preferably a substantially steady increase of the force at a corresponding decrease of the displacement in the force-displacement-diagram when being subjected to a breaking strength test as described above ("Zwick Z 2.5" materials tester, constant speed), preferably at least until the displacement d of upper jaw (8a) and lower jaw (8b) has been reduced to a value of 90% of the original displacement $d_0$ (i.e. $d=0.9\cdot d_0$), preferably to a displacement d of 80% of the original displacement $d_0$, more preferably to a displacement d of 70% of the original displacement $d_0$, still more preferably to a displacement d of 60% of the original displacement $d_0$, yet more preferably to a displacement d of 50% of the original displacement $d_0$, even more preferably to a displacement d of 40% of the original displacement $d_0$, most preferably to a displacement d of 30% of the original displacement $d_0$, and in particular to a displacement d of 20% of the original displacement $d_0$, or to a displacement d of 15% of the original displacement $d_0$, to a displacement d of 10% of the original displacement $d_0$, or to a displacement d of 5% of the original displacement $d_0$.

In another preferred embodiment, the particulates contained in the tablet according to the invention have a deformability such that they show an increase, preferably a substantially steady increase of the force at a corresponding decrease of the displacement in the force-displacement-diagram when being subjected to a breaking strength test as described above ("Zwick Z 2.5" materials tester, constant speed), preferably at least until the displacement d of upper jaw (8a) and lower jaw (8b) has been reduced to 0.80 mm or 0.75 mm, preferably 0.70 mm or 0.65 mm, more preferably 0.60 mm or 0.55 mm, still more preferably 0.50 mm or 0.45 mm, yet more preferably 0.40 mm or 0.35 mm, even more preferably 0.30 mm or 0.25 mm, most preferably 0.20 mm or 0.15 mm and in particular 0.10 or 0.05 mm.

In still another preferred embodiment, the particulates contained in the tablet according to the invention have a deformability such that they show an increase, preferably a substantially steady increase of the force at a corresponding decrease of the displacement in the force-displacement-diagram when being subjected to a breaking strength test as described above ("Zwick Z 2.5" materials tester, constant speed), at least until the displacement d of upper jaw (8a) and lower jaw (8b) has been reduced to 50% of the original displacement $d_0$ (i.e. $d=d_0/2$), whereas the force measured at said displacement ($d=d_0/2$) is at least 25 N or at least 50 N, preferably at least 75 N or at least 100 N, still more preferably at least 150 N or at least 200 N, yet more preferably at least 250 N or at least 300 N, even more preferably at least 350 N or at least 400 N, most preferably at least 450 N or at least 500 N, and in particular at least 625 N, or at least 750 N, or at least 875 N, or at least 1000 N, or at least 1250 N, or at least 1500 N.

In another preferred embodiment, the particulates contained in the tablet according to the invention have a deformability such that they show an increase, preferably a substantially steady increase of the force at a corresponding decrease of the displacement in the force-displacement-diagram when being subjected to a breaking strength test as described above ("Zwick Z 2.5" materials tester, constant speed), at least until the displacement d of upper jaw (8a) and lower jaw (8b) has been reduced by at least 0.1 mm, more preferably at least 0.2 mm, still more preferably at least 0.3 mm, yet more preferably at least 0.4 mm, even more preferably at least 0.5 mm, most preferably at least 0.6 mm, and in particular at least 0.7 mm, whereas the force measured at said displacement is within the range of from 5.0 N to 250 N, more preferably from 7.5 N to 225 N, still more preferably from 10 N to 200 N, yet more preferably from 15 N to 175 N, even more preferably from 20 N to 150 N, most preferably from 25 N to 125 N, and in particular from 30 N to 100 N.

In yet another embodiment, the particulates contained in the tablet according to the invention have a deformability such that they are deformed without being fractured when subjected to a constant force of e.g. 50 N, 100 N, 200 N, 300 N, 400 N, 500 N or 600 N in a breaking strength test as described above ("Zwick Z 2.5" materials tester, constant force), until the displacement d of upper jaw (8a) and lower jaw (8b) is reduced so that no further deformation takes place at said constant force, whereas at this equilibrated state the displacement d of upper jaw (8a) and lower jaw (8b) is at most 90% of the original displacement $d_0$ (i.e. $d\leq0.9\cdot d_0$), preferably at most 80% of the original displacement $d_0$ (i.e. $d\leq0.8\cdot d_0$), more preferably at most 70% of the original displacement $d_0$ (i.e. $d\leq0.7\cdot d_0$), still more preferably at most 60% of the original displacement $d_0$ (i.e. $d\leq0.6\cdot d_0$), yet more preferably at most 50% of the original displacement $d_0$ (i.e.

d≤0.5·$d_0$), even more preferably at most 40% of the original displacement $d_0$ (i.e. d≤0.4·$d_0$), most preferably at most 30% of the original displacement $d_0$ (i.e. d≤0.3·$d_0$), and in particular at most 20% of the original displacement $d_0$ (i.e. d≤0.2·$d_0$), or at most 15% of the original displacement $d_0$ (i.e. d≤0.15·$d_0$), at most 10% of the original displacement $d_0$ (i.e. d≤0.1·$d_0$), or at most 5% of the original displacement $d_0$ (i.e. d≤0.05·$d_0$).

Preferably, the particulates contained in the tablet according to the invention have a deformability such that they are deformed without being fractured when subjected to a constant force of e.g. 50 N, 100 N, 200 N, 300 N, 400 N, 500 N or 600 N in a breaking strength test as described above ("Zwick Z 2.5" materials tester, constant force), until the displacement d of upper jaw (8a) and lower jaw (8b) is reduced so that no further deformation takes place at said constant force, whereas at this equilibrated state the displacement d of upper jaw (8a) and lower jaw (8b) is at most 0.80 mm or at most 0.75 mm, preferably at most 0.70 mm or at most 0.65 mm, more preferably at most 0.60 mm or at most 0.55 mm, still more preferably at most 0.50 mm or at most 0.45 mm, yet more preferably at most 0.40 mm or at most 0.35 mm, even more preferably at most 0.30 mm or at most 0.25 mm, most preferably at most 0.20 mm or at most 0.15 mm and in particular at most 0.10 or at most 0.05 mm.

In another embodiment, the particulates contained in the tablet according to the invention have a deformability such that they are deformed without being fractured when subjected to a constant force of e.g. 50 N, 100 N, 200 N, 300 N, 400 N, 500 N or 600 N in a breaking strength test as described above ("Zwick Z 2.5" materials tester, constant force), until the displacement d of upper jaw (8a) and lower jaw (8b) is reduced so that no further deformation takes place at said constant force, whereas at this equilibrated state the displacement d of upper jaw (8a) and lower jaw (8b) is at least 5% of the original displacement $d_0$ (i.e. d≥0.05·$d_0$), preferably at least 10% of the original displacement $d_0$ (i.e. d≥0.1·$d_0$), more preferably at least 15% of the original displacement $d_0$ (i.e. d≥0.15·$d_0$), still more preferably at least 20% of the original displacement $d_0$ (i.e. d≥0.2·$d_0$), yet more preferably at least 30% of the original displacement $d_0$ (i.e. d≥0.3·$d_0$), even more preferably at least 40% of the original displacement $d_0$ (i.e. d≥0.4·$d_0$), most preferably at least 50% of the original displacement $d_0$ (i.e. d≥0.5·$d_0$), and in particular at least 60% of the original displacement $d_0$ (i.e. d≥0.6·$d_0$), or at least 70% of the original displacement $d_0$ (i.e. d≥0.7·$d_0$), at least 80% of the original displacement $d_0$ (i.e. d≥0.8·$d_0$), or at least 90% of the original displacement $d_0$ (i.e. d≥0.9·$d_0$).

Preferably, the particulates contained in the tablet according to the invention have a deformability such that they are deformed without being fractured when subjected to a constant force of e.g. 50 N, 100 N, 200 N, 300 N, 400 N, 500 N or 600 N in a breaking strength test as described above ("Zwick Z 2.5" materials tester, constant force), until the displacement d of upper jaw (8a) and lower jaw (8b) is reduced so that no further deformation takes place at said constant force, whereas at this equilibrated state the displacement d of upper jaw (8a) and lower jaw (8b) is at least 0.05 mm or at least 0.10 mm, preferably at least 0.15 mm or at least 0.20 mm, more preferably at least 0.25 mm or at least 0.30 mm, still more preferably at least 0.35 mm or at least 0.40 mm, yet more preferably at least 0.45 mm or at least 0.50 mm, even more preferably at least 0.55 mm or at least 0.60 mm, most preferably at least 0.65 mm or at least 0.70 mm and in particular at least 0.75 or at least 0.80 mm.

Preferably, the tablet according to the invention provides under in vitro conditions immediate release of the pharmacologically active compound in accordance with Ph. Eur.

The term "immediate release" as applied to tablets is understood by persons skilled in the art which has structural implications for the respective tablets. The term is defined, for example, in the current issue of the US Pharmacopoeia (USP), General Chapter 1092, "THE DISSOLUTION PROCEDURE: DEVELOPMENT AND VALIDATION", heading "STUDY DESIGN", "Time Points". For immediate-release dosage forms, the duration of the procedure is typically 30 to 60 minutes; in most cases, a single time point specification is adequate for Pharmacopeia purposes. Industrial and regulatory concepts of product comparability and performance may require additional time points, which may also be required for product registration or approval. A sufficient number of time points should be selected to adequately characterize the ascending and plateau phases of the dissolution curve. According to the Biopharmaceutics Classification System referred to in several FDA Guidances, highly soluble, highly permeable drugs formulated with rapidly dissolving products need not be subjected to a profile comparison if they can be shown to release 85% or more of the active drug substance within 15 minutes. For these types of products a one-point test will suffice. However, most products do not fall into this category. Dissolution profiles of immediate-release products typically show a gradual increase reaching 85% to 100% at about 30 to 45 minutes. Thus, dissolution time points in the range of 15, 20, 30, 45, and 60 minutes are usual for most immediate-release products.

Preferably, under physiological conditions the tablet according to the invention has released after 30 minutes at least 70%, more preferably at least 75%, still more preferably at least 80%, yet more preferably at least 82%, most preferably at least 84% and in particular at east 86% of the pharmacologically active compound originally contained in the tablet.

Preferably, under physiological conditions the tablet according to the invention has released after 10 minutes at least 70%, more preferably at least 73%, still more preferably at least 76%, yet more preferably at least 78%, most preferably at least 80% and in particular at east 82% of the pharmacologically active compound originally contained in the tablet.

Further preferred release profiles $C^1$ to $C^{10}$ are summarized in the table here below [all data in wt.-% of released pharmacologically active compound]:

| time | $C^1$ | $C^2$ | $C^3$ | $C^4$ | $C^5$ | $C^6$ | $C^7$ | $C^8$ | $C^9$ | $C^{10}$ |
|---|---|---|---|---|---|---|---|---|---|---|
| 10 min | ≥30 | ≥35 | ≥40 | ≥45 | ≥50 | ≥60 | ≥70 | ≥80 | ≥80 | ≥80 |
| 20 min | ≥50 | ≥55 | ≥60 | ≥65 | ≥70 | ≥75 | ≥80 | ≥85 | ≥90 | ≥95 |
| 30 min | ≥55 | ≥60 | ≥65 | ≥70 | ≥75 | ≥85 | ≥90 | ≥95 | ≥95 | ≥95 |
| 40 min | ≥60 | ≥65 | ≥70 | ≥80 | ≥85 | ≥90 | ≥95 | ≥95 | ≥95 | ≥95 |
| 50 min | ≥65 | ≥70 | ≥80 | ≥85 | ≥88 | ≥92 | ≥95 | ≥95 | ≥95 | ≥95 |
| 60 min | ≥75 | ≥80 | ≥85 | ≥90 | ≥92 | ≥94 | ≥95 | ≥95 | ≥95 | ≥95 |

Preferably, the release profile, the drug and the pharmaceutical excipients of the tablet according to the invention are stable upon storage, preferably upon storage at elevated temperature, e.g. 40° C., for 3 months in sealed containers.

In connection with the release profile "stable" means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

In connection with the drug and the pharmaceutical excipients "stable" means that the tablets satisfy the requirements of EMEA concerning shelf-life of pharmaceutical products.

Suitable in vitro conditions are known to the skilled artisan. In this regard it can be referred to, e.g., the Eur. Ph. Preferably, the release profile is measured under the following conditions: Paddle apparatus equipped without sinker, 50 rpm, 37±5° C., 900 mL simulated intestinal fluid pH 6.8 (phosphate buffer) or pH 4.5. In a preferred embodiment, the rotational speed of the paddle is increased to 75 rpm.

In a preferred embodiment, the tablet according to the invention is adapted for administration once daily. In another preferred embodiment, the tablet according to the invention is adapted for administration twice daily. In still another preferred embodiment, the tablet according to the invention is adapted for administration thrice daily. In yet another preferred embodiment, the tablet according to the invention is adapted for administration more frequently than thrice daily, for example 4 times daily, 5 times daily, 6 times daily, 7 times daily or 8 times daily.

For the purpose of specification, "twice daily" means equal or nearly equal time intervals, i.e., about every 12 hours, or different time intervals, e.g., 8 and 16 hours or 10 and 14 hours, between the individual administrations.

For the purpose of specification, "thrice daily" means equal or nearly equal time intervals, i.e., about every 8 hours, or different time intervals, e.g., 6, 6 and 12 hours; or 7, 7 and 10 hours, between the individual administrations.

Preferably, the tablet according to the invention has under in vitro conditions a disintegration time measured in accordance with Ph. Eur. of at most 5 minutes, more preferably at most 4 minutes, still more preferably at most 3 minutes, yet more preferably at most 2.5 minutes, most preferably at most 2 minutes and in particular at most 1.5 minutes.

It has been surprisingly found that oral dosage forms can be designed that provide the best compromise between tamper-resistance, disintegration time and drug release, drug load, processability (especially tablettability) and patient compliance.

It has been found that the disintegration time of the tablets according to the invention can be influenced by the relative weight ratio of matrix material:particulates. In general, it was observed that the higher this ratio the faster disintegration. However, this ratio cannot be increased ad ultimo, as further tablet properties need to be taken into account, particularly drug load and total tablet size and weight. As a certain dosage of pharmacologically active compound needs to be administered, the content of particulates should still be sufficiently high and the total tablet weight should not exceed a certain limit, as this would deteriorate patient compliance, e.g. swallowability.

The situation is more complicated by trends in opposite direction. In particular, it has been found that the tablettability of the tablets according to the invention can also be influenced by the relative weight ratio of matrix material:particulates. In general, it was observed that the lower this ratio the better the tablettability. This trend parallels the trend of the drug load.

Thus, disintegration time on the one hand and tablettability/drug load on the other hand can be optimized by finding the best compromise.

Similarly, tamper-resistance and drug release also antagonize each other. While smaller particulates should typically show a faster release of the pharmacologically active compound, tamper-resistance requires some minimal size of the coated particulates in order to effectively prevent abuse, e.g. i.v. administration. The larger the coated particulates are the less they are suitable for being abused nasally. The smaller the coated particulates are the faster gel formation occurs.

Thus, drug release on the one hand and tamper-resistance on the other hand can be optimized by finding the best compromise.

Preferred embodiments $D^1$ to $D^4$ of the tablets according to the invention are summarized in the table here below:

| [wt.-%, relative to weight of tablet] | $D^1$ | $D^2$ | $D^3$ | $D^4$ |
|---|---|---|---|---|
| tablet | | | | |
| total weight [mg] | 500 ± 300 | 500 ± 250 | 500 ± 200 | 500 ± 150 |
| coated particulates | | | | |
| total content [wt.-%] | 50 ± 15 | 50 ± 12.5 | 50 ± 10 | 50 ± 7.5 |
| average particle size [μm] | 800 ± 400 | 800 ± 300 | 800 ± 200 | 800 ± 100 |
| content of ph. active compound | 23 ± 20 | 23 ± 15 | 23 ± 10 | 23 ± 5 |
| content of polymer [wt.-%] | 22 ± 12 | 22 ± 10 | 22 ± 8 | 22 ± 6 |
| content of plasticizer [wt.-%] | 4 ± 3.5 | 4 ± 3 | 4 ± 2.5 | 4 ± 2 |
| content of further excipients [wt.-%] | 0.05 ± 0.05 | 0.05 ± 0.04 | 0.05 ± 0.03 | 0.05 ± 0.02 |
| content of coating material [wt.-%] | 2.0 ± 1.8 | 2.0 ± 1.6 | 2.0 ± 1.4 | 2.0 ± 1.2 |
| matrix material | | | | |
| total content [wt.-%] | 49 ± 15 | 49 ± 12 | 49 ± 9 | 49 ± 6 |
| content of filler(s)/binder(s) [wt.-%] | 43 ± 10 | 43 ± 8 | 43 ± 6 | 43 ± 4 |
| content of disintegrant [wt.-%] | 5 ± 4 | 5 ± 3.5 | 5 ± 3 | 5 ± 2.5 |
| content of lubricant [wt.-%] | 0.15 ± 0.15 | 0.15 ± 0.14 | 0.15 ± 0.13 | 0.15 ± 0.12 |

The coated particulates according to the invention are preferably prepared by melt-extrusion, although also other methods of thermoforming may be used in order to manufacture the coated particulates according to the invention such as press-molding at elevated temperature or heating of particulates that were manufactured by conventional compression in a first step and then heated above the softening temperature of the physiologically acceptable polymer, preferably the polyalkylene oxide in the coated particulates in a second step to form hard tablets. In this regards, thermoforming means the forming, or molding of a mass after the application of heat. In a preferred embodiment, the coated particulates are thermoformed by hot-melt extrusion.

In a preferred embodiment, the coated particulates are prepared by hot melt-extrusion, preferably by means of a twin-screw-extruder. Melt extrusion preferably provides a melt-extruded strand that is preferably cut into monoliths, which are then optionally compressed and formed into particulates. Preferably, compression is achieved by means of a die and a punch, preferably from a monolithic mass obtained by melt extrusion. If obtained via melt extrusion, the compressing step is preferably carried out with a monolithic mass exhibiting ambient temperature, that is, a temperature in the range from 20 to 25° C. The strands obtained by way of extrusion can either be subjected to the compression step as such or can be cut prior to the compression step. This cutting can be performed by usual techniques, for example using rotating knives or compressed air, at elevated temperature, e.g. when the extruded stand is still warm due to hot-melt extrusion, or at ambient temperature, i.e. after the extruded strand has been allowed to cool down. When the extruded strand is still warm, singulation of the extruded strand into extruded particulates is preferably performed by cutting the extruded strand immediately after it has exited the extrusion die. However, when the extruded strand is cut in the cooled state, subsequent singulation of the extruded strand into extruded particulates is preferably performed by optionally transporting the still hot extruded strand by means of conveyor belts, allowing it to cool down and to congeal, and subsequently cutting it into extruded particulates. Alternatively, the shaping can take place as described in EP-A 240 906 by the extrudate being passed between two counter-rotating calender rolls and being shaped directly to particulates. It is of course also possible to subject the extruded strands to the compression step or to the cutting step when still warm, that is more or less immediately after the extrusion step. The extrusion is preferably carried out by means of a twin-screw extruder.

The coated particulates according to the invention may be produced by different processes, the particularly preferred of which are explained in greater detail below. Several suitable processes have already been described in the prior art. In this regard it can be referred to, e.g., WO 2005/016313, WO 2005/016314, WO 2005/063214, WO 2005/102286, WO 2006/002883, WO 2006/002884, WO 2006/002886, WO 2006/082097, and WO 2006/082099.

In general, the process for the production of the coated particulates according to the invention preferably comprises the following steps:
(a) mixing all ingredients;
(b) optionally pre-forming the mixture obtained from step (a), preferably by applying heat and/or force to the mixture obtained from step (a), the quantity of heat supplied preferably not being sufficient to heat the physiologically acceptable polymer, preferably the polyalkylene oxide up to its softening point;
(c) hardening the mixture by applying heat and force, it being possible to supply the heat during and/or before the application of force and the quantity of heat supplied being sufficient to heat the physiologically acceptable polymer, preferably the polyalkylene oxide at least up to its softening point; and thereafter allowing the material to cool and removing the force (d) optionally singulating the hardened mixture;
(e) optionally shaping the particulates; and
(f) providing a coating, preferably a film coating.

Heat may be supplied directly, e.g. by contact or by means of hot gas such as hot air, or with the assistance of ultrasound; or is indirectly supplied by friction and/or shear. Force may be applied and/or the particulates may be shaped for example by direct tabletting or with the assistance of a suitable extruder, particularly by means of a screw extruder equipped with one or two screws (single-screw-extruder and twin-screw-extruder, respectively) or by means of a planetary gear extruder.

The final shape of the particulates may either be provided during the hardening of the mixture by applying heat and force (step (c)) or in a subsequent step (step (e)). In both cases, the mixture of all components is preferably in the plastified state, i.e. preferably, shaping is performed at a temperature at least above the softening point of the physiologically acceptable polymer, preferably the polyalkylene oxide. However, extrusion at lower temperatures, e.g. ambient temperature, is also possible and may be preferred.

Shaping can be performed, e.g., by means of a tabletting press comprising die and punches of appropriate shape.

Suitable methods for providing particulates with a coating, preferably with a film coating, are known to the skilled person such as fluidized bed coating, pan-coating, coazervation, dry powder coating, extrusion coating, and phoqus technology (copy-coating). Preferably, the particulates are coated by spraying (top-spray or bottom-spray) e.g. in a fluidized bed spray dry granulator.

A particularly preferred process for the manufacture of the coated particulates according to the invention involves hot-melt extrusion. In this process, the coated particulates according to the invention are produced by thermoforming with the assistance of an extruder, preferably without there being any observable consequent discoloration of the extrudate.

This process is characterized in that
a) all components are mixed,
b) the resultant mixture is heated in the extruder at least up to the softening point of the physiologically acceptable polymer, preferably the polyalkylene oxide and extruded through the outlet orifice of the extruder by application of force,
c) the still plastic extrudate is singulated and formed into the particulates or
d) the cooled and optionally reheated singulated extrudate is formed into the particulates.

Mixing of the components according to process step a) may also proceed in the extruder.

The components may also be mixed in a mixer known to the person skilled in the art. The mixer may, for example, be a roll mixer, shaking mixer, shear mixer or compulsory mixer.

The, preferably molten, mixture which has been heated in the extruder at least up to the softening point of physiologically acceptable polymer, preferably polyalkylene oxide is extruded from the extruder through a die with at least one bore.

The process according to the invention requires the use of suitable extruders, preferably screw extruders. Screw extruders which are equipped with two screws (twin-screw-extruders) are particularly preferred.

Preferably, extrusion is performed in the absence of water, i.e., no water is added. However, traces of water (e.g., caused by atmospheric humidity) may be present.

The extruder preferably comprises at least two temperature zones, with heating of the mixture at least up to the softening point of the physiologically acceptable polymer, preferably the polyalkylene oxide proceeding in the first zone, which is downstream from a feed zone and optionally mixing zone. The throughput of the mixture is preferably from 1.0 kg to 15 kg/hour. In a preferred embodiment, the throughput is from 0.5 kg/hour to 3.5 kg/hour. In another preferred embodiment, the throughput is from 4 to 15 kg/hour.

In a preferred embodiment, the die head pressure is within the range of from 25 to 200 bar. The die head pressure can be adjusted inter alia by die geometry, temperature profile, extrusion speed, number of bores in the dies, screw configuration, first feeding steps in the extruder, and the like.

The die geometry or the geometry of the bores is freely selectable. The die or the bores may accordingly exhibit a round, oblong or oval cross-section, wherein the round cross-section preferably has a diameter of 0.1 mm to 2 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of the physiologically acceptable polymer, preferably the polyalkylene oxide and does not rise above a temperature at which the pharmacologically active compound to be processed may be damaged. Preferably, the temperature of the mixture to be extruded is adjusted to below 180° C., preferably below 150° C., but at least to the softening temperature of the physiologically acceptable polymer, preferably the polyalkylene oxide. Typical extrusion temperatures are 120° C. and 150° C.

In a preferred embodiment, the extruder torque is within the range of from 30 to 95%. Extruder torque can be adjusted inter alia by die geometry, temperature profile, extrusion speed, number of bores in the dies, screw configuration, first feeding steps in the extruder, and the like.

After extrusion of the molten mixture and optional cooling of the extruded strand or extruded strands, the extrudates are preferably singulated. This singulation may preferably be performed by cutting up the extrudates by means of revolving or rotating knives, wires, blades or with the assistance of laser cutters.

Preferably, intermediate or final storage of the optionally singulated extrudate or the final shape of the particulates according to the invention is performed under oxygen-free atmosphere which may be achieved, e.g., by means of oxygen-scavengers.

The singulated extrudate may be press-formed into particulates in order to impart the final shape to the particulates.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a tablet with desired mechanical properties, may be established by simple preliminary testing.

For example but not limiting, extrusion may be performed by means of a twin-screw-extruder type ZSE 18 or ZSE27 (Leistritz, Nurnberg, Germany), screw diameters of 18 or 27 mm. Screws having eccentric or blunt ends may be used. A heatable die with a round bore or with a multitude of bores each having a diameter of 0.2, 0.3, 0.4, 0.5, 0.6, 0.7, 0.8, 0.9 or 1.0 mm may be used. The extrusion parameters may be adjusted e.g. to the following values: rotational speed of the screws: 120 Upm; delivery rate 2 kg/h for a ZSE 18 or 3 kg/h, 8 kg/h, or even 10 kg/h and more for a ZSE27; product temperature: in front of die 125° C. and behind die 135° C.; and jacket temperature: 110° C. The throughput can generally be increased by increasing the number of dies at the extruder outlet.

Preferably, extrusion is performed by means of twin-screw-extruders or planetary-gear-extruders, twin-screw extruders (co-rotating or contra-rotating) being particularly preferred.

The particulates according to the invention are preferably produced by thermoforming with the assistance of an extruder without any observable consequent discoloration of the extrudates.

The process for the preparation of the coated particulates according to the invention is preferably performed continuously. Preferably, the process involves the extrusion of a homogeneous mixture of all components. It is particularly advantageous if the thus obtained intermediate, e.g. the strand obtained by extrusion, exhibits uniform properties. Particularly desirable are uniform density, uniform distribution of the active compound, uniform mechanical properties, uniform porosity, uniform appearance of the surface, etc. Only under these circumstances the uniformity of the pharmacological properties, such as the stability of the release profile, may be ensured and the amount of rejects can be kept low.

Preferably, the coated particulates according to the invention can be regarded as "extruded pellets". The term "extruded pellets" has structural implications which are understood by persons skilled in the art. A person skilled in the art knows that pelletized dosage forms can be prepared by a number of techniques, including:

drug layering on nonpareil sugar or microcrystalline cellulose beads,
spray drying,
spray congealing,
rotogranulation,
hot-melt extrusion,
spheronization of low melting materials, or
extrusion-spheronization of a wet mass.

Accordingly, "extruded pellets" can be obtained either by hot-melt extrusion or by extrusion-spheronization.

"Extruded pellets" can be distinguished from other types of pellets, as extruded pellets typically have a different shape. The shape of the extruded pellets is typically more cut-rod-like than perfectly globated round.

"Extruded pellets" can be distinguished from other types of pellets because they are structurally different. For example, drug layering on nonpareils yields multilayered pellets having a core, whereas extrusion typically yields a monolithic mass comprising a homogeneous mixture of all ingredients. Similarly, spray drying and spray congealing typically yield spheres, whereas extrusion typically yields cylindrical extrudates which can be subsequently spheronized.

The structural differences between "extruded pellets" and "agglomerated pellets" are significant because they may affect the release of active substances from the pellets and consequently result in different pharmacological profiles. Therefore, a person skilled in the pharmaceutical formulation art would not consider "extruded pellets" to be equivalent to "agglomerated pellets".

The tablets according to the invention may be prepared by any conventional method. Preferably, however, the tablets are prepared by compression. Thus, coated particulates as hereinbefore defined are preferably mixed, e.g. blended and/or granulated (e.g. wet granulated), with matrix material and the resulting mix (e.g. blend or granulate) is then compressed, preferably in moulds, to form tablets. It is also envisaged that the coated particulates herein described may be incorporated into a matrix using other processes, such as by melt granulation (e.g. using fatty alcohols and/or water-soluble waxes and/or water-insoluble waxes) or high shear granulation, followed by compression.

When the tablets according to the invention are manufactured by means of an eccentric press, the compression force is preferably within the range of from 5 to 15 kN. When the tablets according to the invention are manufactured by means of a rotating press, the compression force is preferably within the range of from 5 to 40 kN, in certain embodiments >25 kN, in other embodiments about 13 kN.

The tablets according to the invention may optionally comprise a coating, e.g. a cosmetic coating. The coating is preferably applied after formation of the tablet. The coating may be applied prior to or after the curing process. Preferred coatings are Opadry® coatings available from Colorcon. Other preferred coating are Opaglos® coatings, also commercially available from Colorcon.

The tablet according to the invention is characterized by excellent storage stability. Preferably, after storage for 4 weeks at 40° C. and 75% rel. humidity, the content of pharmacologically active compound amounts to at least 98.0%, more preferably at least 98.5%, still more preferably at least 99.0%, yet more preferably at least 99.2%, most preferably at least 99.4% and in particular at least 99.6%, of its original content before storage. Suitable methods for measuring the content of the pharmacologically active compound in the tablet are known to the skilled artisan. In this regard it is referred to the Eur. Ph. or the USP, especially to reversed phase HPLC analysis. Preferably, the tablet is stored in closed, preferably sealed containers.

Further aspects according to the invention—basis for additional claim categories The coated particulates and tablets according to the invention may be used in medicine, e.g. as an analgesic. The coated particulates and tablets are therefore particularly suitable for the treatment or management of pain. In such tablets, the pharmacologically active compound is preferably an analgesic.

A further aspect according to the invention relates to the tablet as described above for use in the treatment of pain.

A further aspect according to the invention relates to the use of a tablet as described above for avoiding or hindering the abuse of the pharmacologically active compound contained therein.

A further aspect according to the invention relates to the use of a tablet as described above for avoiding or hindering the unintentional overdose of the pharmacologically active compound contained therein.

In this regard, the invention also relates to the use of a pharmacologically active compound as described above and/or a physiologically acceptable polymer, preferably a polyalkylene oxide as described above for the manufacture of the tablet according to the invention for the prophylaxis and/or the treatment of a disorder, thereby preventing an overdose of the pharmacologically active compound, particularly due to comminution of the tablet by mechanical action.

EXAMPLES

The following examples further illustrate the invention but are not to be construed as limiting its scope.

Example 1

The relevance of the particulate size on tamper resistance was investigated.

It was found that comparatively small particulates, e.g. particulates having a diameter and length of 0.5 mm×0.5 mm already provide a certain degree of tamper resistance: when administered nasally they cause an unpleasant feeling and furthermore, due to the lack of water on the mucous membrane, do not release the pharmacologically active compound as quick as when being administered orally. Therefore, a kick or rush can unlikely be achieved by nasal administration of such particulates. Thus, even when being administered nasally, such comparatively small particulates already provide tamper resistance, i.e. avoid drug abuse or at least make drug abuse substantially more difficult. Furthermore, such comparatively small particulates have excellent swelling properties thereby effectively preventing conversion into a liquid formulation for intravenous administration.

It was found that tamper-resistance can even further be improved by increasing the particulate size, e.g. to a diameter and length of 1.0 mm×1.0 mm. Such particulates even provide a more unpleasant feeling when being administered nasally and in the absence of sufficient water, rather slowly release the pharmacologically active compound. Further, they cannot be easily converted into a liquid formulation for intravenous administration either.

As such a more pronounced retardant effect, however, is detrimental for the desired immediate release upon prescribed oral administration of the tablets, a compromise must be found between tamper resistance on the one hand and immediate drug release upon prescribed oral administration on the other hand, particularly with respect to disintegration time and drug release kinetics. Furthermore, drug load, processability (especially tablettability) and patient compliance are also important requirements to be satisfied with.

A predetermined particulate size of 800 µm×800 µm was considered most appropriate, i.e. it was considered most appropriate to adjust the diameter of the extrusion die as well as cutting length of the extruded stand to 800 µm taking into consideration that die swelling may occur during the extrusion process, particularly when the strand exits the die, so that the diameter of the extruded strand in fact is expanded, depending upon the composition and the extrusion parameters to a diameter of about 1000 µm. Thus, when proceedings this way, it was considered most appropriate to manufacture extruded particulates having a diameter of about 1000 µm (after die swelling, diameter of extrusion die 800 µm) and a length of about 800 µm.

Example 2

Different particulate compositions were investigated and particulates of different sizes were manufactured therefrom.

The particulate compositions are summarized in the table here below:

| [wt.-%] | 1 | 2 | 3 | 4 | 5 | 6 | 7 | 8 | 9 |
|---|---|---|---|---|---|---|---|---|---|
| Tramadol HCl | 46.59 | 46.59 | 46.59 | 38.83 | — | — | — | — | 45.59 |
| Tapentadol HCl | — | — | — | — | 46.59 | 46.59 | 46.59 | 33.28 | — |
| PEG 6000 | 5.31 | 6.32 | 4.31 | 8.33 | 8.31 | 8.31 | 8.32 | 10.00 | 8.40 |
| HPMC 100 000 | 5.00 | 6.00 | 4.00 | 9.33 | — | — | 8.00 | 12.57 | 8.00 |
| PEO 7 Mio | 33.00 | 35.99 | 45.00 | 43.49 | 45.00 | 45.00 | 36.99 | 44.14 | 36.99 |
| α-tocopherol | 0.10 | 0.10 | 0.10 | 0.01 | 0.10 | 0.10 | 0.1 | 0.01 | 0.01 |
| Lutrol 127 | 10.00 | — | — | — | — | — | — | — | — |
| PVP CL | — | 5.00 | — | — | — | — | — | — | — |
| total weight [mg] | 250 mg | 250 mg | 250 mg | 300 mg | 250 mg | 250 mg | 250 mg | 350 mg | 250 mg |
| film coating AMB varnish | — | — | — | — | — | 3.88 | — | — | — |

All materials were weighed, sieved (manual sieve, 1 mm), blended (Bohle LM40 with MC5 or MC10, depending on size of bath) for 15 minutes at 14 rpm, and hot-melt extruded (Leistritz extruder Type ZSE18 with different configuration of screws).

The compositions 1 to 9 were extruded under the following extrusion conditions:

| | 1, 4, 7, 9 | 2 | 3 | 5 and 6 | 8 |
|---|---|---|---|---|---|
| Heating zone 1 | 20° C. | 20° C. | 20° C. | 20 | 25 |
| Heating zone 2 | 100° C. | 100° C. | 100° C. | 100 | 100 |
| Heating zone 3 | 100° C. | 100° C. | 100° C. | 100 | 100 |
| Heating zone 4 | 120° C. | 140° C. | 120° C. | 120 | 100 |
| Heating zone 5 | 120° C. | 120° C. | 120° C. | 120 | 100 |
| Heating zone 6 | 120° C. | 120° C. | 120° C. | 120 | 100 |
| Heating zone 7 | 120° C. | 140° C. | 120° C. | 120 | 100 |
| Heating zone 8 | 120° C. | 140° C. | 120° C. | 120 | 100 |
| Heating zone 10 | 120° C. | 140° C. | 120° C. | 120 | 120 |
| Heating zone 11 | 130° C. | 150° C. | 130° C. | 130 | 120 |
| Screw speed [rpm] | 100 | 100 | 100 | 100 | 100 |
| Throughput [g/min] | 10.00-16.66 | 16.66-28.04 | 16.66 | 16.66 | 16.66 |
| Screw configuration | low shear | low shear | low shear | extreme shear | low shear |

For larger scales, screw configuration can be adopted and temperatures can be raised (e.g., HZ8 and 10: 130° C., HZ11: 145° C.; or HZ11: 150° C. and extreme shear configuration, throughput 25 g/min).

Figure 3:
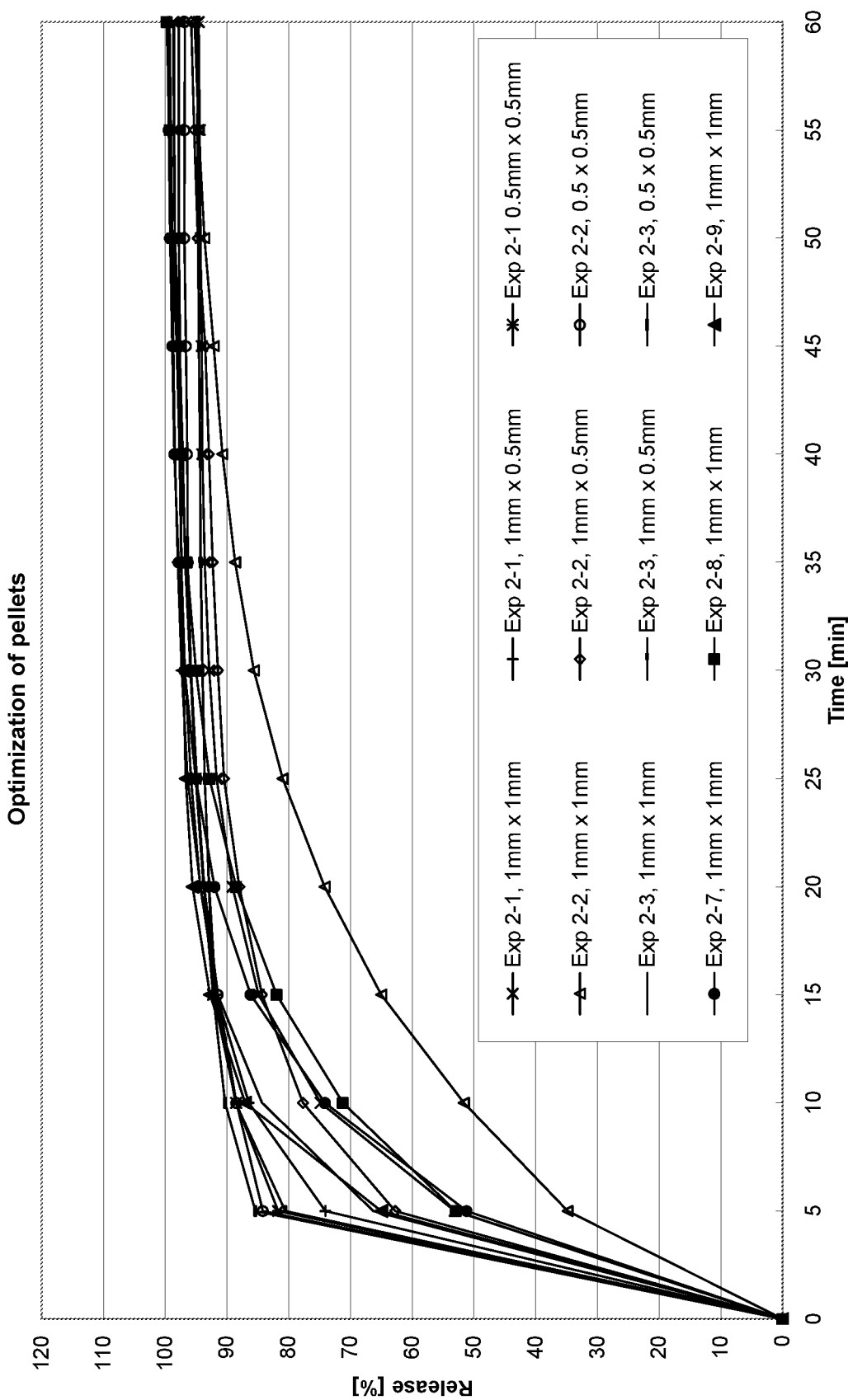
FIG. 3 shows in vitro release profiles of different tablets according to the invention having different compositions and particulate sizes.

The in vitro release characteristics were monitored in 900 mL 0.1N HCl at 37° C., using a paddle apparatus 50 rpm. The results are depicted in FIG. 3.

Example 3

The influence of the content of particulates in the tablet was investigated.

The following compositions were tested:
300 mg particulates in tablets having a total weight of 600 mg
250 mg particulates in tablets having a total weight of 600 mg
200 mg particulates in tablets having a total weight of 600 mg The most promising compromise between tablettability and size revealed to be 250 mg particulates in tablets having a total weight of 500 mg. Tablets having a total weight of 600 mg were considered too large with respect to patient compliance, although the relative weight ratio of particulates to matrix material of about 1:1 appeared advantageous with respect to disintegration time and dissolution time.

Example 4-1

The influence of the matrix material was investigated—wet granulation.

Granules having the following composition were prepared for manufacturing of pellet-tablets. Granules for outer the phase, i.e. the matrix material, were manufactured by wet granulation. Granules and pellets were blended. Segregation (optically) and disintegration of tablets after compression were evaluated. Tablets were manufactured "manually" (components were separately weighed for each tablet and mixed directly prior to tabletting) using a single station press (Korsch EK0):

| | | | |
|---|---|---|---|
| a | Galen IQ, Na carboxymethylstarch (5%) aqueous granulation in Diosna | no segregation in mixture detectable, | disintegration test: no detectable disintegration after 3 min. |
| b | Galen IQ, Kollidon CL (5%) aqueous granulation in Diosna | no segregation in mixture detectable mixture showed substantial punch deposit upon compression of 3 tablets already | disintegration test: slightly dissolved surface after 3 min. |
| c | Avicel with PVP-solution granulated | significant segregation in mixture detectable | disintegration test: partial disintegration after 3 min. |
| d | MCC + lactose (20:80) with PVP-solution granulated | no segregation in mixture detectable | disintegration test: no detectable disintegration after 3 min. |
| d | MCC + lactose (50:50) with PVP-solution granulated | slight segregation in mixture detectable | disintegration test: partial disintegration after 3 min. |

| | | | | | | | | |
|---|---|---|---|---|---|---|---|---|
| e | Gelcarin + lactose (20% + 80%) + water (57% + 43%) | no segregation in mixture detectable | disintegration test: no detectable disintegration after 3 min. | | | | | |
| f | sugar ester S-1570 + tricalcium-phosphate + Acivel + Gelcarin | significant segregation in mixture detectable | disintegration test: no detectable disintegration after 3 min. | | | | | |
| g | incrustation granulate from saccharose | the granulate could not be processed or only with difficulties blending with particulates is not possible -> thus, no tablets were manufactured | no tablets manufactured | | | | | |

It was not possible to manufacture rapidly disintegrating tablets from the above compositions, probably because the disintegrants lose the disintegrating capacity in the course of the wet granulation process.

Example 4-2

The influence of the matrix material was investigated—dry granulation—roller compaction.

The following compositions were processed by slugging involving the steps of:

weighing/dispensing of components
sieving/blending
manufacture of bi-planar tablets of 20 mm diameter using a single station press (Korsch EK0), 25 kN compression force
breaking the tablets into parts (manually) and sieving using a Frewitt Sieving machine (1.5 mm mesh size)
employing granules as outer phase/matrix material for pellet-tablets The experimental results are summarized in the following table:

| | released after 30 min | excipient | Tramadol Pellets | Avicel 101 | Lactose | Mg-stearate | PVP CL | Esma-spreng | Primojel |
|---|---|---|---|---|---|---|---|---|---|
| a | 87.4 (5 kN) | | 50.00% | 22.25% | 22.25% | 0.50% | 5.00% | | |
| b | 64.1 | | 50.00% | 45.00% | | | 5.00% | | |
| c | n.d. | 15% PEG6000 | 50.00% | 29.5% | | 0.50% | 5.00% | | |
| d | 87.7 | | 50.00% | 45.00% | | | | 5.00% | |
| e | 72.2 | | 50.00% | 45.00% | | | | | |
| f | n.d. | | 50.00% | 45.00% | | | | | 5.00% |
| g | n.d. | 15% NaHCO$_3$ 10% citric acid | 50.00% | 25.00% | | | | | |
| i | 71.1 | 1% xanthan | 50.00% | 44.00% | | | 5.00% | | |
| j-1 | 77.4 | 45% Prosolv SMCCHD90 | 50.00% | | | | 5.00% | | |
| j-2 | 81.2 | 50% Prosolv SMCCHD90 | 50.00% | | | | | | |
| k | 28.4 | 45% Parteck | 50.00% | | | | 5.00% | | |
| l | n.d. | 50% Zaldiar effervescent tablet | 50.00% | | | | | | |
| m | 77.6 | | 50.00% | 22.25% | 22.25% | 0.50% | | | |
| m' | 89.9 | | 50.98% | 21.81% | 21.81% | 0.49% | | | |
| n | 78.2 | | 50.00% | 22.25% | 22.25% | 0.50% | | 5.00% | |
| n' | 92.9 | | 50.98% | 21.81% | 21.81% | 0.49% | | 4.90% | |
| n" | 86.3 | | 50.98% | 21.81% | 21.81% | 0.49% | | 4.90% | |
| o | 60.0 | 45% Prosolv SMCCHD90 | 50.00% | | | | | | |
| o' | 90.5 | 44.12% Prosolv SMCCHD90 | 50.98% | | | | | | |
| o" | 75.4 | 44.12% Prosolv SMCCHD90 | 50.98% | | | | | | |
| p | 74.3 | 45% Prosolv SMCCHD90 | 50.00% | | | | | 5.00% | |
| p' | 93.5 | 44.12% Prosolv SMCCHD90 | 50.98% | | | | | 4.90% | |
| q | 54.3 | | 50.00% | | 42.50% | | | | |
| q' | 60.2 | | 50.98% | | 41.67% | | | | |
| r | 69.3 | | 50.00% | | 42.50% | | | | 7.50% |
| r' | 84.8 | | 50.98% | | 41.67% | | | | 7.35% |
| u | 39.9 | 50% MicroceLac | 50.00% | | | | | | |

-continued

| | | | |
|---|---|---|---|
| u' | 70.3 | 50% MicroceLac | 50.00% |
| v | 78.6 | 50% EASYtab SP | 50.00% |
| v' | 93.5 | 50% EASYtab SP | 50.00% |
| w | n.d. | 50% EASYtab SP | 50.00% |
| w' | n.d. | 50% EASYtab SP | 50.00% |

| | NaCMC | compacted material (compression force 20-25 kN) | tablet surface (compression force 7.5 kN) | disintegration | film coated | form |
|---|---|---|---|---|---|---|
| a | | OK | − | + | no | Round 12 mm biplan (5 kN and 10 kN), oblong 7 × 17 mm (7.5 kN) |
| b | | OK | 0 | + | no | Round 12 mm biplan |
| c | | OK | − | −− | no | Round 12 mm biplan |
| d | | slightly unstable | ++ | ++ | no | Round 12 mm biplan |
| e | 5.00% | OK | 0 | + | no | Round 12 mm biplan |
| f | | OK | 0 | − | no | Round 12 mm biplan |
| g | | adheres punch to matrix | − | −− | no | Round 12 mm biplan |
| i | | can only be compacted with difficulties | − | 0 | no | Round 12 mm biplan |
| j-1 | | OK | + | ++ | no | Round 12 mm biplan |
| j-2 | | OK | 0 | ++ | no | Round 12 mm biplan |
| k | | OK | 0 | + | no | |
| l | | adheres punch to matrix | − | −− | no | Round 12 mm biplan |
| m | 5.00% | OK | + | | no | Round 12 mm biplan |
| m' | 4.90% | OK | + | | yes | Round 12 mm biplan |
| n | | OK | 0 | | no | Round 12 mm biplan |
| n' | | OK | 0 | | yes | Round 12 mm biplan |
| n'' | | OK | 0 | | yes | pentagonal |
| o | 5.00% | OK | 0 | | no | Round 12 mm biplan |
| o' | 4.90% | OK | 0 | | yes | Round 12 mm biplan |
| o'' | 4.90% | OK | 0 | | yes | pentagonal |
| p | | OK | 0 | | no | Round 12 mm biplan |
| p' | | OK | 0 | | yes | Round 12 mm biplan |
| q | 7.50% | OK | 0 | | no | Round 12 mm biplane |
| q' | 7.35% | OK | 0 | | yes | Round 12 mm biplane |
| r | | OK | 0 | | no | Round 12 mm biplane |
| r' | | OK | 0 | | yes | Round 12 mm biplane |
| u | | | | | no | Round 12 mm biplane |
| u' | | | | | yes | Round 12 mm biplane |
| v | | | | | no | Round 12 mm biplane |

| | | | | |
|---|---|---|---|---|
| v' | + | + | yes | Round 12 mm biplane |
| w | + | ++ | no | Round 12 mm biplane |
| w' | | | yes | Round 12 mm biplan |

++ good,
+ satisfactory,
0 acceptable,
− deficient,
−− inacceptable

It is clear from the experimental data provided in the above table (column 3, "released after 30 min") that the coating of the particulates causes a substantial acceleration of drug release (m vs. m'; n vs. n' and n"; o vs. o' and o"; p vs. p'; q vs. q'; r vs. r; u vs. u'; v vs. v'; w vs. w).

Figure 4:
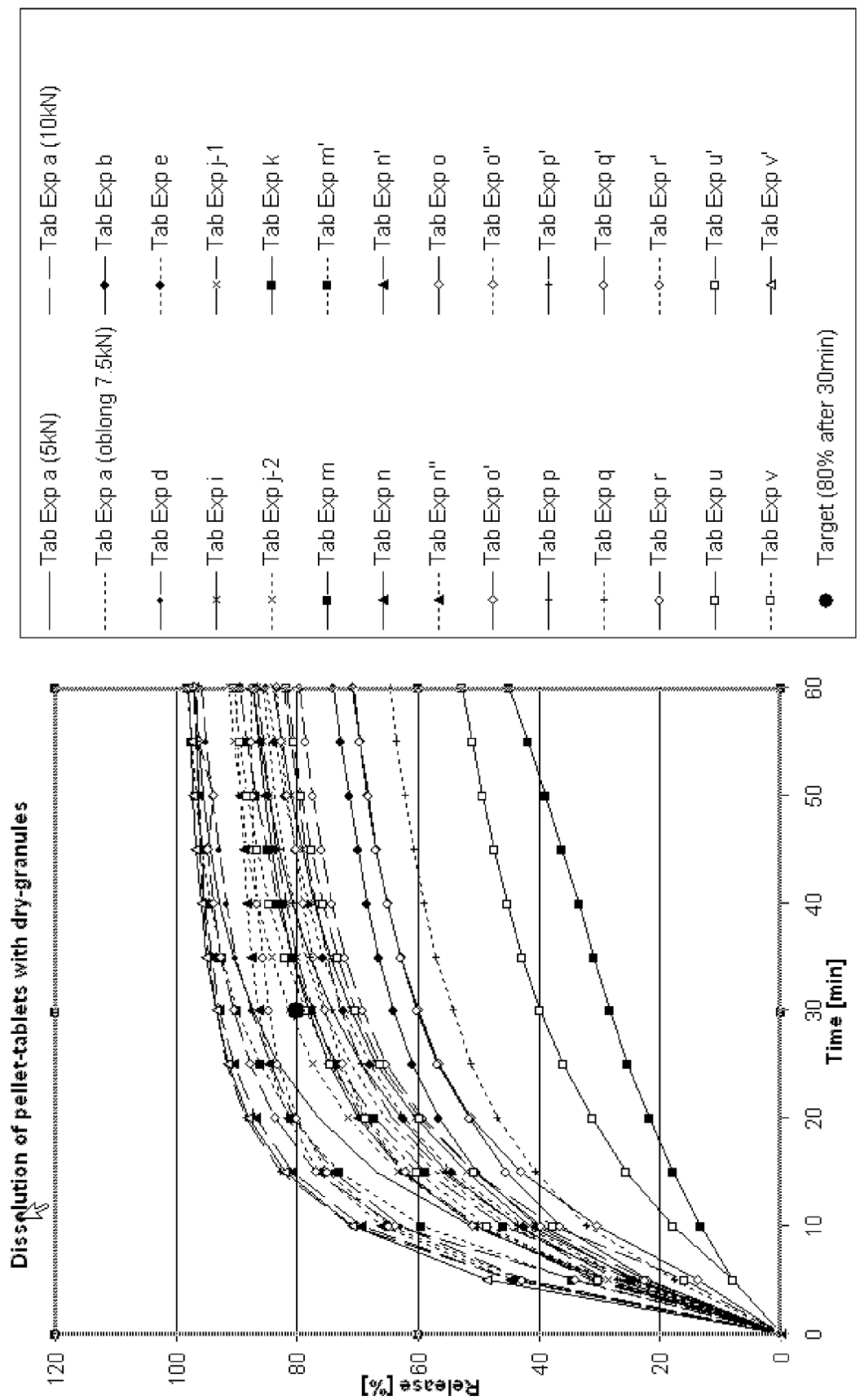
FIG. 4 shows in vitro release profiles of different tablets according to the invention having different compositions.

The release characteristics of tablets containing the thus compacted matrix material were investigated. The results are depicted in FIG. 4 (900 mL HCl, 50 rpm, paddle apparatus without sinker).

Example 4-3

Since the slugging method is not state of the art for dry granulation, corresponding tests concerning dry granulation were conducted by means of a roller compactor. This has the advantage that all relevant parameters (roller displacement, compression force, granulator size) can be adjusted such that a granulate having the desired properties is obtained (particle size, hardness, compressibility, density).

Parameters (Gerteis MiniPactor):
 roller displacement: 2 to 3 mm
 revolution velocity: 2 to 5 rpm
 compaction force: 3 to 15 kN/cm
 screen size: 1.0 to 1.25 to 1.5 to 2.0 mm The thus prepared compacts (dry granulates) were blended with particulates and compressed to tablets. Upon blending, lubricant (magnesium stearate and sodium stearylfumarate, respectively) was added as an external excipient neither contained in the compacts nor in the particulates.

| | Batch | | | | |
|---|---|---|---|---|---|
| | #1 | #2 | #3 | #4 | #5 |
| Avicel PH 101 | 95.00% | | 50.00% | | |
| Esma Spreng | 5.00% | | | | |
| Prosolv SMCC HD 90 | | 95.00% | | 100.00% | |
| Na-CMC | | 5.00% | | | |
| Lactose Monohydrate 230 | | | 50.00% | | |
| Prosolv Easytab | | | | | 100.00% |

The experiments revealed that tablets made from compacts and made from slugging-granulates show a similarly fast release.

Confirming experiments:

| | Batch | | | | | | |
|---|---|---|---|---|---|---|---|
| | #6 | #7 | #8 | #9 | #10 | #11 | #12 |
| Avicel PH 101 | 89.5% | 94.5 | | 89% | 89.50% | | 89.70% |
| Avicel DG | | | | | | 89.5% | |
| Esma Spreng | 10.00% | 5% | | | | | |
| Prosolv SMCC HD 90 | | | 87.5% | | | | |
| Na-CMC | | | 12% | | | | |
| PVP CL | | | | 10% | 10% | 10% | 10% |
| Na-stearylfumarate | | | | 1% | | | |
| Mg stearate | 0.5 | 0.5 | 0.5% | | 0.5 | 0.5% | 0.3% |

Example 4-4

Tablets (500 mg) were prepared from the particulates according to Example 2-5 (250 mg) and the matrix material according to Example 4-3 #12 (250 mg).

The in vitro release was determined according to Ph. Eur.:

| time | % released (n = 6) |
|---|---|
| 0 | 0.0 |
| 5 | 56.8 |
| 10 | 83.4 |
| 15 | 93.3 |
| 20 | 98.1 |
| 25 | 99.9 |
| 30 | 101.1 |
| 35 | 101.4 |
| 40 | 101.7 |
| 45 | 101.9 |
| 50 | 102.0 |
| 55 | 102.0 |
| 60 | 102.0 |

The in vitro release of the tablets was compared to a non-tamper resistant commercial product containing Tapentadol HCl (film coated tablets). After 30 minutes (according to Ph. Eur. 2.9.3), both formulations released the entire amount of the pharmacologically active ingredient (100%).

Example 5

The mechanical properties of conventional, commercial neutral pellets were investigated under the following conditions:

|  | 5-1 (comparative) | 5-2 | 5-3 |
|---|---|---|---|
| product | pellets neutral (Hans G. Werner GmbH & Co.) | tramadol TRF IR pellets | tramadol TRF IR pellets |
| Tramadol HCl |  | 46.59 wt.-% | 4.17 wt.-% |
| PEG 6000 |  | 8.31 wt.-% | 8.33 wt.-% |
| vitamin E |  | 0.10 wt.-% | 0.20 wt.-% |
| PEO |  | 45.00 wt.-% | 87.30 wt.-% |
| diameter pellets | 0.85 mm-1.00 mm | | |
| test equipment | Zwick/Roell | | |
| type | BTC-FR2.5TH.D09 | | |
| force sensor | KAF-TC/2.5 kN | | |
| software applications | testXpert V10.11 | | |
| measuring equipment | plate 2.5 cm × 9.0 cm + ambos 2.0 cm × 4.0 cm | | |
| speed | 10 mm/min | | |
| softend | 192 mm | 192 mm | 192 mm |

The reduction of the displacement between plate and ambos x in mm (="compression [c]") and the corresponding force f in N were measured. The maximum force $f_{max}$ measured during the measurement and the corresponding reduction of displacement $x_{max}$ are summarized in the table here below:

|  | 5-1 (FIG. 7) | | 5-2 (FIG. 8) | | 5-3 (FIG. 9) | |
|---|---|---|---|---|---|---|
|  | $f_{max}$ [N] | $x_{max}$ [mm] | $f_{max}$ [N] | $x_{max}$ [mm] | $f_{max}$ [N] | $x_{max}$ [mm] |
| mean | 5.272 | 0.01 | 587.285 | 0.87 | 588.255 | 0.89 |
| s | 2.129 | 0.03 | 2.320 | 0.06 | 2.897 | 0.05 |
| v | 40.37 | 198.70 | 0.40 | 6.73 | 0.49 | 5.13 |
| min | 2.260 | 0.00 | 585.226 | 0.82 | 583.385 | 0.82 |
| max | 8.432 | 0.08 | 592.581 | 1.00 | 592.413 | 0.96 |

It becomes clear from the above data that the comparative particulates of example 5-1 break at very low forces of only about 5 N and can be deformed by less than 0.1 mm. In contrast, the inventive particulates of examples 5-2 and 5-3 do not break at all, and can be deformed (flattened) by more than 0.8 mm.

Figure 7:
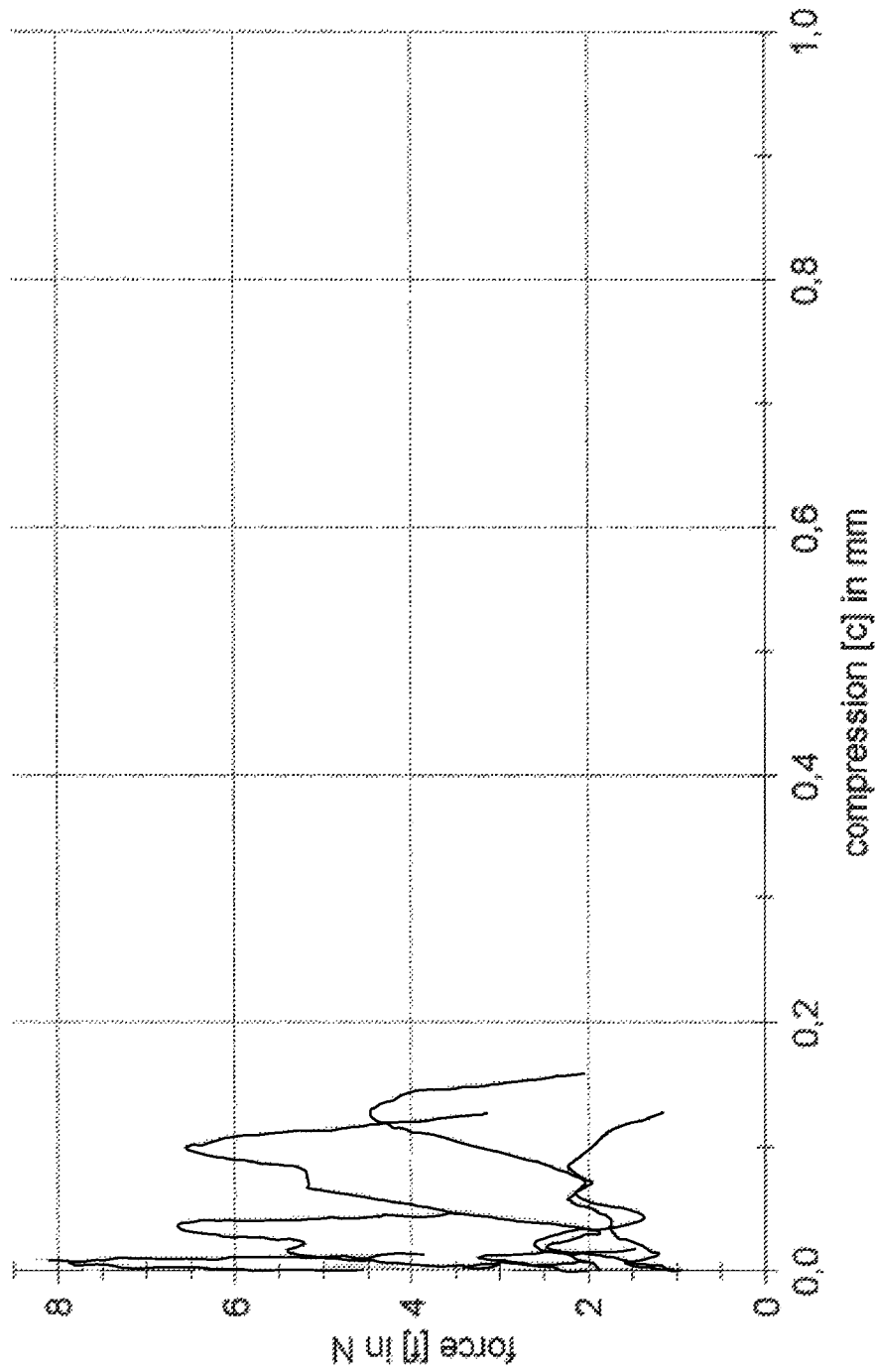
FIG. 7 shows the distance-force-diagram obtained by measuring the mechanical properties of conventional particulates.
Figure 8:
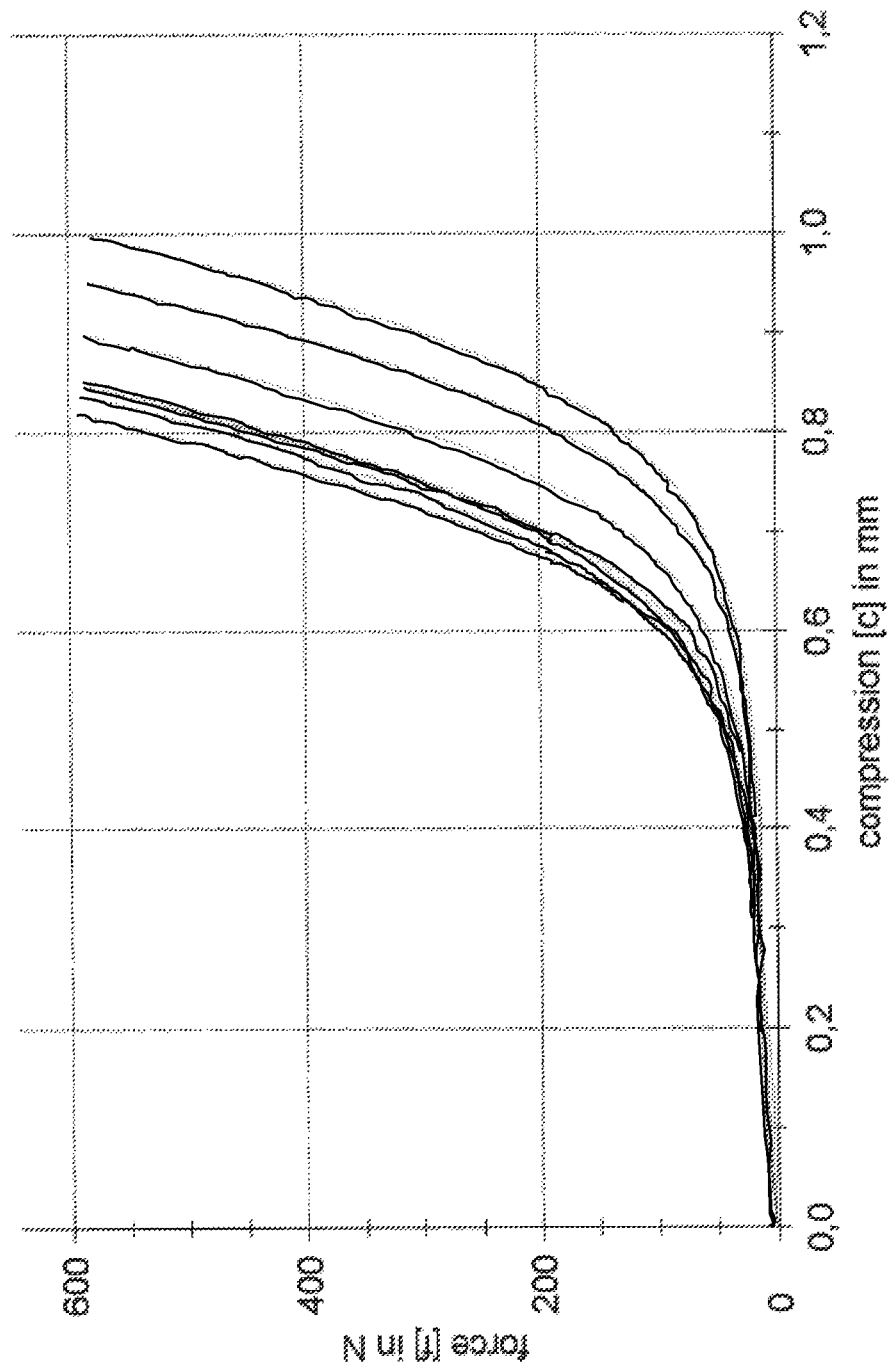
FIG. 8 shows the distance-force-diagram obtained by measuring the mechanical properties of particulates according to the invention.
Figure 9:
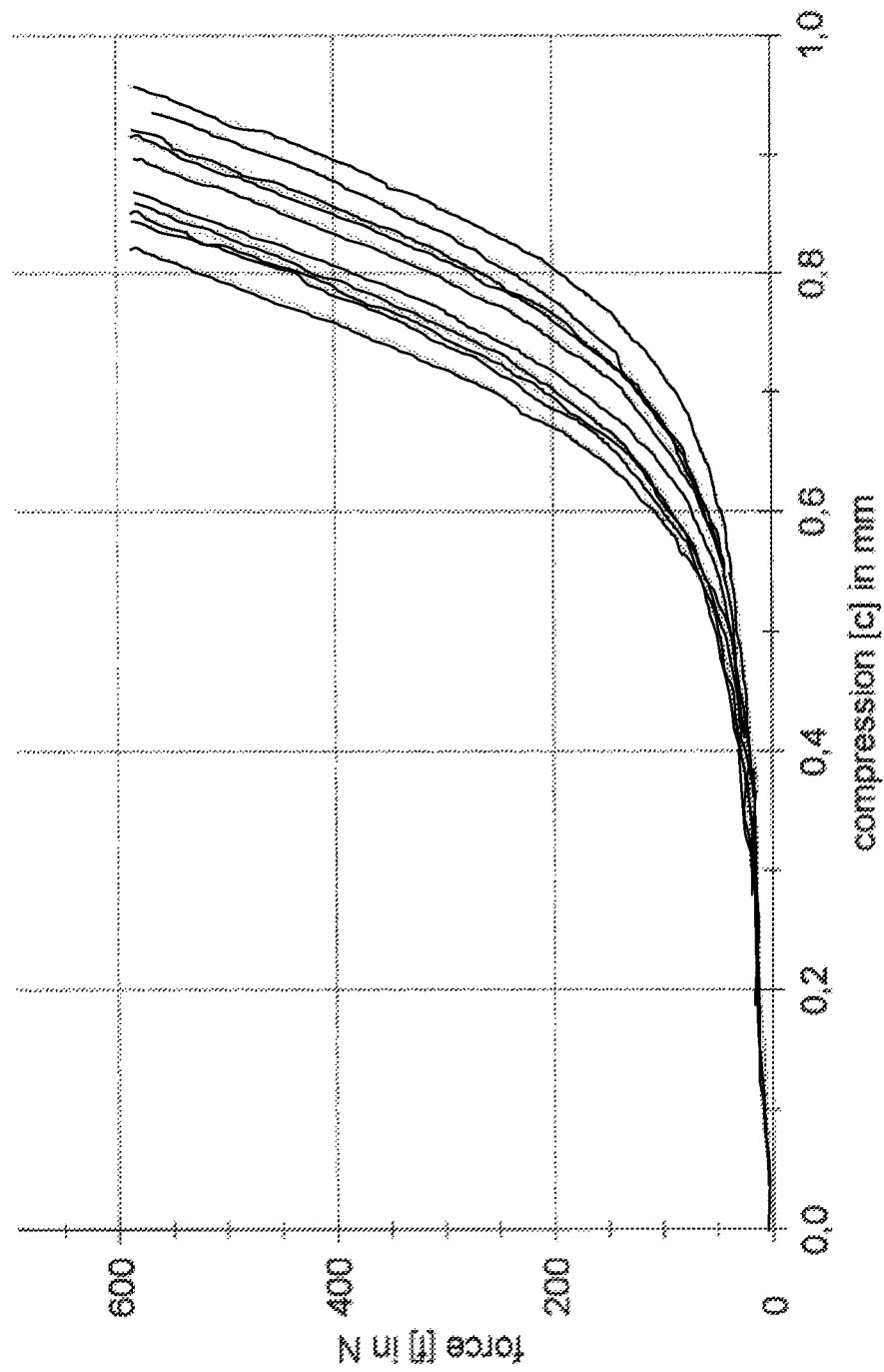
FIG. 9 shows the distance-force-diagram obtained by measuring the mechanical properties of particulates according to the invention.

The corresponding force-displacement-diagrams are shown in FIGS. 7, 8 and 9, respectively.

The invention claimed is:

1. A tamper-resistant tablet comprising:
   (i) a matrix material in an amount of at least 40 wt.-% based on a total weight of the tablet; and
   (ii) a plurality of coated particulates in an amount of less than or equal to 60 wt.-% based on the total weight of the tablet; wherein said coated particulates comprise (a) a pharmacologically active compound selected from the group consisting of stimulants and (b) a physiologically acceptable polymer; wherein the physiologically acceptable polymer is a polyalkylene oxide having a weight average molecular weight of at least 500,000 g/mol; wherein the physiologically acceptable polymer is present in said coated particulates in an amount of at least 25 wt.-% based on a total weight of coated particulates; wherein the coated particulates comprise a coating comprising a coating material comprising a water-soluble polymer selected from the group consisting of cellulose esters, cellulose ethers, poly(meth) acrylates, vinyl polymers, and natural film formers; wherein said coated particulates form a discontinuous phase within the matrix material; wherein said coated particulates do not comprise a disintegrant; and wherein said coated particulates have a breaking strength of at least 300 N;
   said tablet providing under in vitro conditions immediate release of the pharmacologically active compound in accordance with European Pharmacopoeia (Ph. Eur.).

2. The tablet according to claim 1, which has under in vitro conditions a disintegration time measured in accordance with Ph. Eur. of at most 3 minutes.

3. The tablet according to claim 1, wherein the coated particulates have an average diameter of about 1000±250 μm and/or an average length of about 750±250 μm.

4. The tablet according to claim 1, wherein the content of the polymer is at least 25 wt.-%, based on the total weight of coated particulates.

5. The tablet according to claim 1, wherein the content of the pharmacologically active compound is at least 25 wt.-%, based on the total weight of coated particulates.

6. The tablet according to claim 1, which has a total weight of 500±200 mg and contains
   (i) 50±10 wt.-% coated particulates having an average particle size of 800±200 μm, wherein the coated particulates comprise
      23±10 wt.-% pharmacologically active compound,
      22±8 wt.-% physiologically acceptable polymer,
      optionally, 4.0±2.5 wt.-% plasticizer, and
      optionally, 0.05±0.03 wt.-% further excipients; and
   (ii) 49±9 wt.-% matrix material, wherein the matrix material comprises
      43±6 wt.-% filler and/or binder,
      optionally, 5±3 wt.-% disintegrant and
      optionally, 0.15±0.13 wt.-% lubricant;
   all wt.-% being expressed relative to the total weight of the tablet.

7. The tablet according to claim 1, wherein the coated particulates are prepared by a process comprising hot meltextrusion.

8. The tablet according to claim 1, wherein the matrix material is also present in particulate form.

9. The tablet according to claim 1, wherein the matrix material comprises binder, filler, disintegrant and/or lubricant.

10. A method of treating a condition in a patient in need thereof by administering to a patient in need of such treating a tablet comprising an effective amount therefor of a pharmacologically active compound, wherein the tablet is a tablet according to claim 1.

11. The tablet according to claim 1, which, under physiological conditions, releases at least 86% of the pharmacologically active compound originally contained in the tablet within 30 minutes.

12. The tablet according to claim 1, which, under physiological conditions, releases at least 82% of the pharmacologically active compound originally contained in the tablet within 10 minutes.

13. The tablet according to claim 1, wherein the coated particulates comprise a water-soluble coating.

14. The tablet according to claim 1, wherein the coated particulates cannot be pulverized with a hammer or with the assistance of a mortar and pestle.

15. A tamper-resistant tablet comprising:
(i) a matrix material in an amount of at least 40 wt.-% based on a total weight of the tablet; and
(ii) a plurality of coated particulates in an amount of less than or equal to 60 wt.-% based the total weight of the tablet; wherein said coated particulates comprise a pharmacologically active compound and a physiologically acceptable polymer; wherein said pharmacologically active compound is selected from the group consisting of stimulants; wherein the physiologically acceptable polymer is a polyalkylene oxide having a weight average molecular weight of at least 500,000 g/mol; wherein the physiologically acceptable polymer is present in said coated particulates in an amount of at least 25 wt.-% based on a total weight of coated particulates; wherein the coated particulates comprise a coating comprising a coating material comprising a water-soluble polymer selected from the group consisting of cellulose esters, cellulose ethers, poly(meth)acrylates, vinyl polymers, and natural film formers; wherein said coated particulates form a discontinuous phase within the matrix material; wherein said coated particulates do not comprise a disintegrant; and wherein said coated particulates have a breaking strength of at least 300 N;

said plurality of coated particulates releasing within 15 minutes at least 60% by weight of the plurality of coated particulates of pharmacologically active compound as monitored in 900 mL 0.1 HCL at 37° C., using a paddle apparatus at 50 rpm; and said tablet providing under in vitro conditions immediate release of the pharmacologically active compound in accordance with European Pharmacopoeia (Ph. Eur.).

* * * * *